(12) United States Patent
Cordonnier

(10) Patent No.: US 12,232,980 B2
(45) Date of Patent: Feb. 25, 2025

(54) PATIENT-SPECIFIC EXPANDABLE SPINAL IMPLANTS AND ASSOCIATED SYSTEMS AND METHODS

(71) Applicant: Carlsmed, Inc., Carlsbad, CA (US)

(72) Inventor: Michael J. Cordonnier, Carlsbad, CA (US)

(73) Assignee: Carlsmed, Inc., Carlsbad, CA (US)

( * ) Notice: Subject to any disclaimer, the term of this patent is extended or adjusted under 35 U.S.C. 154(b) by 0 days.

(21) Appl. No.: 17/835,777

(22) Filed: Jun. 8, 2022

(65) Prior Publication Data

US 2022/0387191 A1    Dec. 8, 2022

Related U.S. Application Data

(60) Provisional application No. 63/208,084, filed on Jun. 8, 2021.

(51) Int. Cl.
| | | |
|---|---|---|
| *A61F 2/46* | (2006.01) | |
| *A61F 2/44* | (2006.01) | |
| *A61F 2/30* | (2006.01) | |

(52) U.S. Cl.
CPC ............ *A61F 2/4611* (2013.01); *A61F 2/442* (2013.01); *A61F 2002/30556* (2013.01); *A61F 2310/00023* (2013.01)

(58) Field of Classification Search
CPC .............................. A61F 2/4455–2/447; A61F 2250/0004–2250/001; A61F 2250/0048;
(Continued)

(56) References Cited

U.S. PATENT DOCUMENTS

| 4,704,686 A | 11/1987 | Aldinger |
| 4,936,862 A | 6/1990 | Walker et al. |

(Continued)

FOREIGN PATENT DOCUMENTS

| CN | 104318009 A | 1/2015 |
| CN | 104353121 A | 2/2015 |

(Continued)

OTHER PUBLICATIONS

ISA: United States Patent and Trademark Office, PCT Application No. PCT/US22/32624, filed Jun. 8, 2022, International Search Report and Written Opinion mailed Oct. 28, 2022, 16 pages.

(Continued)

*Primary Examiner* — Julianna N Harvey
*Assistant Examiner* — Angel Roberto Mora-Velazquez
(74) *Attorney, Agent, or Firm* — Perkins Coie LLP

(57) ABSTRACT

A device for performing intervertebral body fusion between at a vertebral joint, and associated systems and methods for manufacturing the device are disclosed herein. In some embodiments, the device includes an expandable main body configured to be locked in a desired configuration between a superior and an inferior vertebrae at the vertebral joint to facilitate the intervertebral body fusion at the vertebral joint. A first endplate is connected to the main body. The first endplate can include a superior surface having one or more patient-specific features configured to engage and mate with an inferior surface of the superior vertebra. A second endplate is connected to the main body. The second endplate can include an inferior surface having one or more patient-specific features configured to engage and mate with a superior surface of the inferior vertebra.

30 Claims, 19 Drawing Sheets

(58) Field of Classification Search
CPC ........ A61F 2/442–4455; A61F 2/30942; A61F 2002/4633; A61B 34/10; A61B 2034/101–108
See application file for complete search history.

(56) References Cited

U.S. PATENT DOCUMENTS

| | | | |
|---|---|---|---|
| 5,431,562 A | 7/1995 | Andreiko et al. |
| 5,514,180 A | 5/1996 | Heggeness et al. |
| D420,995 S | 2/2000 | Imamura |
| D436,580 S | 1/2001 | Navano |
| 6,315,553 B1 | 11/2001 | Sachdeva |
| 6,540,512 B1 | 4/2003 | Sachdeva |
| 6,696,073 B2 | 2/2004 | Boyce et al. |
| 6,772,026 B2 | 8/2004 | Bradbury |
| 6,932,842 B1 | 8/2005 | Litschko et al. |
| 6,978,188 B1 | 12/2005 | Christensen |
| 6,988,241 B1 | 1/2006 | Guttman |
| 7,174,282 B2 | 2/2007 | Hollister et al. |
| 7,187,790 B2 | 3/2007 | Sabol et al. |
| D548,242 S | 8/2007 | Viegers |
| D614,191 S | 4/2010 | Takano |
| 7,747,305 B2 | 6/2010 | Dean et al. |
| 7,756,314 B2 | 7/2010 | Karau et al. |
| 7,799,077 B2 | 9/2010 | Lang |
| D633,514 S | 3/2011 | Tokunaga |
| D656,153 S | 3/2012 | Imamura |
| 8,147,556 B2 | 4/2012 | Louis et al. |
| 8,246,680 B2 | 8/2012 | Betz |
| 8,265,949 B2 | 9/2012 | Haddad |
| 8,275,594 B2 | 9/2012 | Lin |
| 8,337,507 B2 | 12/2012 | Lang |
| 8,394,142 B2 | 3/2013 | Bertagnoli |
| 8,457,930 B2 | 6/2013 | Shroeder |
| 8,532,806 B1 | 9/2013 | Masson |
| 8,556,983 B2 | 10/2013 | Bojarski et al. |
| 8,644,568 B1 | 2/2014 | Hoffman |
| 8,735,773 B2 | 5/2014 | Lang |
| 8,758,357 B2 | 6/2014 | Frey |
| 8,775,133 B2 | 7/2014 | Schroeder |
| 8,781,557 B2 | 7/2014 | Dean |
| 8,843,229 B2 | 9/2014 | Vanasse |
| 8,855,389 B1 | 10/2014 | Hoffman |
| 8,870,889 B2 | 10/2014 | Frey |
| 9,020,788 B2 | 4/2015 | Lang |
| D735,231 S | 7/2015 | Omiya |
| D737,309 S | 8/2015 | Kito |
| 9,198,678 B2 | 12/2015 | Frey et al. |
| 9,208,558 B2 | 12/2015 | Dean |
| D757,025 S | 5/2016 | Kim |
| D761,842 S | 7/2016 | Johnson |
| 9,381,093 B1 | 7/2016 | Morris et al. |
| 9,411,939 B2 | 8/2016 | Furrer |
| 9,445,907 B2 | 9/2016 | Meridew |
| 9,452,050 B2 | 9/2016 | Miles et al. |
| D774,076 S | 12/2016 | Fuller |
| 9,542,525 B2 | 1/2017 | Arisoy et al. |
| 9,561,113 B2 * | 2/2017 | Howard ................ A61F 2/4465 |
| 9,642,633 B2 | 5/2017 | Frey et al. |
| 9,693,831 B2 | 7/2017 | Mosnier et al. |
| 9,707,058 B2 | 7/2017 | Bassett |
| 9,715,563 B1 | 7/2017 | Schroeder |
| D797,760 S | 9/2017 | Tsujimura |
| D797,766 S | 9/2017 | Ibsies |
| D798,312 S | 9/2017 | Tsujimura |
| 9,757,245 B2 | 9/2017 | O'Neil et al. |
| D798,894 S | 10/2017 | Ibsies |
| 9,775,680 B2 | 10/2017 | Bojarski et al. |
| 9,782,228 B2 | 10/2017 | Mosnier et al. |
| D812,628 S | 3/2018 | Okado |
| 9,993,341 B2 | 6/2018 | Vanasse |
| 10,034,676 B2 | 7/2018 | Donner |
| D825,605 S | 8/2018 | Jann |
| D826,977 S | 8/2018 | Nakajima |
| 10,089,413 B2 | 10/2018 | Wirx-Speetjens et al. |
| D841,675 S | 2/2019 | Hoffman |
| 10,213,311 B2 | 2/2019 | Mafhouz |
| D845,973 S | 4/2019 | Jaycobs |
| D845,974 S | 4/2019 | Cooperman |
| D847,165 S | 4/2019 | Kolbenheyer |
| D848,468 S | 5/2019 | Ng |
| D849,029 S | 5/2019 | Cooperman |
| D849,773 S | 5/2019 | Jiang |
| 10,292,770 B2 | 5/2019 | Ryan |
| 10,299,863 B2 | 5/2019 | Grbic et al. |
| D854,560 S | 7/2019 | Field |
| D854,561 S | 7/2019 | Field |
| 10,390,958 B2 | 8/2019 | Maclennan |
| D860,237 S | 9/2019 | Li |
| D860,238 S | 9/2019 | Bhardwaj |
| D866,577 S | 11/2019 | Eisert |
| D867,379 S | 11/2019 | Ang |
| D867,389 S | 11/2019 | Jamison |
| 10,463,433 B2 | 11/2019 | Turner et al. |
| D870,762 S | 12/2019 | Mendoza |
| 10,512,546 B2 | 12/2019 | Kamer et al. |
| 10,517,681 B2 | 12/2019 | Roh et al. |
| D872,117 S | 1/2020 | Kobayashi |
| D872,756 S | 1/2020 | Howell |
| D874,490 S | 2/2020 | Dodsworth |
| D875,761 S | 2/2020 | Heffernan |
| D876,454 S | 2/2020 | Knowles |
| D876,462 S | 2/2020 | Li |
| D877,167 S | 3/2020 | Knowles |
| D879,112 S | 3/2020 | Hejazi |
| 10,588,589 B2 | 3/2020 | Bregman-Amitai et al. |
| 10,603,055 B2 | 3/2020 | Donner et al. |
| D880,513 S | 4/2020 | Wang |
| D881,908 S | 4/2020 | Sunil |
| D881,910 S | 4/2020 | Lin |
| 10,621,289 B2 | 4/2020 | Schroeder |
| 10,631,988 B2 | 4/2020 | Arnold et al. |
| D884,008 S | 5/2020 | Thornberg |
| 10,646,236 B2 | 5/2020 | Donner et al. |
| 10,646,258 B2 | 5/2020 | Donner et al. |
| 10,736,698 B2 | 8/2020 | Bohl |
| 10,751,188 B2 | 8/2020 | Guo et al. |
| D896,825 S | 9/2020 | Abel |
| D896,828 S | 9/2020 | Linares |
| D898,054 S | 10/2020 | Everhart |
| D899,438 S | 10/2020 | Crafts |
| 10,806,597 B2 | 10/2020 | Sournac et al. |
| 10,902,944 B1 | 1/2021 | Casey et al. |
| D916,868 S | 4/2021 | Evangeliou |
| D916,879 S | 4/2021 | Mitsumori |
| D918,253 S | 5/2021 | Choe |
| 11,000,334 B1 | 5/2021 | Young |
| D921,675 S | 6/2021 | Kmak |
| D921,677 S | 6/2021 | Kmak |
| D921,687 S | 6/2021 | Kmak |
| D924,909 S | 7/2021 | Nasu |
| D925,567 S | 7/2021 | Hayamizu |
| D927,528 S | 8/2021 | Heisler |
| 11,083,586 B2 | 8/2021 | Cordonnier |
| 11,112,770 B2 | 9/2021 | Roh et al. |
| D933,692 S | 10/2021 | Smith |
| 11,166,764 B2 | 11/2021 | Roh et al. |
| 11,185,369 B2 | 11/2021 | Ryan |
| D937,870 S | 12/2021 | Pinto |
| D937,876 S | 12/2021 | Harvey |
| D938,461 S | 12/2021 | Hoffman |
| D938,986 S | 12/2021 | Grossberg |
| D940,178 S | 1/2022 | Ang |
| D946,022 S | 3/2022 | Nuttbrown |
| D946,023 S | 3/2022 | Nuttbrown |
| D946,024 S | 3/2022 | Vogler-Ivashchanka |
| D946,616 S | 3/2022 | Tsai |
| D958,151 S | 7/2022 | Casey et al. |
| 11,376,076 B2 | 7/2022 | Casey et al. |
| 11,432,943 B2 | 9/2022 | Casey et al. |
| 11,439,514 B2 | 9/2022 | Casey et al. |
| 2002/0016595 A1 | 2/2002 | Michelson |
| 2004/0104512 A1 | 6/2004 | Eidenschink |
| 2004/0210314 A1 | 10/2004 | Michelson |

(56) References Cited

U.S. PATENT DOCUMENTS

| | | |
|---|---|---|
| 2007/0276501 A1 | 11/2007 | Betz |
| 2008/0089566 A1 | 4/2008 | Node-Langlois |
| 2008/0227047 A1 | 9/2008 | Lowe |
| 2009/0062739 A1 | 3/2009 | Anderson |
| 2010/0298942 A1* | 11/2010 | Hansell .............. A61F 2/4611 623/17.16 |
| 2010/0324692 A1 | 12/2010 | Uthgenannt |
| 2012/0150243 A9 | 6/2012 | Crawford et al. |
| 2012/0322018 A1 | 12/2012 | Lowe |
| 2013/0323669 A1 | 12/2013 | Lowe |
| 2014/0072608 A1 | 3/2014 | Karagkiozaki |
| 2014/0074438 A1 | 3/2014 | Furrer |
| 2014/0081659 A1 | 3/2014 | Nawana et al. |
| 2014/0086780 A1 | 3/2014 | Miller |
| 2014/0100886 A1 | 4/2014 | Woods |
| 2014/0164022 A1 | 6/2014 | Reed |
| 2014/0263674 A1 | 9/2014 | Cerveny |
| 2014/0277487 A1* | 9/2014 | Davenport ............ A61F 2/4455 623/17.16 |
| 2014/0350614 A1 | 11/2014 | Frey |
| 2015/0079533 A1 | 3/2015 | Lowe |
| 2015/0105891 A1 | 4/2015 | Golway et al. |
| 2015/0199488 A1 | 7/2015 | Falchuk |
| 2015/0213225 A1 | 7/2015 | Amarasingham |
| 2015/0324490 A1 | 11/2015 | Page |
| 2015/0328004 A1 | 11/2015 | Mafhouz |
| 2015/0332018 A1 | 11/2015 | Rosen |
| 2016/0001039 A1 | 1/2016 | Armour et al. |
| 2016/0015465 A1 | 1/2016 | Steines et al. |
| 2016/0030067 A1 | 2/2016 | Frey et al. |
| 2016/0074048 A1 | 3/2016 | Pavlovskaia |
| 2016/0117817 A1 | 4/2016 | Seel |
| 2016/0143744 A1 | 5/2016 | Bojarski et al. |
| 2016/0184054 A1 | 6/2016 | Lowe |
| 2016/0210374 A1 | 7/2016 | Mosnier et al. |
| 2016/0217268 A1 | 7/2016 | Otto |
| 2016/0242857 A1 | 8/2016 | Scholl |
| 2016/0300026 A1 | 10/2016 | Bogoni et al. |
| 2016/0354039 A1 | 12/2016 | Soto et al. |
| 2016/0354161 A1 | 12/2016 | Deitz |
| 2016/0354213 A1* | 12/2016 | Cowan .................. A61F 2/4465 |
| 2016/0378919 A1 | 12/2016 | McNutt et al. |
| 2017/0000566 A1 | 1/2017 | Gordon |
| 2017/0014169 A1 | 1/2017 | Dean |
| 2017/0020679 A1 | 1/2017 | Maclennan |
| 2017/0035514 A1 | 2/2017 | Fox et al. |
| 2017/0061375 A1 | 3/2017 | Laster |
| 2017/0068792 A1 | 3/2017 | Reiner |
| 2017/0135706 A1 | 5/2017 | Frey et al. |
| 2017/0143494 A1 | 5/2017 | Mahfouz |
| 2017/0143831 A1 | 5/2017 | Varanasi et al. |
| 2017/0216047 A1 | 8/2017 | Hawkes et al. |
| 2017/0220740 A1 | 8/2017 | D'Urso |
| 2017/0252107 A1 | 9/2017 | Turner et al. |
| 2017/0262595 A1 | 9/2017 | Vorhis |
| 2017/0340447 A1 | 11/2017 | Mahfouz |
| 2017/0354510 A1 | 12/2017 | O'Neil et al. |
| 2017/0367645 A1 | 12/2017 | Klinder |
| 2018/0008349 A1 | 1/2018 | Gillman |
| 2018/0113992 A1 | 4/2018 | Eltorai et al. |
| 2018/0116727 A1 | 5/2018 | Caldwell et al. |
| 2018/0168499 A1 | 6/2018 | Bergold |
| 2018/0168731 A1 | 6/2018 | Reid |
| 2018/0185075 A1 | 7/2018 | She |
| 2018/0233222 A1 | 8/2018 | Daley |
| 2018/0233225 A1 | 8/2018 | Experton |
| 2018/0250075 A1 | 9/2018 | Cho |
| 2018/0303552 A1 | 10/2018 | Ryan |
| 2018/0303616 A1 | 10/2018 | Bhattacharyya et al. |
| 2018/0308569 A1 | 10/2018 | Luellen |
| 2018/0318100 A1 | 11/2018 | Altarac |
| 2018/0338841 A1 | 11/2018 | Miller et al. |
| 2019/0065685 A1 | 2/2019 | Pickover |
| 2019/0201106 A1 | 7/2019 | Siemionow |
| 2019/0262084 A1 | 8/2019 | Roh et al. |
| 2019/0266597 A1 | 8/2019 | Mohtar |
| 2019/0328929 A1 | 10/2019 | Kugler et al. |
| 2019/0333622 A1 | 10/2019 | Levin |
| 2019/0354693 A1 | 11/2019 | Yoon |
| 2019/0380792 A1 | 12/2019 | Poltaretskyi et al. |
| 2020/0021570 A1 | 1/2020 | Lin |
| 2020/0078180 A1* | 3/2020 | Casey .................... A61B 34/10 |
| 2020/0085509 A1 | 3/2020 | Roh et al. |
| 2020/0170802 A1 | 6/2020 | Casey et al. |
| 2020/0246162 A1 | 8/2020 | Schultz et al. |
| 2020/0261156 A1 | 8/2020 | Schmidt |
| 2020/0289288 A1 | 9/2020 | Müller et al. |
| 2020/0315708 A1 | 10/2020 | Mosnier et al. |
| 2020/0323654 A1* | 10/2020 | Marrapode .......... A61F 2/4455 |
| 2021/0059822 A1 | 3/2021 | Casey et al. |
| 2021/0064605 A1 | 3/2021 | Balint |
| 2021/0085482 A1 | 3/2021 | Flickinger et al. |
| 2021/0145519 A1 | 5/2021 | Mosnier et al. |
| 2021/0210189 A1* | 7/2021 | Casey .................. B29C 64/393 |
| 2021/0287770 A1 | 9/2021 | Anderson |
| 2021/0382457 A1 | 12/2021 | Roh et al. |
| 2022/0000625 A1 | 1/2022 | Cordonnier |
| 2022/0006642 A1 | 1/2022 | Maj et al. |
| 2022/0039965 A1* | 2/2022 | Casey ................. A61F 2/30942 |
| 2022/0047402 A1 | 2/2022 | Casey et al. |
| 2022/0110686 A1 | 4/2022 | Roh et al. |
| 2022/0160405 A1 | 5/2022 | Casey et al. |
| 2022/0160518 A1 | 5/2022 | Casey et al. |
| 2022/0401150 A1 | 12/2022 | Cordonnier |
| 2023/0052263 A1 | 2/2023 | Casey et al. |
| 2023/0086886 A1 | 3/2023 | Casey et al. |

FOREIGN PATENT DOCUMENTS

| | | |
|---|---|---|
| CN | 204468348 U | 7/2015 |
| CN | 105796214 A | 7/2016 |
| CN | 106202861 | 12/2016 |
| CN | 107220933 | 9/2017 |
| CN | 108670506 A | 10/2018 |
| CN | 110575289 A | 12/2019 |
| CN | 111281613 A | 6/2020 |
| CN | 112155792 A | 1/2021 |
| CN | 113643790 | 11/2021 |
| EP | 3120796 A1 | 1/2017 |
| WO | 9507509 A1 | 3/1995 |
| WO | 2004110309 A2 | 12/2004 |
| WO | 2010151564 A1 | 12/2010 |
| WO | 2012154534 A1 | 11/2012 |
| WO | 2014180972 A2 | 11/2014 |
| WO | 2016172694 A1 | 10/2016 |
| WO | 2019018013 A1 | 1/2019 |
| WO | 2019112917 A1 | 6/2019 |
| WO | 2019148154 A1 | 8/2019 |
| WO | 2019165152 | 8/2019 |
| WO | 2019241167 A1 | 12/2019 |
| WO | 2022045956 A1 | 3/2022 |
| WO | 2022109097 A1 | 5/2022 |
| WO | 2022261171 | 12/2022 |
| WO | 2022266313 A1 | 12/2022 |
| WO | 2023034405 A1 | 3/2023 |

OTHER PUBLICATIONS

Endo, Kenji et al. "Measurement of whole spine sagittal alignment using the Slot radiography of the Sonialvision safire series clinical application." Medical Now, No. 78; Aug. 2015, 4 pages.

Eshkalak, S.K. et al., "The role of three-dimensional printing in healthcare and medicine." Materials and Design 194, Jul. 10, 20202, 15 pages.

Extended European Search Report for European Application No. 18885367.5, mailed Aug. 16, 2021, 8 pages.

Extended European Search Report for European Application No. 19859930.0, mailed Jun. 22, 2022, 7 pages.

International Search Report and Written Opinion for International Application No. PCT/US19/50885, mailed Jan. 28, 2020, 21 pages.

International Search Report and Written Opinion for International Application No. PCT/US19/63855, mailed Feb. 14, 2020, 15 pages.

(56) References Cited

OTHER PUBLICATIONS

International Search Report and Written Opinion for International Application No. PCT/US21/44878, mailed Nov. 16, 2021, 18 pages.

International Search Report and Written Opinion for International Application No. PCT/US21/45503, mailed Jan. 11, 2022, 19 pages.

International Search Report and Written Opinion for International Patent Application No. PCT/US21/60074, mailed Mar. 17, 2022, 21 pages.

International Search Report and Written Opinion for International Patent Application No. PCT/US2018/063530, mailed Feb. 12, 2019, 16 pages.

International Search Report and Written Opinion for International Patent Application No. PCT/US21/12065, mailed Apr. 29, 2021, 19 pages.

International Search Report and Written Opinion for International Patent Application No. PCT/US21/59837, mailed Feb. 7, 2022, 19 pages.

Majdouline et al., "Preoperative assessment and evaluation of instrumentation strategies for the treatment of adolescent idiopathic scoliosis: computer simulation and optimization." Scoliosis 7, 21 (2012), pp. 1-8.

Materialise Mimics, "Efficiently turn scans into accurate virtual 3D models," Retrieved on Nov. 1, 2019 at www.materialize.com/en/medical/software/mimics, 1 page.

Pimenta, Dr. Luiz, "Current Surgical Strategies to Restore Proper Sagittal Alignment," Journal of Spine 2015, vol. 4, Issue 4, 2 pages.

Pruthi, G. et al., "Comprehensive review of guidelines to practice prosthodontic and implant procedures during COVID-19 pandemic." Journal of Oral Biology and Craniofacial Research 10, Oct. 17, 2020, 8 pages.

International Search Report and Written Opinion for International Application No. PCT/US22/33775, mailed Sep. 8, 2022, 17 pages.

International Search Report and Written Opinion for International Application No. PCT/US24/10202, mailed Jul. 16, 2024, 14 pages.

\* cited by examiner

| PATIENT | |
|---|---|
| Pt. ID | JDoe |
| Metric | Value |
| Age | 58 |
| Gender | M |
| BMI | 32 |
| LL | 40 |
| PI | 55 |
| Levels | 4 |

| | Pt. ID | X123 | Pt. ID | Y456 | Pt. ID | Z789 | Pt. ID | A246 |
|---|---|---|---|---|---|---|---|---|
| Study Group X | Metric | Value | Metric | Value | Metric | Value | Metric | Value |
| | Age | 56 | Age | 66 | Age | 63 | Age | 73 |
| | Gender | F | Gender | F | Gender | M | Gender | M |
| | BMI | 38 | BMI | 38 | BMI | 30 | BMI | 30 |
| | LL | 36 | LL | 41 | LL | 39 | LL | 40 |
| | PI | 51 | PI | 52 | PI | 50 | PI | 48 |
| | Levels | 3 | Levels | 4 | Levels | 4 | Levels | 5 |
| | Outcome | | Outcome | | Outcome | | Outcome | |
| | Fused | Y | Fused | Y | Fused | Y | Fused | N |
| | HRQL | A | HRQL | B | HRQL | A | HRQL | D |
| | Complications | 0 | Complications | 0 | Complications | 1 | Complications | 0 |
| | Surg. Intervention | | Surg. Intervention | | Surg. Intervention | | Surg. Intervention | |
| | Imp. design | Stock | Imp. design | Stock | Imp. design | Stock | Imp. design | Stock |
| | Imp placemt | A | Imp placemt | A | Imp placemt | B | Imp placemt | B |
| | Surg. Appr. | Lat | Surg. Appr. | Ant | Surg. Appr. | Lat | Surg. Appr. | Post |

| | Pt. ID | B135 | Pt. ID | C468 | Pt. ID | D357 | Pt. ID | E468 |
|---|---|---|---|---|---|---|---|---|
| Practice Y | Metric | Value | Metric | Value | Metric | Value | Metric | Value |
| | Age | 73 | Age | 60 | Age | 58 | Age | 78 |
| | Gender | F | Gender | M | Gender | M | Gender | M |
| | BMI | 37 | BMI | 32 | BMI | 29 | BMI | 30 |
| | LL | 40 | LL | 40 | LL | 39 | LL | 40 |
| | PI | 55 | PI | 55 | PI | 52 | PI | 48 |
| | Levels | 4 | Levels | 4 | Levels | 4 | Levels | 3 |
| | Outcome | | Outcome | | Outcome | | Outcome | |
| | Fused | Y | Fused | Y | Fused | N | Fused | N |
| | HRQL | A | HRQL | A | HRQL | C | HRQL | F |
| | Complications | 0 | Complications | 0 | Complications | 1 | Complications | 0 |
| | Surg. Intervention | | Surg. Intervention | | Surg. Intervention | | Surg. Intervention | |
| | Imp. design | PS | Imp. design | PS | Imp. design | Stock | Imp. design | Stock |
| | Imp placemt | A | Imp placemt | A | Imp placemt | B | Imp placemt | B |
| | Surg. Appr. | Ant | Surg. Appr. | Ant, Lat | Surg. Appr. | Post | Surg. Appr. | Lat |

| | Pt. ID | F135 | Pt. ID | G468 | Pt. ID | H357 | Pt. ID | J468 |
|---|---|---|---|---|---|---|---|---|
| University Z | Metric | Value | Metric | Value | Metric | Value | Metric | Value |
| | Age | 73 | Age | 60 | Age | 63 | Age | 71 |
| | Gender | F | Gender | M | Gender | M | Gender | M |
| | BMI | 33 | BMI | 42 | BMI | 31 | BMI | 30 |
| | LL | 40 | LL | 40 | LL | 39 | LL | 40 |
| | PI | 55 | PI | 55 | PI | 52 | PI | 50 |
| | Levels | 4 | Levels | 4 | Levels | 4 | Levels | 3 |
| | Outcome | | Outcome | | Outcome | | Outcome | |
| | Fused | Y | Fused | Y | Fused | Y | Fused | N |
| | HRQL | A | HRQL | A | HRQL | A | HRQL | F |
| | Complications | 0 | Complications | 0 | Complications | 1 | Complications | 2 |
| | Surg. Intervention | | Surg. Intervention | | Surg. Intervention | | Surg. Intervention | |
| | Imp. design | PS | Imp. design | PS | Imp. design | PS | Imp. design | Stock |
| | Imp placemt | A | Imp placemt | A | Imp placemt | B | Imp placemt | B |
| | Surg. Appr. | Post | Surg. Appr. | Ant, Lat | Surg. Appr. | Ant, Lat | Surg. Appr. | Lat |

*FIG. 5B*

|  | Pre-op Similarity | | Outcome quotient |
|---|---|---|---|
| Pt. ID | Value | | |
| 510a → X123 | 9 | | 1 |
| Y456 | 18 | | 2 |
| Z789 | 11 | | 2 |
| A246 | 25 | | 9 |
| B135 | 20 | | 1 |
| 510b → C468 | 2 | | 1 |
| 510c → D357 | 5 | | 9 |
| E468 | 30 | | 10 |
| F135 | 16 | | 1 |
| G468 | 12 | | 1 |
| 510d → H357 | 8 | | 2 |
| J468 | 21 | | 12 |

*FIG. 5C*

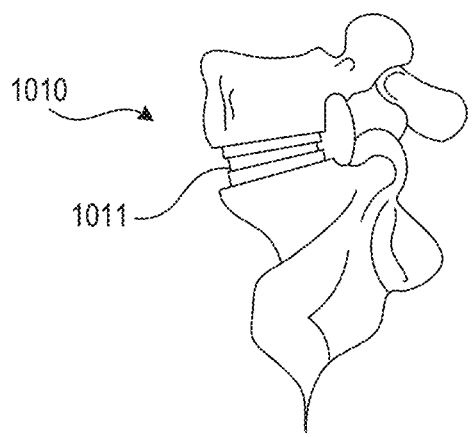
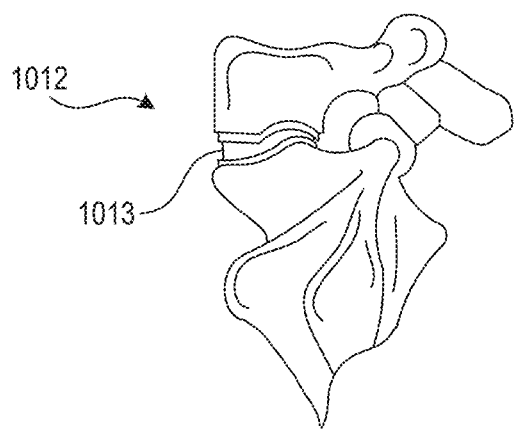
FIG. 10A   FIG. 10B
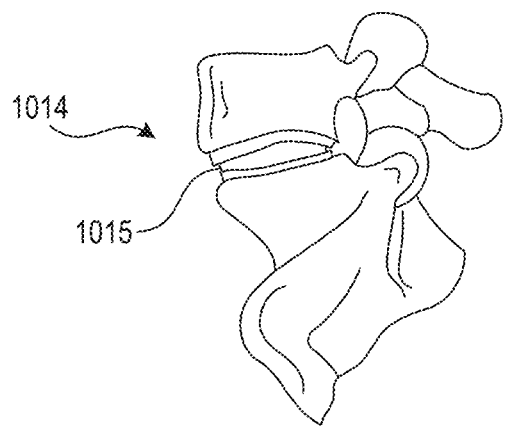
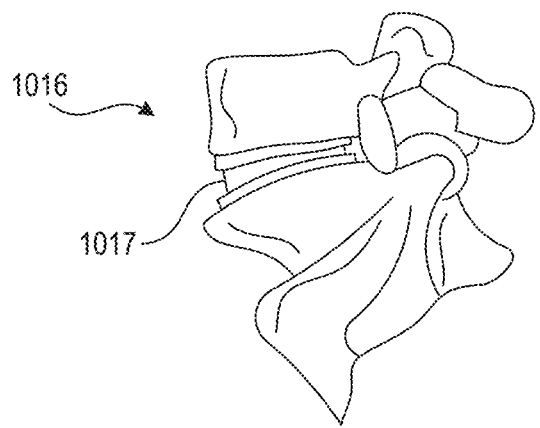
FIG. 10C   FIG. 10D
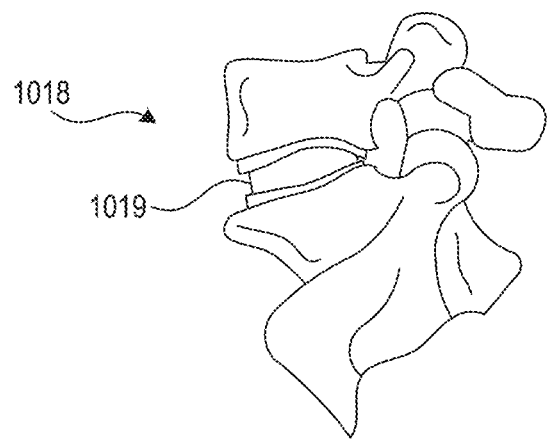
FIG. 10E

PATIENT-SPECIFIC EXPANDABLE SPINAL IMPLANTS AND ASSOCIATED SYSTEMS AND METHODS

CROSS-REFERENCE TO RELATED APPLICATION(S)

The present application claims priority to U.S. Provisional Patent Application No. 63/208,084, filed Jun. 8, 2021, the disclosure of which is incorporated by reference herein in its entirety and for all purposes.

TECHNICAL FIELD

The present disclosure is generally related to patient-specific medical care, including systems using prescriptive analytics to design, manufacture, and/or deliver surgical devices, such as expandable devices, intervertebral body fusion devices, and spinal implants.

BACKGROUND

Orthopedic implants are used to correct numerous different maladies in a variety of contexts, including spine surgery, hand surgery, shoulder and elbow surgery, total joint reconstruction (arthroplasty), skull reconstruction, pediatric orthopedics, foot and ankle surgery, musculoskeletal oncology, surgical sports medicine, and orthopedic trauma. Spine surgery itself may encompass a variety of procedures and targets, such as one or more of the cervical spine, thoracic spine, lumbar spine, or sacrum, and may be performed to treat a deformity or degeneration of the spine and/or related back pain, leg pain, or other body pain. Common spinal deformities that may be treated using an orthopedic implant include irregular spinal curvature such as scoliosis, lordosis, or kyphosis (hyper- or hypo-), and irregular spinal displacement (e.g., spondylolisthesis). Other spinal disorders that can be treated using an orthopedic implant include osteoarthritis, lumbar degenerative disc disease or cervical degenerative disc disease, lumbar spinal stenosis, and cervical spinal stenosis.

BRIEF DESCRIPTION OF THE DRAWINGS

FIGS. 5A-5C illustrate exemplary data sets that can be used by and/or generated in connection with various methods of the present technology.

FIGS. 10A-10E are sides views of spinal segments illustrating vertebra topologies and patient-specific intervertebral body fusion devices.

Figure 1A:
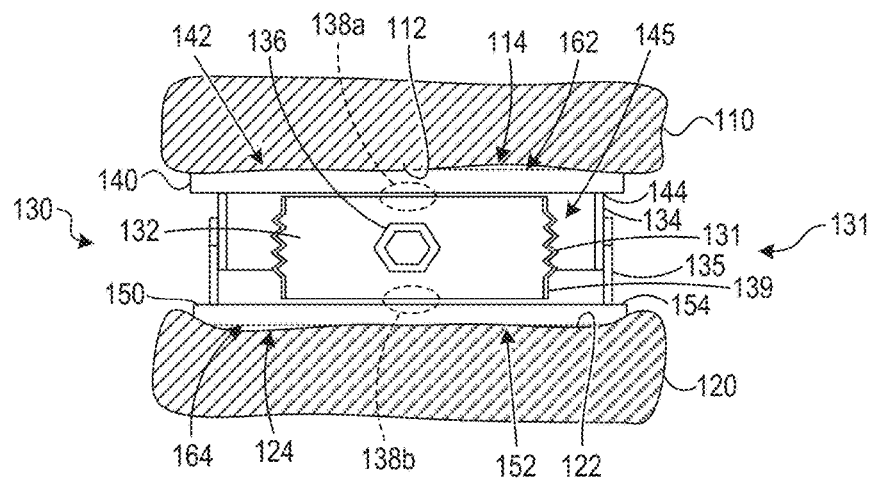
FIGS. 1A and 1B illustrate a deployed patient-specific intervertebral body fusion device positioned between a superior vertebra and an inferior vertebra in accordance with some embodiments of the present technology.

The drawings have not necessarily been drawn to scale. Similarly, some components and/or operations can be separated into different blocks or combined into a single block for the purpose of discussion of some of the implementations of the present technology. Moreover, while the technology is amenable to various modifications and alternative forms, specific implementations have been shown by way of example in the drawings and are described in detail below. The intention, however, is not to limit the technology to the particular implementations described. On the contrary, the technology is intended to cover all modifications, equivalents, and alternatives falling within the scope of the technology as defined by the appended claims.

DETAILED DESCRIPTION

The following headings are provided for ease of readability. While embodiments of the present technology are described under the following headings, other embodiments of the technology can include elements discussed under multiple headings. Accordingly, the fact that an embodiment may be discussed under a particular heading does not necessarily limit that embodiment to only the elements discussed under that heading.

Overview

Spinal fusion, also called spondylodesis or spondylosyndesis, is a neurosurgical or orthopedic surgical technique that joins two or more vertebrae. Spinal fusion can be used to treat a variety of conditions affecting any level of the spine—lumbar, cervical and thoracic. In general, spinal fusion is performed to decompress and stabilize the spine, and the result can prevent any movement between the fused vertebrae. Spinal fusion is most commonly performed to relieve the pain and pressure from mechanical pain of the vertebrae or on the spinal cord that results when a disc wears out (e.g., resulting from degenerative disc disease). Other common pathological conditions that are treated by spinal fusion include spinal stenosis, spondylolisthesis, spondylosis, spinal fractures, scoliosis, and kyphosis.

As described in detail throughout this Detailed Description, the present technology includes intervertebral body fusion ("IBF") devices that can be used for spinal fusion. The IBF device can help to restore a height between vertebral bodies, restore lordotic and coronal misalignment, and/or stabilize the spine until bony fusion occurs between vertebral bodies. Example IBF devices can be configured for anterior lumbar interbody fusion (ALIF), lateral lumbar interbody fusion (LLIF), oblique lateral interbody fusion (OLIF), posterior lumbar interbody fusion (PLIF), or transforaminal lumbar interbody fusion (TLIF). In some embodiments, the IBF device can be a cervical cage. IBF devices can also have multiple expandable mechanisms that provide intraoperative adjustability. In some embodiments, expandable IBF devices also provide adjustability (e.g., pre-, intra-, and/or postoperative adjustability) of, for example, spinal curvature, vertebral heights, lordotic restoration, and/or coronal restoration.

In some embodiments, IBF devices are personalized to patient-specific features and/or concerns in accordance with a pre-operative plan for height restoration, lordotic and coronal correction, and/or optimal endplate coverage. For example, an expandable IBF device in accordance with the present technology can include patient-specific endplates that can achieve optimal surface area contact and/or provide a mechanism to tailor the medical intervention from the IBF device (e.g., tailor the segmental height restoration, the lordotic correction, and/or the coronal correction). In some embodiments, the patient-specific endplates are the result of additive and/or subtractive manufacturing. The patient-specific endplates can then be connected to an expandable mechanism that can also provide a predetermined height restoration, lordotic correction and/or coronal correction via one or more expansion mechanisms (e.g., an expandable jack, scissors jack mechanism, screw drive mechanism, etc.). In some such embodiments, the expansion mechanism includes one or more joints (e.g., ball joints), hinges, or other connections that can be precisely adjusted to a predetermined angle and then temporarily or permanently locked.

In an example embodiment, the IBF device includes an expansion mechanism configured to be locked at a desired expansion configuration to facilitate the fusion. The expansion mechanism can include a first lockable ball joint on an upper surface of the mechanism and a second lockable ball joint on a lower surface of the mechanism. The IBF device also includes a first endplate connected to the mechanism at the first lockable ball joint. In some embodiments, the first endplate includes a superior surface having one or more patient-specific features configured to engage and mate with the topology of an inferior surface of the superior vertebra. The IBF device also includes a second endplate connected to the mechanism at the second lockable ball joint. In some embodiments, the second endplate includes an inferior surface having one or more patient-specific features configured to engage and mate with the topology of a superior surface of the inferior vertebra.

In some embodiments, the patient-specific features of the first and/or second endplates can improve the match between the IBF device and the vertebrae being fused, thereby increasing the traction of the IBF device at the joint. For example, the one or more patient-specific features can correspond to topographical features on the surfaces of the vertebrae at the vertebral joint to customize the fit of the first and second endplates. In some embodiments, the patient-specific features of the first and/or second endplates include one or more features that help facilitate a prescribed medical treatment. For example, the first and/or second endplates can include a slope that helps provide a lordotic and/or coronal correction to the patient's spine. In some embodiments, the expandable main body includes a screw jack mechanical expansion mechanism. In some embodiments the expandable main body includes a scissor jack mechanical expansion mechanism.

For ease of reference, patient-specific implants are sometimes described herein with reference to top and bottom, upper and lower, upwards and downwards, and/or horizontal plane, x-y plane, vertical, or z-direction relative to the spatial orientation of the embodiments shown in the figures. It is to be understood, however, that the patient-specific implants can be moved to, and used in, different spatial orientations without changing the structure and/or function of the disclosed embodiments of the present technology.

Further, although primarily discussed herein as a method for customizing intervertebral body fusion devices and the resulting IBF devices, one of skill in the art will understand that the scope of the invention is not so limited. For example, the patient-specific customization methods disclosed herein can also be used to customize implants for various other medical procedures, such as for insertion at another joint in a patient's body. Accordingly, the scope of the invention is not confined to any subset of embodiments, and is confined only by the limitations set out in the appended claims.

Figure 1B:
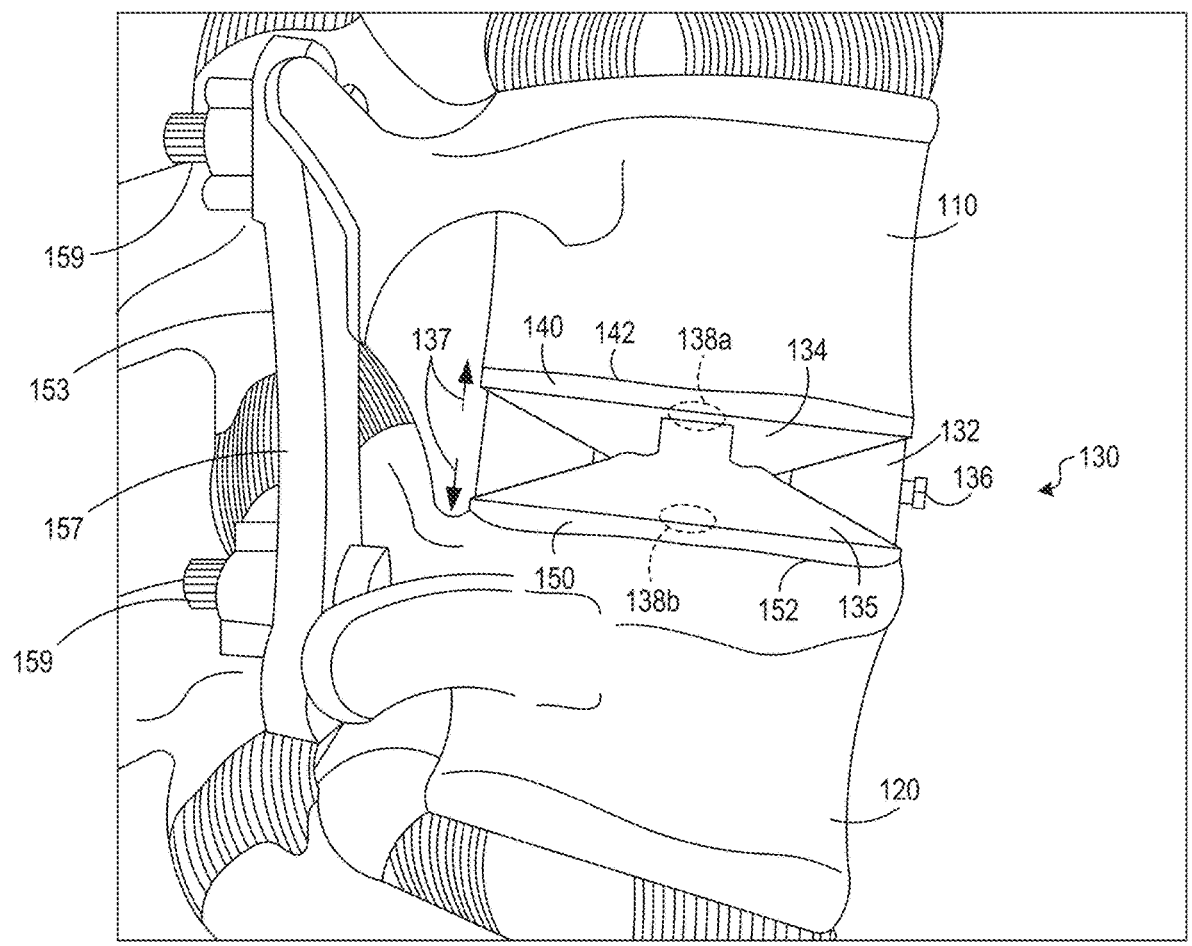

FIGS. 1A and 1B are schematic anterior and side illustrations, respectively, of a deployed patient-specific intervertebral body fusion device 130 ("device 130") deployed between a first vertebra 110 (e.g., a relatively superior vertebra) and a second vertebra 120 (e.g., a relatively inferior vertebra) in accordance with some embodiments of the present technology. The device 130 can be in a collapsed or low-profile configuration for delivery to the disc space between the first and second vertebrae 110, 120. For example, the collapsed device 130 can be inserted manually with surgical navigation or via a surgical robot and then expanded at the implantation site. Once deployed, as described in more detail below, the device 130 can provide one or more adjustments, corrections (e.g., corrections to the alignment of the first and second vertebrae 110, 120, spinal segments, etc.), or the like. FIG. 1B shows the device 130 fully expanded along a vertical axis, indicated by arrows 137, to space apart the first and second vertebrae 110, 120. As discussed in more detail below, the device 130 can be contoured and/or otherwise customized to match the contours of the first and second vertebrae 110, 120.

An auxiliary implant 153 is also illustrated. In some embodiments, the auxiliary implant 153 is patient-specific and includes a rod 157 curved to provide spacing between vertebrae. Fasteners 159 can couple the rod 157 to the vertebrae. Auxiliary patient-specific implants can include, without limitation, rod and screw systems, interspinous spacers, or other orthopedic implants. In some embodiments, the device 130 can also be used with non-patient-specific devices and implants. The auxiliary implant 153 can be designed based on, for example, the design of the device 130. For example, a simulation of one or more corrections to the spine based on implantation of the device 130 can be generated. The simulation can be performed using, for example, one or more virtual simulations using virtual three-dimensional models (e.g., CAD models) of the patient spine. The virtual simulations can include, for example, static loading simulations, dynamic motion simulations, disease progression simulations, range of motion simulations, or combinations thereof. In some implementations, the auxiliary implant 153 can be designed based on, for example, one or more targeted anatomical corrections, predicted spinal configurations, or the like. In some implementations, the auxiliary implant 153 can be designed to match the corrected configuration of the spine achieved by the device 130 such that the auxiliary implant 153 helps hold vertebrae in the corrected configuration following implantation of the device 130. In some simulations, devices can be iteratively redesigned using simulations until one or more design criteria are met.

In some implementations, the auxiliary implant 153 can contribute to spinal corrections. For example, a corrected anatomical configuration can be identified. The system can design the device 130 and auxiliary implant 153 to cooperate together to achieve the corrected anatomical configuration. That is, the device 130 and the auxiliary implant 153 together provide the corrected anatomical configuration. For example, the device 130 can be configured to primarily set the targeted disc height between adjacent vertebrae. The auxiliary implant 153 can be designed to, for example, lock repositioned (e.g., spaced apart by the expanded device 130) adjacent vertebrae together. Advantageously, the auxiliary implant 153 can be designed to fit along the patient's spine held in the corrected configuration by the device 130. In this manner, each patient specific component can contribute to a desired outcome.

As described in detail below with respect to FIGS. 2-7, the present technology further includes systems and methods for designing patient-specific implants and treatment programs. As described in greater below, such systems can determine the type and number of devices capable of contributing to a targeted overall correction. The system can then optimize the design of one, some, or all of the devices based on the targeted overall correction. The system can generate a surgical plan that includes, for example, a sequence of device implantation, implantation steps (e.g., instructions of implantation, identification of potential adverse events, etc.), or the like. The systems disclosed herein can design implants for implantation at different locations to provide a specific treatment. Exemplary intervertebral body fusion devices are discussed in connection with FIGS. 8A-24.

In the illustrated embodiment of FIG. 1A, the device 130 includes an expansion body or main body 131 operable to controllably expand or deploy the device 130. The main body 131 has a deployed or expanded configuration selected based on the treatment to be performed. The internal components of the main body 131 can be designed and manufactured to achieve a desired treatment plan. The patient-specific expansion can be selected based, at least in part, on the design of other components of the device 130. The device 130 can have a patient-specific design selected to, for example, enhance fusion (e.g., bone growth to the vertebral bodies), enhance fixation between the vertebral bodies, limit stresses in the vertebral bodies, or the like. For example, the device 130 can have a volume or receiving window 145 for receiving material, such as material that promotes both bone ingrowth.

The main body 131 can be configured to expand from a collapsed configuration to an expanded configuration (illustrated in FIGS. 1A and 1B) and can include one or more expansion mechanisms (e.g., screw jack mechanisms, wedges, scissors mechanisms, etc.), angled or sloped surfaces, inflatable members, or other components for causing deployment. Additionally, the main body 131 can include linkages, pin connections, linkage assemblies, or other components for connecting various other components. In some embodiments, the device 130 includes a drive feature 136 (e.g., a drive head, a screw head, a bolt head, etc.) coupleable to a drive instrument. The drive feature 136 can be connected to one or more drive elements (e.g., threaded bodies, wedge members, drive shafts, etc.) of the device 130. In some embodiments, the drive feature 136 can be rotated in opposite directions to controllably expand or collapse the device 130. The main body 131 can include an outer covering or bellows 139 that surrounds internal movable components. In other embodiments, the internal moving components can be exposed to the surrounding environment and upper and lower components 134, 135 can inhibit or limit movement of tissue between components of the main body 131.

As further illustrated in FIGS. 1A and 1B, the device 130 can further include a first endplate 140 (e.g., a superior endplate) and a lockable joint 138a connecting the first endplate 140 to the main body 131. The device 130 can further include a second endplate 150 (e.g., an inferior endplate) connected to the main body 131 via a lockable joint 138b. The lockable joints 138a, 138b can be selectively transitioned between an unlocked configuration and a locked configuration. In the unlocked configuration, the lockable joints 138a, 138b enable the first endplate 140 and the second endplate 150 to move relative to the main body 131. In the locked configuration, the lockable joints 138a, 138b prevent or at least reduce the first endplate 140 and the second endplate 150 from moving relative to the main body. Accordingly, in the unlocked configuration, the lockable joints 138a, 138b can be configured to provide a desired range of motion that permits the endplates 140, 150 to conform to patient anatomy. In some embodiments, the lockable joints 138a, 138b are ball joints, hinges, tethers, or other connections that allow relative movement between the endplates 140, 150. The lockable joints 138a, 138b can be connected to opposite ends of the main body 131 such that the lockable joints 138a, 138b are moved along with the respective endplates 140, 150, respectively, during expansion of the device 130. In some embodiments, the maximum range of motion of the lockable joints 138a, 138b is selected based on a desired range of motion for the spinal segment. In some embodiments, the position, configuration, and/or motion provided by the lockable joints 138a, 138b after locking can be selected based on the desired range of motion. Example connections and joints are discussed in more detail in connection with FIGS. 21-24.

The first endplate 140 includes a first surface 142 (e.g., a superior surface) that mates with an inferior surface 112 of the first vertebra, and a second surface 144 (e.g., an inferior surface) that mates with the lockable joint 138a and/or the upper component 134. Further, as illustrated in FIGS. 1A and 1B, the first surface 142 is customized to the patient-specific topology of the inferior vertebral surface 112 of the first vertebra 110. For example, as illustrated with respect to FIG. 1A, the inferior vertebral surface 112 can include patient-specific feature 114, such as the illustrated recessed region, valley, or divot. A flat endplate that was not customized to the patient-specific topology of the inferior vertebral surface 112 would result in a gap 162 at the patient-specific feature 114 (i.e., the gap 162 where the first endplate 140 does not contact the first vertebra 110). However, in the illustrated embodiment, the contoured first surface 142 matches the inferior vertebral surface 112 to increase the area of contact, thereby limiting or reducing stresses, such as stresses in the first vertebra 110 and/or the device 130. Further, as a result of the more complete contact made by the first endplate 140, the device 130 is expected have more optimal surface area contact with the first vertebra 110 to improve the traction of the device 130 and/or improve the expected outcome for a medical treatment using the device 130.

The contoured first surface 142 of the device 130 can also reduce or limit motion between the first vertebra 110 and the device 130. The reduced motion can help reduce spinal fusion time. In some embodiments, the contoured first surface 142 can have a thickened or protruding region that is substantially geometrically concurrent to the patient-specific feature 114 along the inferior vertebral surface 112. This further helps the endplate 140 to seat against the first vertebra 110. When an axial load is applied to device 130, the customized mating at the interface can limit, reduce, or substantially prevent relative movement between device 130 and the first vertebra 110. In some procedures, the device 130 can be configured to provide a generally gapless interface when the device 130 is in a fully expanded, implanted configuration.

Similarly, the second endplate 150 includes a first surface 152 (e.g., an inferior surface) that mates with a superior surface 122 of the second vertebra 120 and a second surface 154 (e.g., a superior surface) that mates with the lockable joint 138b and/or the lower component 135. Further, as illustrated in FIGS. 1A and 1B, the first surface 152 is customized to the patient-specific topology of the superior surface 122 of the second vertebra 120. For example, as illustrated with respect to FIG. 1A, the superior surface 122 can include multiple patient-specific features 124, such as the illustrated valleys or divots. As described above with respect to the patient-specific feature 114 of the first vertebra 110, an endplate that was not customized to the patient-specific topology of the superior surface 122 would accordingly include one or more gaps 164 corresponding to the patient-specific features 124 where the second endplate 150 does not contact the second vertebra 120. In contrast, the patient-specific topology of the second endplate 152 can be contoured to occupy the gap 164 and therefore contact the superior surface 122 of the second vertebra 120 at the patient-specific features 124. As a result of the more complete contact made by the second endplate 150, the device 130 is expected have more optimal surface area contact with the second vertebra 120 to improve the traction of the device 130 and/or improve the expected outcome for a medical treatment using the device 130.

In some embodiments, the first and second endplates 140, 150 can additionally, or alternatively, be customized to a medical treatment prescribed for the patient. In some embodiments, the first and second endplates 140, 150 are configured to help provide a height restoration, lordotic correction, and/or coronal correction. For example, the first and second endplates 140, 150 can vary in thickness in an x-y plane (e.g., thereby containing a slope) to help provide the lordotic and/or coronal corrections. In some embodiments, the height restoration, lordotic correction, and/or coronal correction provided by the first and second endplates 140, 150 can be patient-specific (e.g., based on the amount of prescribed corrections and/or factors specific to the patient, described in more detail below).

In some embodiments, the first and second endplates 140, 150 can additionally, or alternatively, be customized to account for load bearing strengths, toughness, fatigue characteristics, or properties that may vary along the endplates 140, 150. For example, the first and second endplates 140, 150 can compensate for strong and/or weak zones identified in the first and second vertebrae 110, 120 that are specific to the patient. In some embodiments, the first and second endplates 140, 150 can be configured to apply more force to identified strong or high load bearing zones (e.g., zones comprising bone or tissue with a relative high yield strength, fracture toughness, etc.) in the first and second vertebrae 110, 120 and/or apply less force (or no force) to identified weak zones (e.g., zones comprising bone or tissue with a relative low yield strength, fracture toughness, etc.).

In some embodiments, the first and second endplates 140, 150 can additionally, or alternatively, be customized to achieve a desired fit. The desired fit can be designed to, for example, reduce motion between the device 130 and the vertebral bodies, facilitate seating during the implantation procedure, increase friction, or the like. The first and second endplates 140, 150 can include anchors, texturing, protrusions, or other suitable elements selected to provide the desired fit. Configurations and different fits are discussed in connection with the spinal segments of FIGS. 10A-10D.

In addition to (or in alternative to) the patient-specific features of the first and second endplates 140, 150, the device 130 can be configured to provide a precise, predetermined height restoration, lordosis angle correction, and/or coronal angle correction. In some embodiments, the device 130 can be intraoperatively adjusted. For example, a surgical instrument can be connected to the first and second endplates 140, 150 to intraoperatively adjust the lockable joints 138 until a predetermined lordotic and/or coronal segmental correction is provided by the slope of the first and second endplates 140, 150, then the lockable joints 138 can be locked. In another example, a surgical instrument can be intraoperatively connected to the drive feature 136 of the device 130 to expand the device 130 until a predetermined height restoration is achieved. Once the predetermined height restoration is achieved, the device 130 can be locked at the configuration that provides the predetermined height restoration. In some embodiments, the device 130 is pre-operatively adjusted and locked, then inserted to achieve the predetermined correction. In some embodiments, one or more components of the device 130 are pre-operatively adjusted and locked while other components are intraoperatively adjusted. For example, in some embodiments, the lockable joints 138a, 138b can be pre-operatively adjusted and locked to achieve the predetermined angulation of the first and second endplates 140, 150, while the device 130 is expanded in-situ to provide the predetermined height restoration.

In some intraoperative embodiments, the device 130 is inserted and adjusted to achieve the optimal height and angular correction under surgical navigation guidance. For example, a surgical instrument can be used to monitor the expansion and/or angular correction of the device 130. In some embodiments, the device 130 includes lockable mechanical and/or electrical stoppers (not shown) that can be pre-operatively set to stop the expansion and/or angle correction at predetermined points. For example, the device 130 can include a lockable mechanical mechanism that prevents the device 130 from expanding past the predetermined height restoration. In these embodiments, the intraoperative adjustments can be accurately adjusted to the predetermined configuration without additional surgical instrumentation by adjusting until the lockable stoppers prevent further adjustment.

Without being bound by theory, the device 130 is expected to provide several advantages over conventional IBF devices. First, the device 130 can be configured for two types of adjustments: (1) increasing the space/distance between the first endplate 140 and the second endplate 150 (e.g., expansion), such as to restore appropriate intervertebral spacing, and (2) selectively and independently changing the angle of the first endplate 140 and the second endplate 150 relative to the main body 131 via manipulation of the lockable joints 138a, 138b, such as to restore appropriate intervertebral alignment. Second, as set forth in detail above, the device 130 is designed with patient-specific features that are expected to improve performance of the device by improving fit, optimizing load-bearing regions, reducing the likelihood of an overcorrection, or the like. Of course, other advantages of the device 130 and the present technology will be apparent to those skilled in the art based on this Detailed Description and the Figures. The present technology is therefore not limited by the foregoing advantages.

As one skilled in the art will appreciate from the disclosure herein, the device 130 is provided as a simple schematic example of a patient-specific IBF device. Because the patient-specific implants described herein are designed to match individual patient anatomy, the size, shape, and geometry of the patient-specific implant will vary according to individual patient anatomy. The present technology is thus not limited to any particular IBF device or implant design and can therefore include other implants beyond those illustrated or described herein, including replacements for other discs or joints not expressly described herein.

Systems For Designing and Manufacturing of Implants

Figure 2:
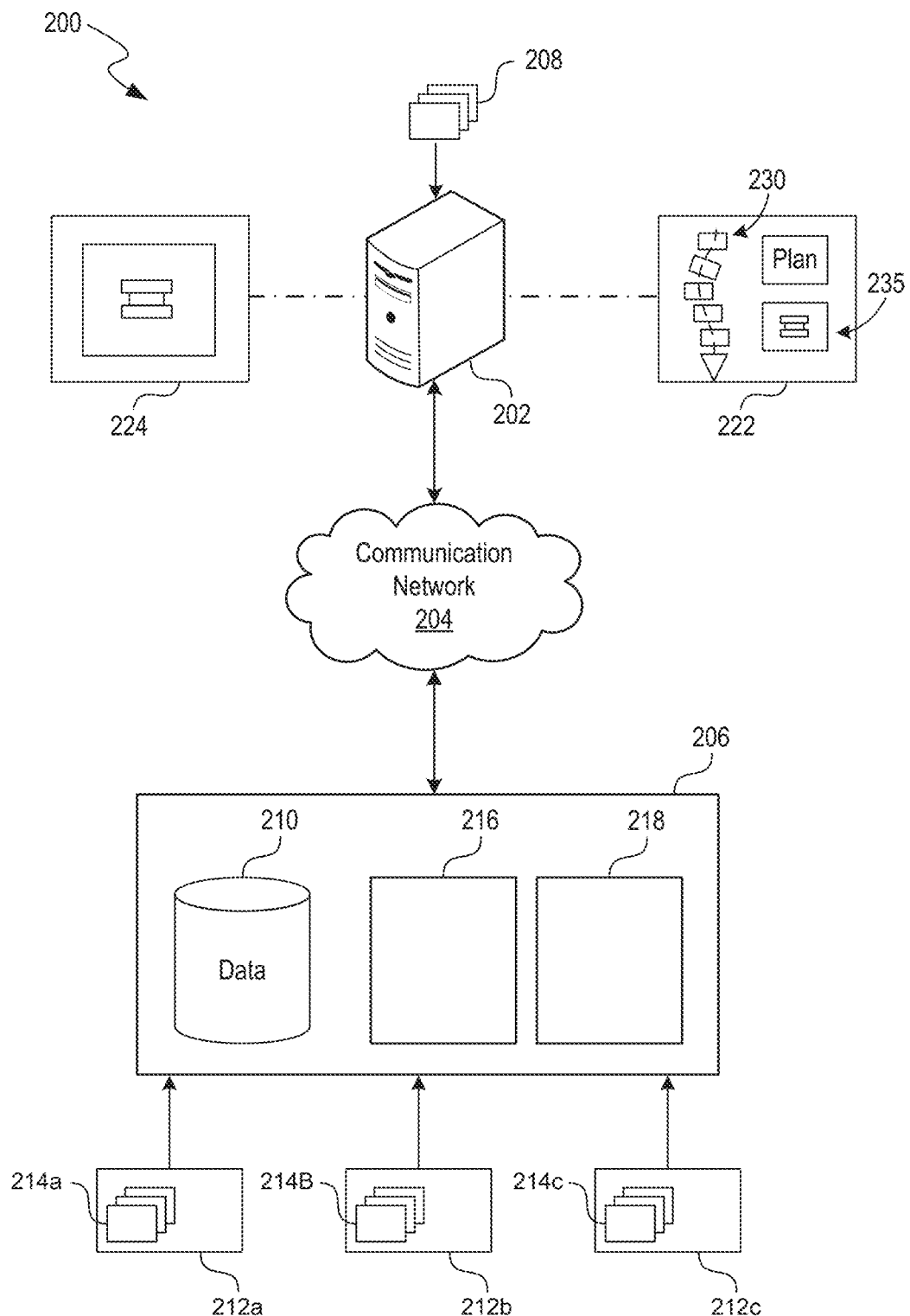
FIG. 2 is a network connection diagram illustrating a computing system for providing patient-specific medical care according to embodiments of the present technology.

The present technology further includes systems for designing and manufacturing patient-specific implants, such as the device 130 described above with respect to FIGS. 1A and 1B. For example, FIG. 2 is a network connection diagram illustrating a computing system 200 for providing patient-specific medical care, according to some embodiments of the present technology. As described in further detail herein, the system 200 is configured to generate a medical treatment plan for a patient. In some embodiments, the system 200 is configured to generate a medical treatment plan for a patient suffering from an orthopedic or spinal disease or disorder, such as trauma (e.g., fractures), cancer, deformity, degeneration, pain (e.g., back pain, leg pain), irregular spinal curvature (e.g., scoliosis, lordosis, kyphosis), irregular spinal displacement (e.g., spondylolisthesis, lateral displacement axial displacement), osteoarthritis, lumbar degenerative disc disease, cervical degenerative disc disease, lumbar spinal stenosis, or cervical spinal stenosis, or a combination thereof. The medical treatment plan can include surgical information, surgical plans, technology recommendations (e.g., device and/or instrument recommendations), and/or medical device designs. For example, the medical treatment plan can include at least one treatment procedure (e.g., a surgical procedure or intervention) and/or at least one medical device (e.g., an implanted medical device (also referred to herein as an "implant" or "implanted device") or implant delivery instrument).

In some embodiments, the system 200 generates a medical treatment plan that is customized for a particular patient or group of patients, also referred to herein as a "patient-specific" or "personalized" treatment plan. The patient-specific treatment plan can include at least one patient-specific surgical procedure and/or at least one patient-specific medical device that are designed and/or optimized for the patient's particular characteristics (e.g., condition, anatomy, pathology, condition, medical history). For example, the patient-specific medical device can be designed and manufactured specifically for the particular patient, rather than being an off-the-shelf device. However, it shall be appreciated that a patient-specific treatment plan can also include aspects that are not customized for the particular patient. For example, a patient-specific or personalized surgical procedure can include one or more instructions, portions, steps, etc. that are non-patient-specific. Likewise, a patient-specific or personalized medical device can include one or more components that are non-patient-specific, and/or can be used with an instrument or tool that is non-patient-specific. Personalized implant designs can be used to manufacture or select patient-specific technologies, including medical devices, instruments, and/or surgical kits. For example, a personalized surgical kit can include one or more patient-specific devices, patient-specific instruments, non-patient-specific technology (e.g., standard instruments, devices, etc.), instructions for use, patient-specific treatment plan information, or a combination thereof.

The system 200 includes a client computing device 202, which can be a user device, such as a smart phone, mobile device, laptop, desktop, personal computer, tablet, phablet, or other such devices known in the art. As discussed further herein, the client computing device 202 can include one or more processors, and memory storing instructions executable by the one or more processors to perform the methods described herein. The client computing device 202 can be associated with a healthcare provider that is treating the patient. Although FIG. 2 illustrates a single client computing device 202, in alternative embodiments, the client computing device 202 can instead be implemented as a client computing system encompassing a plurality of computing devices, such that the operations described herein with respect to the client computing device 202 can instead be performed by the computing system and/or the plurality of computing devices.

The client computing device 202 is configured to receive a patient data set 208 associated with a patient to be treated. The patient data set 208 can include data representative of the patient's condition, anatomy, pathology, medical history, preferences, and/or any other information or parameters relevant to the patient. For example, the patient data set 208 can include medical history, surgical intervention data, treatment outcome data, progress data (e.g., physician notes), patient feedback (e.g., feedback acquired using quality of life questionnaires, surveys), clinical data, provider information (e.g., physician, hospital, surgical team), patient information (e.g., demographics, sex, age, height, weight, type of pathology, occupation, activity level, tissue information, health rating, comorbidities, health related quality of life (HRQL)), vital signs, diagnostic results, medication information, allergies, image data (e.g., camera images, Magnetic Resonance Imaging (MRI) images, ultrasound images, Computerized Aided Tomography (CAT) scan images, Positron Emission Tomography (PET) images, X-Ray images), diagnostic equipment information (e.g., manufacturer, model number, specifications, user-selected settings/configurations, etc.), or the like. In some embodiments, the patient data set 208 includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine.

The client computing device 202 is operably connected via a communication network 204 to a server 206, thus allowing for data transfer between the client computing device 202 and the server 206. The communication network 204 may be a wired and/or a wireless network. The communication network 204, if wireless, may be implemented using communication techniques such as Visible Light Communication (VLC), Worldwide Interoperability for Microwave Access (WiMAX), Long term evolution (LTE), Wireless local area network (WLAN), Infrared (IR) communication, Public Switched Telephone Network (PSTN), Radio waves, and/or other communication techniques known in the art.

The server 206, which may also be referred to as a "treatment assistance network" or "prescriptive analytics network," can include one or more computing devices and/or systems. As discussed further herein, the server 206 can include one or more processors, and memory storing instructions executable by the one or more processors to perform the methods described herein. In some embodiments, the server 206 is implemented as a distributed "cloud" computing system or facility across any suitable combination of hardware and/or virtual computing resources.

The client computing device 202 and server 206 can individually or collectively perform the various methods described herein for providing patient-specific medical care. For example, some or all of the steps of the methods described herein can be performed by the client computing device 202 alone, the server 206 alone, or a combination of the client computing device 202 and the server 206. Thus, although certain operations are described herein with respect to the server 206, it shall be appreciated that these operations can also be performed by the client computing device 202, and vice-versa.

The server 206 includes at least one database 210 configured to store reference data useful for the treatment planning methods described herein. The reference data can include historical and/or clinical data from the same or other patients, data collected from prior surgeries and/or other treatments of patients by the same or other healthcare providers, data relating to medical device designs, data collected from study groups or research groups, data from practice databases, data from academic institutions, data from implant manufacturers or other medical device manufacturers, data from imaging studies, data from simulations, clinical trials, demographic data, treatment data, outcome data, mortality rates, or the like.

In some embodiments, the database 210 includes a plurality of reference patient data sets, each patient reference data set associated with a corresponding reference patient. For example, the reference patient can be a patient that previously received treatment or is currently receiving treatment. Each reference patient data set can include data representative of the corresponding reference patient's condition, anatomy, pathology, medical history, disease progression, preferences, and/or any other information or parameters relevant to the reference patient, such as any of the data described herein with respect to the patient data set 208. In some embodiments, the reference patient data set includes pre-operative data, intra-operative data, and/or post-operative data. For example, a reference patient data set can include data representing one or more of patient ID, age, gender, BMI, lumbar lordosis, Cobb angle(s), pelvic incidence, disc height, segment flexibility, bone quality, rotational displacement, and/or treatment level of the spine. As another example, a reference patient data set can include treatment data regarding at least one treatment procedure performed on the reference patient, such as descriptions of surgical procedures or interventions (e.g., surgical approaches, bony resections, surgical maneuvers, corrective maneuvers, placement of implants or other devices). In some embodiments, the treatment data includes medical device design data for at least one medical device used to treat the reference patient, such as physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties). In yet another example, a reference patient data set can include outcome data representing an outcome of the treatment of the reference patient, such as corrected anatomical metrics, presence of fusion, HRQL, activity level, return to work, complications, recovery times, efficacy, mortality, and/or follow-up surgeries.

In some embodiments, the server 206 receives at least some of the reference patient data sets from a plurality of healthcare provider computing systems (e.g., systems 212a-212c, collectively 212). The server 206 can be connected to the healthcare provider computing systems 212 via one or more communication networks (not shown). Each healthcare provider computing system 212 can be associated with a corresponding healthcare provider (e.g., physician, surgeon, medical clinic, hospital, healthcare network, etc.). Each healthcare provider computing system 212 can include at least one reference patient data set (e.g., reference patient data sets 214a-214c, collectively 214) associated with reference patients treated by the corresponding healthcare provider. The reference patient data sets 214 can include, for example, electronic medical records, electronic health records, biomedical data sets, etc. The reference patient data sets 214 can be received by the server 206 from the healthcare provider computing systems 212 and can be reformatted into different formats for storage in the database 210. Optionally, the reference patient data sets 214 can be processed (e.g., cleaned) to ensure that the represented patient parameters are likely to be useful in the treatment planning methods described herein.

As described in further detail herein, the server 206 can be configured with one or more algorithms that generate patient-specific treatment plan data (e.g., treatment procedures, medical devices) based on the reference data. In some embodiments, the patient-specific data is generated based on correlations between the patient data set 208 and the reference data. Optionally, the server 206 can predict outcomes, including recovery times, efficacy based on clinical end points, likelihood of success, predicted mortality, predicted related follow-up surgeries, or the like. In some embodiments, the server 206 can continuously or periodically analyze patient data (including patient data obtained during the patient stay) to determine near real-time or real-time risk scores, mortality prediction, etc.

In some embodiments, the server 206 includes one or more modules for performing one or more steps of the patient-specific treatment planning methods described herein. For example, in the depicted embodiment, the server 206 includes a data analysis module 216 and a treatment planning module 218. In alternative embodiments, one or more of these modules may be combined with each other, or may be omitted. Thus, although certain operations are described herein with respect to a particular module or modules, this is not intended to be limiting, and such operations can be performed by a different module or modules in alternative embodiments.

The data analysis module 216 is configured with one or more algorithms for identifying a subset of reference data from the database 210 that is likely to be useful in developing a patient-specific treatment plan. For example, the data analysis module 216 can compare patient-specific data (e.g., the patient data set 208 received from the client computing device 202) to the reference data from the database 210 (e.g., the reference patient data sets) to identify similar data (e.g., one or more similar patient data sets in the reference patient data sets). The comparison can be based on one or more parameters, such as age, gender, BMI, lumbar lordosis, pelvic incidence, and/or treatment levels. The parameter(s) can be used to calculate a similarity score for each reference patient. The similarity score can represent a statistical correlation between the patient data set 208 and the reference patient data set. Accordingly, similar patients can be identified based on whether the similarity score is above, below, or at a specified threshold value. For example, as described in greater detail below, the comparison can be performed by assigning values to each parameter and determining the aggregate difference between the subject patient and each reference patient. Reference patients whose aggregate difference are below a threshold can be considered to be similar patients.

The data analysis module 216 can further be configured with one or more algorithms to select a subset of the reference patient data sets, e.g., based on similarity to the patient data set 208 and/or treatment outcome of the corresponding reference patient. For example, the data analysis module 216 can identify one or more similar patient data sets in the reference patient data sets, and then select a subset of the similar patient data sets based on whether the similar patient data set includes data indicative of a favorable or desired treatment outcome. The outcome data can include data representing one or more outcome parameters, such as corrected anatomical metrics, presence of fusion, HRQL, activity level, complications, recovery times, efficacy, mortality, or follow-up surgeries. As described in further detail below, in some embodiments, the data analysis module 216 calculates an outcome score by assigning values to each outcome parameter. A patient can be considered to have a favorable outcome if the outcome score is above, below, or at a specified threshold value.

In some embodiments, the data analysis module 216 selects a subset of the reference patient data sets based at least in part on user input (e.g., from a clinician, surgeon, physician, healthcare provider). For example, the user input can be used in identifying similar patient data sets. In some embodiments, weighting of similarity and/or outcome parameters can be selected by a healthcare provider or physician to adjust the similarity and/or outcome score based on clinician input. In further embodiments, the healthcare provider or physician can select the set of similarity and/or outcome parameters (or define new similarity and/or outcome parameters) used to generate the similarity and/or outcome score, respectively.

In some embodiments, the data analysis module 216 includes one or more algorithms used to select a set or subset of the reference patient data sets based on criteria other than patient parameters. For example, the one or more algorithms can be used to select the subset based on healthcare provider parameters (e.g., based on healthcare provider ranking/scores such as hospital/physician expertise, number of procedures performed, hospital ranking, etc.) and/or healthcare resource parameters (e.g., diagnostic equipment, facilities, surgical equipment such as surgical robots), or other non-patient related information that can be used to predict outcomes and risk profiles for procedures for the present healthcare provider. For example, reference patient data sets with images captured from similar diagnostic equipment can be aggregated to reduce or limit irregularities due to variation between diagnostic equipment. Additionally, patient-specific treatment plans can be developed for a particular health-care provider using data from similar healthcare providers (e.g., healthcare providers with traditionally similar outcomes, physician expertise, surgical teams, etc.). In some embodiments, reference healthcare provider data sets, hospital data sets, physician data sets, surgical team data sets, post-treatment data set, and other data sets can be utilized. By way of example, a patient-specific treatment plan to perform a battlefield surgery can be based on reference patient data from similar battlefield surgeries and/or datasets associated with battlefield surgeries. In another example, the patient-specific treatment plan can be generated based on available robotic surgical systems. The reference patient data sets can be selected based on patients that have been operated on using comparable robotic surgical systems under similar conditions (e.g., size and capabilities of surgical teams, hospital resources, etc.).

The treatment planning module 218 is configured with one or more algorithms to generate at least one treatment plan (e.g., pre-operative plans, surgical plans, post-operative plans etc.) based on the output from the data analysis module 216. In some embodiments, the treatment planning module 218 is configured to develop and/or implement at least one predictive model for generating the patient-specific treatment plan, also known as a "prescriptive model." The predictive model(s) can be developed using clinical knowledge, statistics, machine learning, AI, neural networks, or the like. In some embodiments, the output from the data analysis module 216 is analyzed (e.g., using statistics, machine learning, neural networks, AI) to identify correlations between data sets, patient parameters, healthcare provider parameters, healthcare resource parameters, treatment procedures, medical device designs, and/or treatment outcomes. These correlations can be used to develop at least one predictive model that predicts the likelihood that a treatment plan will produce a favorable outcome for the particular patient. The predictive model(s) can be validated, e.g., by inputting data into the model(s) and comparing the output of the model to the expected output.

In some embodiments, the treatment planning module 218 is configured to generate the treatment plan based on previous treatment data from reference patients. For example, the treatment planning module 218 can receive a selected subset of reference patient data sets and/or similar patient data sets from the data analysis module 216, and determine or identify treatment data from the selected subset. The treatment data can include, for example, treatment procedure data (e.g., surgical procedure or intervention data) and/or medical device design data (e.g., implant design data) that are associated with favorable or desired treatment outcomes for the corresponding patient. The treatment planning module 218 can analyze the treatment procedure data and/or medical device design data to determine an optimal treatment protocol for the patient to be treated. For example, the treatment procedures and/or medical device designs can be assigned values and aggregated to produce a treatment score. The patient-specific treatment plan can be determined by selecting treatment plan(s) based on the score (e.g., higher or highest score; lower or lowest score; score that is above, below, or at a specified threshold value). The personalized patient-specific treatment plan can be based on, at least in part, the patient-specific technologies or patient-specific selected technology.

Alternatively or in combination, the treatment planning module 218 can generate the treatment plan based on correlations between data sets. For example, the treatment planning module 218 can correlate treatment procedure data and/or medical device design data from similar patients with favorable outcomes (e.g., as identified by the data analysis module 216). Correlation analysis can include transforming correlation coefficient values to values or scores. The values/scores can be aggregated, filtered, or otherwise analyzed to determine one or more statistical significances. These correlations can be used to determine treatment procedure(s) and/or medical device design(s) that are optimal or likely to produce a favorable outcome for the patient to be treated.

Alternatively or in combination, the treatment planning module 218 can generate the treatment plan using one or more AI techniques. AI techniques can be used to develop computing systems capable of simulating aspects of human intelligence, e.g., learning, reasoning, planning, problem solving, decision making, etc. AI techniques can include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems.

In some embodiments, the treatment planning module 218 generates the treatment plan using one or more trained machine learning models. Various types of machine learning models, algorithms, and techniques are suitable for use with the present technology. In some embodiments, the machine learning model is initially trained on a training data set, which is a set of examples used to fit the parameters (e.g., weights of connections between "neurons" in artificial neural networks) of the model. For example, the training data set can include any of the reference data stored in database 210, such as a plurality of reference patient data sets or a selected subset thereof (e.g., a plurality of similar patient data sets).

In some embodiments, the machine learning model (e.g., a neural network or a naïve Bayes classifier) may be trained on the training data set using a supervised learning method (e.g., gradient descent or stochastic gradient descent). The training dataset can include pairs of generated "input vectors" with the associated corresponding "answer vector" (commonly denoted as the target). The current model is run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some embodiments, the error of the validation data set error can fluctuate during training, such that ad-hoc rules may be used to decide when overfitting has truly begun. Finally, a test data set can be used to provide an unbiased evaluation of a final model fit on the training data set.

To generate a treatment plan, the patient data set 208 can be input into the trained machine learning model(s). Additional data, such as the selected subset of reference patient data sets and/or similar patient data sets, and/or treatment data from the selected subset, can also be input into the trained machine learning model(s). The trained machine learning model(s) can then calculate whether various candidate treatment procedures and/or medical device designs are likely to produce a favorable outcome for the patient. Based on these calculations, the trained machine learning model(s) can select at least one treatment plan for the patient. In embodiments where multiple trained machine learning models are used, the models can be run sequentially or concurrently to compare outcomes and can be periodically updated using training data sets. The treatment planning module 218 can use one or more of the machine learning models based the model's predicted accuracy score.

The patient-specific treatment plan generated by the treatment planning module 218 can include at least one patient-specific treatment procedure (e.g., a surgical procedure or intervention, such as the surgical procedures described with reference to the device 130 of FIGS. 1A and 1B) and/or at least one patient-specific medical device (e.g., an implant or implant delivery instrument, such as the device 130 described with reference to FIGS. 1A and 1B). A patient-specific treatment plan can include an entire surgical procedure or portions thereof. Additionally, one or more patient-specific medical devices can be specifically selected or designed for the corresponding surgical procedure, thus allowing for the various components of the patient-specific technology to be used in combination to treat the patient.

In some embodiments, the patient-specific treatment procedure includes an orthopedic surgery procedure, such as spinal surgery, hip surgery, knee surgery, jaw surgery, hand surgery, shoulder surgery, elbow surgery, total joint reconstruction (arthroplasty), skull reconstruction, foot surgery, or ankle surgery. Spinal surgery can include spinal fusion surgery, such as posterior lumbar interbody fusion (PLIF), anterior lumbar interbody fusion (ALIF), transverse or transforaminal lumbar interbody fusion (TLIF), lateral lumbar interbody fusion (LLIF), direct lateral lumbar interbody fusion (DLIF), or extreme lateral lumbar interbody fusion (XLIF). In some embodiments, the patient-specific treatment procedure includes descriptions of and/or instructions for performing one or more aspects of a patient-specific surgical procedure. For example, the patient-specific surgical procedure can include one or more of a surgical approach, a corrective maneuver, a bony resection, or implant placement.

In some embodiments, the patient-specific medical device design includes a design for an orthopedic implant and/or a design for an instrument for delivering an orthopedic implant. Examples of such implants include, but are not limited to, screws (e.g., bone screws, spinal screws, pedicle screws, facet screws), interbody implant devices (e.g., intervertebral implants), intervertebral body fusion ("IBF") devices, interspinous spacers, cages, plates, endplates, rods, disks, fusion devices, spacers, rods, expandable devices, stents, brackets, ties, scaffolds, fixation device, anchors, nuts, bolts, rivets, connectors, tethers, fasteners, joint replacements, hip implants, or the like. Examples of instruments include, but are not limited to, screw guides, cannulas, ports, catheters, insertion tools, decompression instruments, or the like.

A patient-specific medical device design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of a corresponding medical device. For example, a design for an orthopedic implant can include implant shape, size, material, and/or effective stiffness (e.g., lattice density, number of struts, location of struts, etc.). In some embodiments, the generated patient-specific medical device design is a design for an entire device. Alternatively, the generated design can be for one or more components of a device, rather than the entire device.

In some embodiments, the design is for one or more patient-specific device components that can be used with standard, off-the-shelf components. For example, in a spinal surgery, an IBF device can include both standard components and patient-specific customized components. In some embodiments, the generated design is for a patient-specific medical device that can be used with a standard, off-the-shelf delivery instrument. For example, the implants (e.g., endplates, expansion devices, screws) can be designed and manufactured for the patient, while the instruments for delivering the implants can be standard instruments. This approach allows the components that are implanted to be designed and manufactured based on the patient's anatomy and/or surgeon's preferences to enhance treatment. The patient-specific devices described herein are expected to improve delivery into the patient's body, placement at the treatment site, and/or interaction with the patient's anatomy.

In embodiments where the patient-specific treatment plan includes a surgical procedure to implant a medical device, the treatment planning module 218 can also store various types of implant surgery information, such as implant parameters (e.g., types, dimensions), availability of implants, aspects of a pre-operative plan (e.g., initial implant configuration, detection and measurement of the patient's anatomy, etc.), FDA requirements for implants (e.g., specific implant parameters and/or characteristics for compliance with FDA regulations), or the like. In some embodiments, the treatment planning module 218 can convert the implant surgery information into formats useable for machine-learning based models and algorithms. For example, the implant surgery information can be tagged with particular identifiers for formulas or can be converted into numerical representations suitable for supplying to the trained machine learning model(s). The treatment planning module 218 can also store information regarding the patient's anatomy, such as two- or three-dimensional images or models of the anatomy, and/or information regarding the biology, geometry, and/or mechanical properties of the anatomy. The anatomy information can be used to inform implant design and/or placement.

The treatment plan(s) generated by the treatment planning module 218 can be transmitted via the communication network 204 to the client computing device 202 for output to a user (e.g., clinician, surgeon, healthcare provider, patient). In some embodiments, the client computing device 202 includes or is operably coupled to a display 222 for outputting the treatment plan(s). The display 222 can include a graphical user interface (GUI) for visually depicting various aspects of the treatment plan(s). For example, the display 222 can show various aspects of a surgical procedure to be performed on the patient, such as the surgical approach, treatment levels, corrective maneuvers, tissue resection, and/or implant placement. To facilitate visualization, a virtual model of the surgical procedure can be displayed. As another example, the display 222 can show a design 235 for a medical device to be implanted in the patient, such as a two-or three-dimensional model of the device design 235. The display 222 can also show patient information, such as two-or three-dimensional images or models 230 of the patient's anatomy where the surgical procedure is to be performed and/or where the device is to be implanted. The client computing device 202 can further include one or more user input devices (not shown) allowing the user to modify, select, approve, and/or reject the displayed treatment plan(s).

In some embodiments, the medical device design(s) generated by the treatment planning module 218 can be transmitted from the client computing device 202 and/or server 206 to a manufacturing system 224 for manufacturing a corresponding medical device. The manufacturing system 224 can be located on site or off site. On-site manufacturing can reduce the number of sessions with a patient and/or the time to be able to perform the surgery whereas off-site manufacturing can be useful to make the complex devices. Off-site manufacturing facilities can have specialized manufacturing equipment. In some embodiments, more complicated device components can be manufactured off site, while simpler device components can be manufactured on site.

Various types of manufacturing systems are suitable for use in accordance with the embodiments herein. For example, the manufacturing system 224 can be configured for additive manufacturing, such as three-dimensional (3D) printing, stereolithography (SLA), digital light processing (DLP), fused deposition modeling (FDM), selective laser sintering (SLS), selective laser melting (SLM), selective heat sintering (SHM), electronic beam melting (EBM), laminated object manufacturing (LOM), powder bed printing (PP), thermoplastic printing, direct material deposition (DMD), inkjet photo resin printing, or like technologies, or combination thereof. Alternatively or in combination, the manufacturing system 224 can be configured for subtractive (traditional) manufacturing, such as CNC machining, electrical discharge machining (EDM), grinding, laser cutting, water jet machining, manual machining (e.g., milling, lathe/turning), or like technologies, or combinations thereof. The manufacturing system 224 can manufacture one or more patient-specific medical devices based on fabrication instructions or data (e.g., CAD data, 3D data, digital blueprints, stereolithography data, or other data suitable for the various manufacturing technologies described herein). Different components of the system 200 can generate at least a portion of the manufacturing data used by the manufacturing system 224. The manufacturing data can include, without limitation, fabrication instructions (e.g., programs executable by additive manufacturing equipment, subtractive manufacturing equipment, etc.), 3D data, CAD data (e.g., CAD files), CAM data (e.g., CAM files), path data (e.g., print head paths, tool paths, etc.), material data, tolerance data, surface finish data (e.g., surface roughness data), regulatory data (e.g., FDA requirements, reimbursement data, etc.), or the like. The manufacturing system 224 can analyze the manufacturability of the implant design based on the received manufacturing data. The implant design can be finalized by altering geometries, surfaces, etc. and then generating manufacturing instructions. In some embodiments, the server 206 generates at least a portion of the manufacturing data, which is transmitted to the manufacturing system 224.

The manufacturing system 224 can generate CAM data, print data (e.g., powder bed print data, thermoplastic print data, photo resin data, etc.), or the like and can include additive manufacturing equipment, subtractive manufacturing equipment, thermal processing equipment, or the like. The additive manufacturing equipment can be 3D printers, stereolithography devices, digital light processing devices, fused deposition modeling devices, selective laser sintering devices, selective laser melting devices, electronic beam melting devices, laminated object manufacturing devices, powder bed printers, thermoplastic printers, direct material deposition devices, or inkjet photo resin printers, or like technologies. The subtractive manufacturing equipment can be CNC machines, electrical discharge machines, grinders, laser cutters, water jet machines, manual machines (e.g., milling machines, lathes, etc.), or like technologies. Both additive and subtractive techniques can be used to produce implants with complex geometries, surface finishes, material properties, etc. The generated fabrication instructions can be configured to cause the manufacturing system 224 to manufacture the patient-specific orthopedic implant that matches or is therapeutically the same as the patient-specific design. In some embodiments, the patient-specific medical device can include features, materials, and designs shared across designs to simplify manufacturing. For example, deployable patient-specific medical devices for different patients can have similar internal deployment mechanisms but have different deployed configurations. In some embodiments, the components of the patient-specific medical devices are selected from a set of available pre-fabricated components and the selected pre-fabricated components can be modified based on the fabrication instructions or data.

The treatment plans described herein can be performed by a surgeon, a surgical robot, or a combination thereof, thus allowing for treatment flexibility. In some embodiments, the surgical procedure can be performed entirely by a surgeon, entirely by a surgical robot, or a combination thereof. For example, one step of a surgical procedure can be manually performed by a surgeon and another step of the procedure can be performed by a surgical robot. In some embodiments the treatment planning module 218 generates control instructions configured to cause a surgical robot (e.g., robotic surgery systems, navigation systems, etc.) to partially or fully perform a surgical procedure. The control instructions can be transmitted to the robotic apparatus by the client computing device 202 and/or the server 206.

Following the treatment of the patient in accordance with the treatment plan, treatment progress can be monitored over one or more time periods to update the data analysis module 216 and/or treatment planning module 218. Post-treatment data can be added to the reference data stored in the database 210. The post-treatment data can be used to train machine learning models for developing patient-specific treatment plans, patient-specific medical devices, or combinations thereof.

It shall be appreciated that the components of the system 200 can be configured in many different ways. For example, in alternative embodiments, the database 210, the data analysis module 216 and/or the treatment planning module 218 can be components of the client computing device 202, rather than the server 206. As another example, the database 210 the data analysis module 216, and/or the treatment planning module 218 can be located across a plurality of different servers, computing systems, or other types of cloud-computing resources, rather than at a single server 206 or client computing device 202.

Additionally, in some embodiments, the system 200 can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

Figure 3:
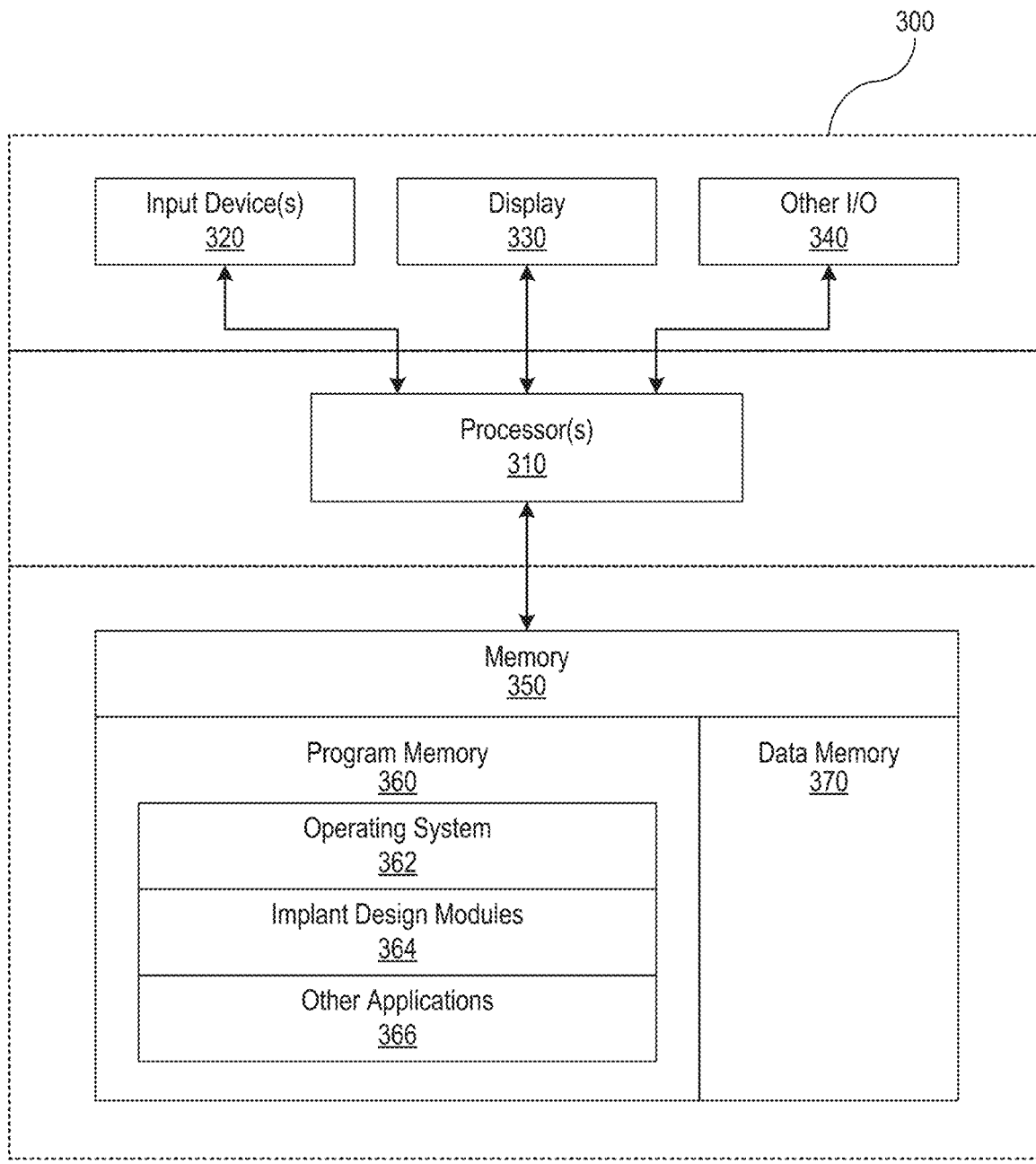
FIG. 3 illustrates a computing device suitable for use in connection with a system of the type illustrated in FIG. 2.

FIG. 3 illustrates a computing device 300 suitable for use in connection with the system 200 of FIG. 2 according to some embodiments of the present technology. The computing device 300 can be incorporated in various components of the system 200 of FIG. 1, such as the client computing device 202 or the server 206. The computing device 300 includes one or more processors 310 (e.g., CPU(s), GPU(s), HPU(s), etc.). The processor(s) 310 can be a single processing unit or multiple processing units in a device or distributed across multiple devices. The processor(s) 310 can be coupled to other hardware devices, for example, with the use of a bus, such as a PCI bus or SCSI bus. The processor(s) 310 can be configured to execute one more computer-readable program instructions, such as program instructions to carry out of any of the methods described herein.

The computing device 300 can include one or more input devices 320 that provide input to the processor(s) 310, e.g., to notify it of actions from a user of the device 300. The actions can be mediated by a hardware controller that interprets the signals received from the input device and communicates the information to the processor(s) 310 using a communication protocol. Input device(s) 320 can include, for example, a mouse, a keyboard, a touchscreen, an infrared sensor, a touchpad, a wearable input device, a camera- or image-based input device, a microphone, or other user input devices.

The computing device 300 can include a display 330 used to display various types of output, such as text, models, virtual procedures, surgical plans, implants, graphics, and/or images (e.g., images with voxels indicating radiodensity units or Hounsfield units representing the density of the tissue at a location). In some embodiments, the display 330 provides graphical and textual visual feedback to a user. The processor(s) 310 can communicate with the display 330 via a hardware controller for devices. In some embodiments, the display 330 includes the input device(s) 320 as part of the display 330, such as when the input device(s) 320 include a touchscreen or is equipped with an eye direction monitoring system. In alternative embodiments, the display 330 is separate from the input device(s) 320. Examples of display devices include an LCD display screen, an LED display screen, a projected, holographic, or augmented reality display (e.g., a heads-up display device or a head-mounted device), and so on.

Optionally, other I/O devices 340 can also be coupled to the processor(s) 310, such as a network card, video card, audio card, USB, firewire or other external device, camera, printer, speakers, CD-ROM drive, DVD drive, disk drive, or Blu-Ray device. Other I/O devices 340 can also include input ports for information from directly connected medical input equipment such as imaging apparatuses, including MRI machines, X-Ray machines, CT machines, etc. Other I/O devices 340 can further include input ports for receiving data from these types of machine from other sources, such as across a network or from previously captured data, for example, stored in a database.

In some embodiments, the computing device 300 also includes a communication device (not shown) capable of communicating wirelessly or wire-based with a network node. The communication device can communicate with another device or a server through a network using, for example, TCP/IP protocols. The computing device 300 can utilize the communication device to distribute operations across multiple network devices, including imaging equipment, manufacturing equipment, etc.

The computing device 300 can include memory 350, which can be in a single device or distributed across multiple devices. Memory 350 includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. In some embodiments, the memory 350 is a non-transitory computer-readable storage medium that stores, for example, programs, software, data, or the like. In some embodiments, memory 350 can include program memory 360 that stores programs and software, such as an operating system 362, one or more treatment assistance modules 364, and other application programs 366. The treatment assistance module(s) 364 can include one or more modules configured to perform the various methods described herein (e.g., the data analysis module 216 and/or treatment planning module 218 described with respect to FIG. 1). Memory 350 can also include data memory 370 that can include, e.g., reference data, configuration data, settings, user options or preferences, etc., which can be provided to the program memory 360 or any other element of the computing device 300.

Figure 4:
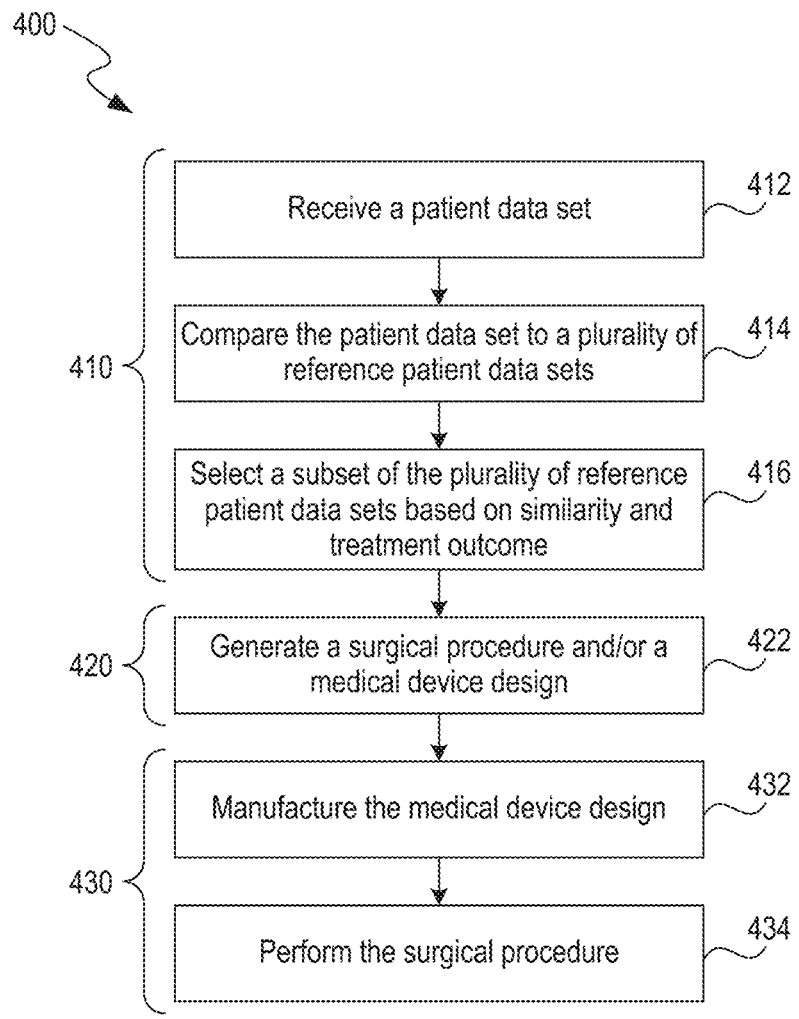
FIG. 4 is a flow diagram illustrating a method for providing patient-specific medical care in accordance with some embodiments of the present technology.

FIG. 4 is a flow diagram illustrating a method 400 for providing patient-specific medical care, according to an embodiment. The method 400 can include a data phase 410, a modeling phase 420, and an execution phase 430. The data phase 410 can include collecting data of a patient to be treated (e.g., pathology data), and comparing the patient data to reference data (e.g., prior patient data such as pathology, surgical, and/or outcome data). For example, a patient data set can be received (block 412). The patient data set can be compared to a plurality of reference patient data sets (block 414), e.g., in order to identify one or more similar patient data sets in the plurality of reference patient data sets. Each of the plurality of reference patient data sets can include data representing one or more of age, gender, BMI, lumbar lordosis, Cobb angle(s), pelvic incidence, disc height, segment flexibility, bone quality, rotational displacement, or treatment level of the spine.

A subset of the plurality of reference patient data sets can be selected (block 416), e.g., based on similarity to the patient data set and/or treatment outcomes of the corresponding reference patients. For example, a similarity score can be generated for each reference patient data set, based on the comparison of the patient data set and the reference patient data set. The similarity score can represent a statistical correlation between the patient data and the reference patient data set. One or more similar patient data sets can be identified based, at least partly, on the similarity score.

In some embodiments, each patient data set of the selected subset includes and/or is associated with data indicative of a favorable treatment outcome (e.g., a favorable treatment outcome based on a single target outcome, aggregate outcome score, outcome thresholding). The data can include, for example, data representing one or more of corrected anatomical metrics, presence of fusion, health related quality of life, activity level, or complications. In some embodiments, the data is or includes an outcome score, which can be calculated based on a single target outcome, an aggregate outcome, and/or an outcome threshold.

Optionally, the data phase 410 can include identifying or determining, for at least one patient data set of the selected subset (e.g., for at least one similar patient data set), surgical procedure data and/or medical device design data associated with the favorable treatment outcome. The surgical procedure data can include data representing one or more of a surgical approach, a corrective maneuver, a bony resection, or implant placement. The at least one medical device design can include data representing one or more of physical properties, mechanical properties, or biological properties of a corresponding medical device. In some embodiments, the at least one patient-specific medical device design includes a design for an implant or an implant delivery instrument.

In the modeling phase 420, a surgical procedure and/or medical device design is generated (block 422). The generating step can include developing at least one predictive model based on the patient data set and/or selected subset of reference patient data sets (e.g., using statistics, machine learning, neural networks, AI, or the like). The predictive model can be configured to generate the surgical procedure and/or medical device design.

In some embodiments, the predictive model includes one or more trained machine learning models that generate, at least partly, the surgical procedure and/or medical device design. For example, the trained machine learning model(s) can determine a plurality of candidate surgical procedures and/or medical device designs for treating the patient. Each surgical procedure can be associated with a corresponding medical device design. In some embodiments, the surgical procedures and/or medical device designs are determined based on surgical procedure data and/or medical device design data associated with favorable outcomes, as previously described with respect to the data phase 410. For each surgical procedure and/or corresponding medical device design, the trained machine learning model(s) can calculate a probability of achieving a target outcome (e.g., favorable or desired outcome) for the patient. The trained machine learning model(s) can then select at least one surgical procedure and/or corresponding medical device design based, at least partly, on the calculated probabilities.

The execution phase 430 can include manufacturing the medical device design (block 432). In some embodiments, the medical device design is manufactured by a manufacturing system configured to perform one or more of additive manufacturing such as 3D printing, stereolithography, digital light processing, fused deposition modeling, selective laser sintering, selective laser melting, electronic beam melting, laminated object manufacturing, powder bed printing, thermoplastic printing, direct material deposition, or inkjet photo resin printing. The execution phase 430 can optionally include generating fabrication instructions configured to cause the manufacturing system to manufacture a medical device having the medical device design.

The execution phase 430 can include performing the surgical procedure (block 434). The surgical procedure can involve implanting a medical device having the medical device design into the patient. The surgical procedure can be performed manually, by a surgical robot, or a combination thereof. In embodiments where the surgical procedure is performed by a surgical robot, the execution phase 430 can include generating control instructions configured to cause the surgical robot to perform, at least partly, the patient-specific surgical procedure.

The method 400 can be implemented and performed in various ways. In some embodiments, one or more steps of the method 400 (e.g., the data phase 410 and/or the modeling phase 420) can be implemented as computer-readable instructions stored in memory and executable by one or more processors of any of the computing devices and systems described herein (e.g., the system 200), or a component thereof (e.g., the client computing device 202 and/or the server 206). Alternatively, one or more steps of the method 400 (e.g., the execution phase 430) can be performed by a healthcare provider (e.g., physician, surgeon), a robotic apparatus (e.g., a surgical robot), a manufacturing system (e.g., manufacturing system 224), or a combination thereof. In some embodiments, one or more steps of the method 400 are omitted (e.g., the execution phase 430).

Figure 5A:
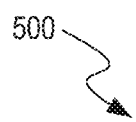

FIGS. 5A-5C illustrate exemplary data sets that may be used and/or generated in connection with the methods described herein (e.g., the data phase 410 described with respect to FIG. 3), according to an embodiment. FIG. 5A illustrates a patient data set 500 of a patient to be treated. The patient data set 500 can include a patient ID and a plurality of pre-operative patient metrics (e.g., age, gender, BMI, lumbar lordosis (LL), pelvic incidence (PI), and treatment levels of the spine (levels)).

FIG. 5B illustrates a plurality of reference patient data sets 510. In the depicted embodiment, the reference patient data sets 510 include a first subset 512 from a study group (Study Group X), a second subset 514 from a practice database (Practice Y), and a third subset 516 from an academic group (University Z). In alternative embodiments, the reference patient data sets 510 can include data from other sources, as previously described herein. Each reference patient data set can include a patient ID, a plurality of pre-operative patient metrics (e.g., age, gender, BMI, lumbar lordosis (LL), pelvic incidence (PI), and treatment levels of the spine (levels)), treatment outcome data (Outcome) (e.g., presence of fusion (fused), HRQL, complications), and treatment procedure data (Surg. Intervention) (e.g., implant design, implant placement, surgical approach).

FIG. 5C illustrates comparison of the patient data set 500 to the reference patient data sets 510. As previously described, the patient data set 500 can be compared to the reference patient data sets 510 to identify one or more similar patient data sets from the reference patient data sets. In some embodiments, the patient metrics from the reference patient data sets 510 are converted to numeric values and compared the patient metrics from the patient data set 500 to calculate a similarity score 520 ("Pre-op Similarity") for each reference patient data set. Reference patient data sets having a similarity score below a threshold value can be considered to be similar to the patient data set 500. For example, in the depicted embodiment, reference patient data set 510a has a similarity score of 9, reference patient data set 510b has a similarity score of 2, reference patient data set 510c has a similarity score of 5, and reference patient data set 510d has a similarity score of 8. Because each of these scores are below the threshold value of 20, reference patient data sets 510a-d are identified as being similar patient data sets.

The treatment outcome data of the similar reference patient data sets 510a-d can be analyzed to determine surgical procedures and/or implant designs with the highest probabilities of success. For example, the treatment outcome data for each reference patient data set can be converted to a numerical outcome score 530 ("Outcome Quotient") representing the likelihood of a favorable outcome. In the depicted embodiment, reference patient data set 510a has an outcome score of 1, reference patient data set 510b has an outcome score of 1, reference patient data set 510c has an outcome score of 9, and reference patient data set 510d has an outcome score of 2. In embodiments where a lower outcome score correlates to a higher likelihood of a favorable outcome, reference patient data sets 510a, 510b, and 510d can be selected. The treatment procedure data from the selected reference patient data sets 510a, 510b, and 510d can then be used to determine at least one surgical procedure (e.g., implant placement, surgical approach) and/or implant design that is likely to produce a favorable outcome for the patient to be treated.

In some embodiments, a method for providing medical care to a patient is provided. The method can include comparing a patient data set to reference data. The patient data set and reference data can include any of the data types described herein. The method can include identifying and/or selecting relevant reference data (e.g., data relevant to treatment of the patient, such as data of similar patients and/or data of similar treatment procedures), using any of the techniques described herein. A treatment plan can be generated based on the selected data, using any of the techniques described herein. The treatment plan can include one or more treatment procedures (e.g., surgical procedures, instructions for procedures, models or other virtual representations of procedures), one or more medical devices (e.g., implanted devices, instruments for delivering devices, surgical kits), or a combination thereof In some embodiments, a system for generating a medical treatment plan is provided. The system can compare a patient data set to a plurality of reference patient data sets, using any of the techniques described herein. A subset of the plurality of reference patient data sets can be selected, e.g., based on similarity and/or treatment outcome, or any other technique as described herein. A medical treatment plan can be generated based at least in part on the selected subset, using any of the techniques described herein. The medical treatment plan can include one or more treatment procedures, one or more medical devices, or any of the other aspects of a treatment plan described herein, or combinations thereof.

In further embodiments, a system is configured to use historical patient data. The system can select historical patient data to develop or select a treatment plan, design medical devices, or the like. Historical data can be selected based on one or more similarities between the present patient and prior patients to develop a prescriptive treatment plan designed for desired outcomes. The prescriptive treatment plan can be tailored for the present patient to increase the likelihood of the desired outcome. In some embodiments, the system can analyze and/or select a subset of historical data to generate one or more treatment procedures, one or more medical devices, or a combination thereof. In some embodiments, the system can use subsets of data from one or more groups of prior patients, with favorable outcomes, to produce a reference historical data set used to, for example, design, develop or select the treatment plan, medical devices, or combinations thereof.

Figure 6A:
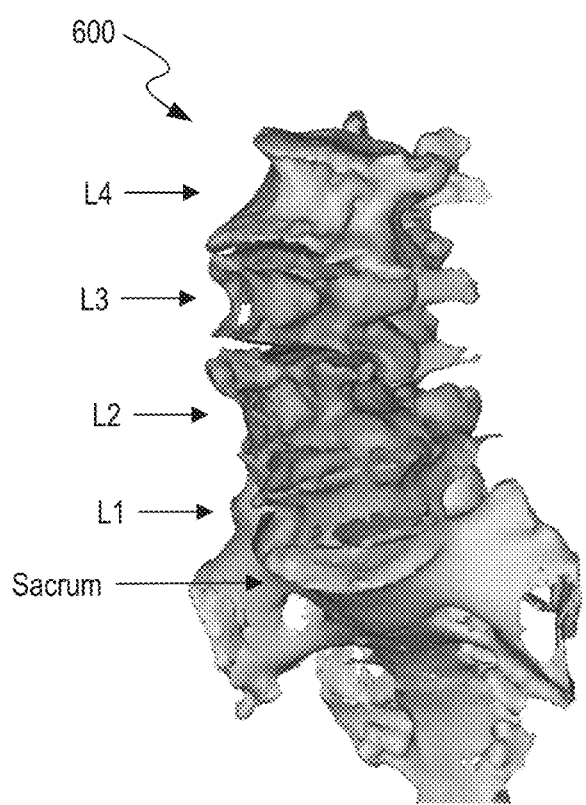
FIGS. 6A and 6B illustrate examples of a virtual model of a patient's native anatomical spinal configuration as identified by various methods of the present technology.
Figure 6B:
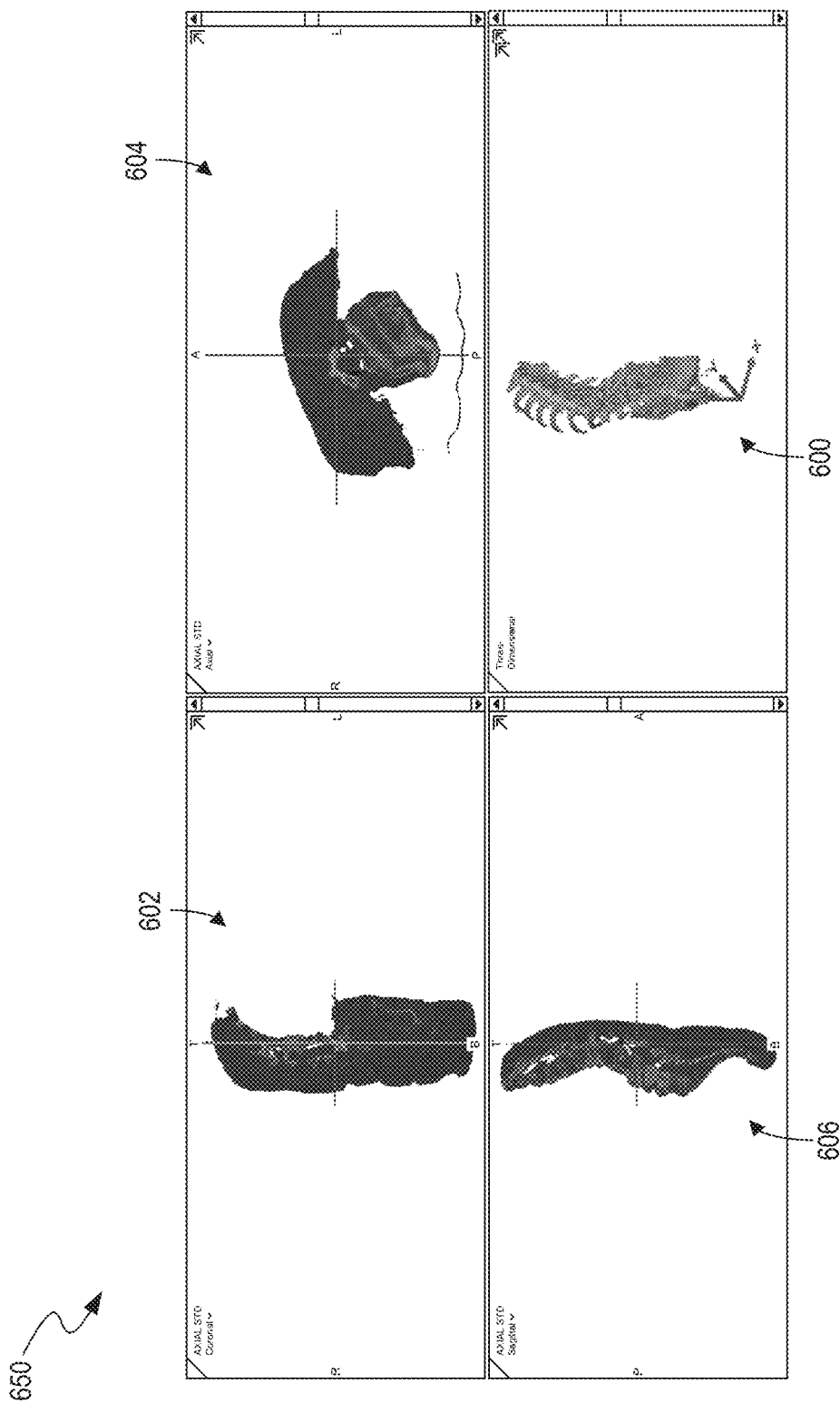

FIGS. 6A and 6B illustrate an example of a virtual model 600 of a patient's native anatomical configuration (e.g., associated with the patient data received at step 402 of the method 400 and/or as generated by a method 700 described below). In particular, FIG. 6A is an enlarged view of the virtual model 600 of the patient's native anatomy and shows the patient's native anatomy of their lower spinal cord region. The virtual model 600 is a three-dimensional visual representation of the patient's native anatomy. In the illustrated embodiment, the virtual model includes a portion of the spinal column extending from the sacrum to the L4 vertebral level. Of course, the virtual model can include other regions of the patient's spinal column, including cervical vertebrae, thoracic vertebrae, lumbar vertebrae, and the sacrum. The illustrated virtual model 600 only includes bony structures of the patient's anatomy, but in other embodiments may include additional structures, such as cartilage, soft tissue, vascular tissue, nervous tissue, etc.

FIG. 6B illustrates a virtual model display 650 (referred to herein as the "display 650") showing different views of the virtual model 600. The virtual model display 650 includes a three-dimensional view of the virtual model 600, one or more coronal cross-section(s) 602 of the virtual model 600, one or more axial cross section(s) 604 of the virtual model 600, and/or one or more sagittal cross-section(s) 606 of the virtual model 600. Of course, other views are possible and can be included on the virtual model display 650. In some embodiments, the virtual model 600 may be interactive such that a user can manipulate the orientation or view of the virtual model 600 (e.g., rotate), change the depth of the displayed cross-sections, select and isolate specific bony structures, or the like.

Figure 7:
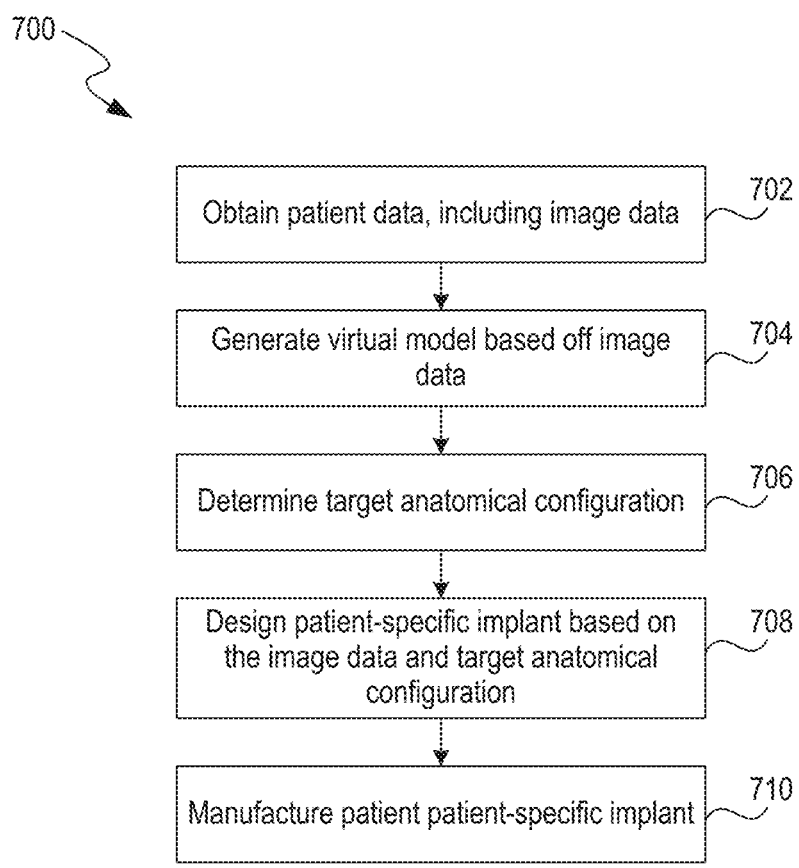
FIG. 7 is a flowchart of a method for designing a patient-specific implant in accordance with some embodiments of the present technology.

FIG. 7 is a flowchart of a method 700 for designing a patient-specific implant in accordance with select embodiments of the present technology. In particular, the method 700 includes using one or more software modules (e.g., treatment planning module 218 and/or implant design module 364) to determine, analyze, and/or evaluate the anatomical configuration of a native joint and to design a patient-specific implant based on the determined anatomical configuration. For example, in some embodiments, the method 700 can be used to design a patient-specific IBF device of the type illustrated in FIGS. 1A and 1B.

Certain aspects of the method 700 are generally similar to certain aspects of the method 400 described above with respect to FIG. 4. Accordingly, the following description of the method 700 focuses on aspects of the method 700 not described with respect to the method 400, with the understanding that the description of similar steps in method 400 applies to like steps in the method 700.

Similar to method 400, the method 700 can begin in block 702 by obtaining patient data. Patient data can include, for example, image data of the patient's spine. In some embodiments, the patient data may also include other patient data and/or data from one or more anatomical and/or kinematic studies performed on the patient. The method 700 further includes generating, based at least in part on the image data, a virtual model of one or more regions of the patient's anatomy in block 704. The virtual model can be similar to the virtual model described in detail above with respect to FIGS. 6A and 6B. In some embodiments, block 704 can be omitted, and the method 700 can proceed from block 702 directly to block 706.

In block 706, a user and/or the software module can determine a target anatomical configuration. The target anatomical configuration can be different than the native anatomical configuration shown in the image data. The target anatomical configuration can include an adjustment to one or more anatomical features relative to the native anatomical configuration, including, but not limited to, an adjustment to spacing between vertebral bodies, orientation of vertebral bodies, alignment of two or more vertebral bodies, lumbar lordosis, Cobb angle(s), pelvic incidence, disc height, segment flexibility, rotational displacement, and the like. For example, in embodiments in which the patient has vertebral disc degeneration between two vertebrae, the image data may illustrate that the native anatomical configuration has a reduced or sub-optimal distance between an inferior boundary of a first vertebra and a superior boundary of the second vertebra. The target anatomical configuration may therefore include an increased distance between the first and second vertebrae that is reflective of a "healthy" or "normal" anatomy. In another example, the image data may illustrate that a first vertebra is out of alignment with a second vertebra. In such embodiments, the target anatomical configuration may therefore include realigning the first vertebra and the second vertebra.

In embodiments in which a user determines the target anatomical configuration, the user can use the virtual model to manipulate one or more relationships (distances, angles, constraints, etc.) between individual vertebrae to set the target anatomical configuration. Manipulations can include, but are not limited to, translation along an axis or curve, rotation about an axis or centroid, and/or rotation about the center of mass. In some embodiments, the manipulation can be done until the virtual model illustrates the anatomy in a "desired" anatomical configuration. The user can then provide an input setting the illustrated desired anatomical configuration as the target anatomical configuration.

In embodiments in which a software module determines the target anatomical configuration, the software module may automatically manipulate the virtual model to provide a recommend target anatomical configuration based on one or more design criteria and/or reference patient data sets. Suitable design criteria can include, for example, target values associated with various anatomical features, including, for example, target values associated with vertebral spacing (e.g., minimum vertebral body spacing, maximum vertebral spacing, etc.), vertebral orientation, vertebral alignment, vertebral translation, lumbar lordosis, Cobb angle(s), pelvic incidence, disc height, segment flexibility, rotational displacement, kinematics, or the like. Suitable reference patient data sets can be identified using, for example, a process similar to that described above at blocks 414 and 416. The implant design module can further perform one or more simulations, analyses (e.g., stress analysis, fatigue analysis, etc.), or the like to provide feedback (e.g., identified high stress regions), design recommendations, treatment recommendations (e.g., steps to prepare implantation site), or the like.

In some embodiments, determining the target anatomical configuration includes using the software module to provide a recommend target anatomical configuration, and then permitting the physician to optionally further modify the target anatomical configuration. In some embodiments, the determining the target anatomical configuration includes an iterative process with the physician. For example, the physician can use the virtual model to manipulate one or more relationships between vertebrae to set the target anatomical configuration; the software module can analyze the target anatomical configuration to recommend adjustments; the physician can review the recommendations and further manipulate relationships between vertebrae to tweak the target anatomical configuration; and the system can analyze the tweaked target anatomical configuration. In another example, the software module can automatically manipulate the virtual model to provide a recommend target anatomical configuration; the physician can tweak the recommended target anatomical configuration; and the system can automatically analyze the tweaked target anatomical configuration.

The method 700 continues by designing a patient-specific implant in block 708. The patient-specific implant can be designed using the software module, which can be the same as or different than the software modules optionally used in block 706. Among other things, the software module designs the patient-specific implant to facilitate reaching the target anatomical configuration when it is implanted in the patient. Accordingly, the patient-specific implant should fit in the negative space (e.g., the "implant envelope") of the target anatomical configuration. The negative space can be used to determine various geometric parameters of the patient-specific implant. The geometric parameters include, but are not limited to, dimensions, heights, surfaces, footprints, and the like. In some embodiments, a virtual patient-specific implant can be created and shown within the negative space of the virtual representation of the patient anatomy.

In some embodiments, to fit the patient-specific implant into the negative space, the software module designs the patient-specific implant to match the anatomical topography of the target region. For IBF devices, for example, this includes matching the topography of the IBF device's endplates to the topography of the adjacent vertebrae. For example, referring back to FIG. 1A, the first surface 142 of the first endplate 140 is designed to mate with the topography of the inferior vertebral surface 112 of the first vertebra 110, while the first surface 152 of the second endplate 150 is designed to mate with the topography of the superior surface 122 of the second vertebra 120. For example, if the inferior vertebral surface 112 of the first vertebra 110 is slightly convex, the first surface 142 of the first endplate 140 will be designed as slightly concave to "mate" with the slightly convex vertebral surface. In another example, if the superior surface 122 of the second vertebra 120 contains a defect (e.g., a divot, protrusion, or any other defect), the first surface 152 of the second endplate 150 will be designed with features to "mate" with the defect. Without being bound by theory, increasing the fit (e.g., forming a gapless or generally gapless interface) between the implant's endplates and the vertebrae is expected to prevent and/or reduce instances of dynamic failure of the implants (e.g., by reducing and/or preventing micro-motions of the implant), further tailor the medical correction (e.g., segmental height, lordosis, and/or coronal correction) from the implants, and/or otherwise increase the efficacy of the implants.

After the patient-specific implant is designed, the method 700 can continue in block 710 by manufacturing the patient-specific implant. In some embodiments, the patient-specific implant design(s) can be transmitted from the software module to a manufacturing system for manufacturing the patient-specific implant. For example, the method can include generating computer-executable manufacturing instructions that, when executed by a manufacturing system, direct the manufacturing system to manufacture the patient-specific implant. The manufacturing instructions can be transmitted to the manufacturing system using any suitable means. The manufacturing system can be located on site or off site. On-site manufacturing can reduce the number of sessions with a patient and/or the time to be able to perform the surgery whereas off-site manufacturing can be useful make complex devices, and may have specialized manufacturing equipment. In some embodiments, more complicated device components can be manufactured off site, while simpler device components can be manufactured on site.

Various types of manufacturing systems are suitable for use in accordance with the embodiments herein. For example, the manufacturing system can be configured for additive manufacturing, such as three-dimensional (3D) printing, stereolithography (SLA), digital light processing (DLP), fused deposition modeling (FDM), selective laser sintering (SLS), selective laser melting (SLM), selective heat sintering (SHM), electronic beam melting (EBM), laminated object manufacturing (LOM), powder bed printing (PP), thermoplastic printing, direct material deposition (DMD), inkjet photo resin printing, or like technologies, or combination thereof. Alternatively, or in combination, the manufacturing system can be configured for subtractive (traditional) manufacturing, such as CNC machining, electrical discharge machining (EDM), grinding, laser cutting, water jet machining, manual machining (e.g., milling, lathe/turning), or like technologies, or combinations thereof. The manufacturing system can manufacture one or more patient-specific medical devices based on fabrication instructions or data (e.g., CAD data, 3D data, digital blueprints, stereolithography data, or other data suitable for the various manufacturing technologies described herein). In some embodiments, the patient-specific implants can include features, materials, and designs shared across designs to simplify manufacturing. For example, deployable patient-specific implants for different patients can have similar internal deployment.

Additional details for receiving, identifying, storing, downloading, and/or accessing patient-specific data and surgical plans, and additional systems and methods for designing and manufacturing patient-specific implants and patient-specific surgical plans, are described in U.S. application Ser. No. 16/990,810, filed Aug. 11, 2020, W.O. Application No. PCT/US21/12065 filed, Jan. 4, 2021, and U.S. application Ser. No. 16/987,113, filed Aug. 6, 2020, the disclosures of which are incorporated by reference herein in their entirety.

Various examples of the results of the embodiments discussed in connection with FIGS. 2-7, as well as further details on the patient-specific conditions the methods 400, 700 can be used to address, are described in more detail below with respect to FIGS. 8A-24.

Patient-Specific Intervertebral Body Fusion Devices

Figure 8A:
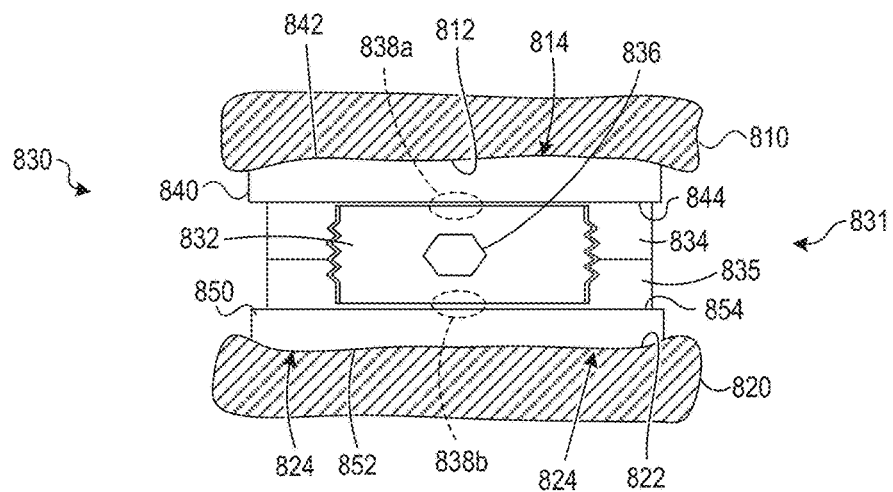
FIG. 8A is a posterior view of an implanted patient-specific intervertebral body fusion device manufactured according to various methods of the present technology.
Figure 8B:
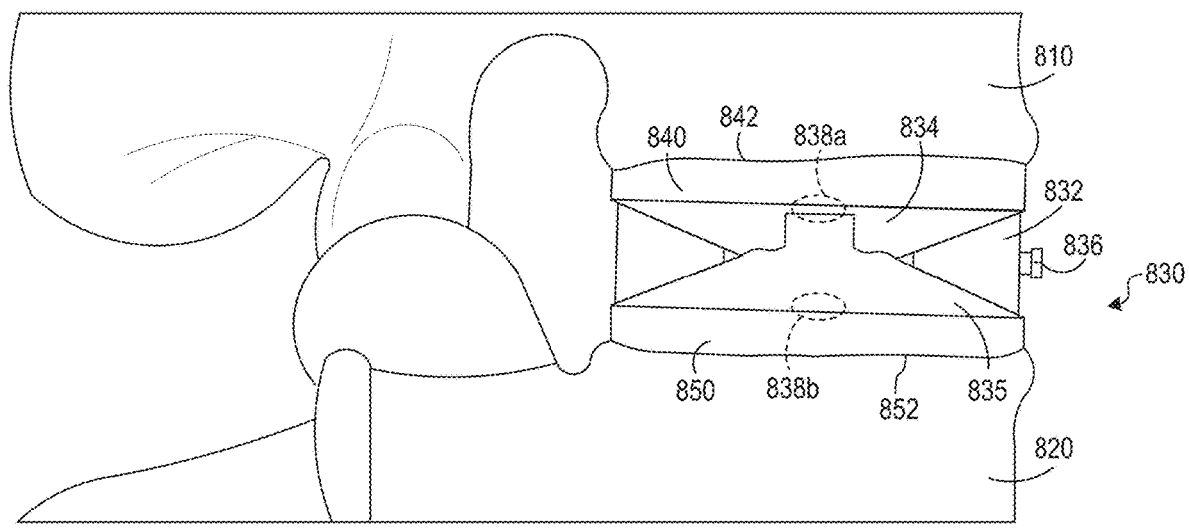
FIG. 8B is a side view of the patient-specific intervertebral body fusion device of FIG. 8A according to various methods of the present technology.

FIGS. 8A and 8B are schematic anterior and side illustrations, respectively, of a patient-specific IBF device 830 ("device 830") manufactured and deployed between a first vertebra 810 (e.g., a relatively superior vertebra) and a second vertebra 820 (e.g., a relatively inferior vertebra) in accordance with some embodiments of the present technology. As illustrated, the device 830 is positioned in the intervertebral or disc space between the first vertebra 810 and the second vertebra 820 and in an expanded configuration.

Like the device 130 discussed above with respect to FIGS. 1A and 1B, the device 830 includes an expansion body or main body 831 with a mechanism to adjust the vertical expansion of the device 830. The internal components of the main body 831 can be designed and manufactured to achieve a desired treatment plan. The patient-specific expansion can be selected based, at least in part, on the design of other components of the device 830. The device 830 can have a patient-specific design resulting from the method 400 and/or the method 700 discussed above with respect to FIGS. 4 and 7. For example, as discussed in more detail below, the device 830 can have a patient-specific design resulting from the patient image data and/or the prescribed course of treatment.

The main body 831 can be configured to expand from a collapsed configuration to an expanded configuration (illustrated in FIGS. 8A and 8B) and can include one or more expansion mechanisms (e.g., screw jack mechanisms, wedges, scissors mechanisms, etc.), angled or sloped surfaces, inflatable members, or other components for causing deployment. Additionally, the main body 831 can include linkages, pin connections, linkage assemblies, or other components for connecting various other components. In some embodiments, the device 830 includes a drive feature 836 (e.g., a drive head, a screw head, a bolt head, etc.) coupleable to a drive instrument. The drive feature 836 can be connected to one or more drive elements (e.g., threaded bodies, wedge members, drive shafts, etc.) of the device 830.

As best shown in FIG. 8B, the main body 831 includes a screw jack mechanism having lateral end portions 832, an upper component 834 that mates with the lateral end portions 832, a lower component 835 that mates with the lateral end portions 832, and the drive feature 836 operably connected to the lateral end portions 832. The drive feature 836 can be operated to force the lateral end portions 832 towards each other, thereby forcing the upper and lower components 834, 835 to move vertically to expand the device 830. As described above, in some embodiments, the device 830 includes lockable mechanical and/or electrical stops (not shown) that can prevent the device 830 from being expanded beyond a desired point. For example, in some embodiments, the stopper can be pre-operatively locked in position to prevent the expansion of the device 830 past a predetermined point to provide a height restoration to the first and second vertebrae 810, 820. During surgery, the device 830 can be inserted then expanded until the stop prevents further expansion. The main body 831 can also be a non-patient specific mechanism that can be selected from a set of standard mechanisms with different configurations (e.g., collapsed configuration, expanded configuration, expansion characteristics, etc.). The selection can be based upon the treatment plan. If a standard mechanism does not meet the treatment plan, the system can design the patient-specific main body 831 or select a standard main body from a set of alternative devices and adjust the design of other components of the device. The number and configuration of components of the device 830 can be selected based, at least in part, on the patient anatomy, treatment plan, or the like.

As further illustrated in FIGS. 8A and 8B, the device 830 can further include a first endplate 840 (e.g., a superior or upper endplate) and a lockable joint 838a connecting the first endplate 840 to the main body 831 at the upper component 834. The device 830 can further include a second endplate 850 (e.g., an inferior or lower endplate) and a lockable joint 838b connecting the second endplate 850 to the main body 831 at the lower component 835. In the illustrated embodiment, the connections are achieved through lockable joints 838, for example the lockable ball joints described in more detail below with respect to FIG. 23. The lockable joints 838 allow the first and second endplates to be adjusted then locked to provide a desired lordotic and/or coronal correction between the first and second vertebrae 810, 820. In various embodiments, the first and second endplates 840, 850 can be pre-operatively and/or intraoperatively adjusted and locked on the lockable joints 838.

The first endplate 840 includes a first surface 842 (e.g., a superior surface) that mates with an inferior surface 812 of the first vertebra 810 and a second surface 844 (e.g., an inferior surface) that mates with the upper component 834 (e.g., through the first lockable joint 838a). Further, as illustrated, the first surface 842 is custom-manufactured to mate with the patient-specific topology of the inferior surface 812 of the first vertebra 810. For example, as illustrated with respect to FIG. 8A, the inferior surface 812 can include a patient specific feature 814, such as a recessed region, a valley, or a divot. A flat endplate that was not customized to the patient-specific topology of the inferior surface 812 would result in a gap at the patient specific feature 814 (i.e., a gap where the first endplate 840 does not contact the first vertebra 810). In contrast, the contoured first surface 842 of the first endplate 840 matches the inferior vertebral surface 812 to increase the area of contact, thereby limiting or reducing stresses, such as stresses in the first vertebra 810 and/or the device 830. As a result of the more complete contact made by the first endplate 840, the device 830 is expected to have a more optimal surface area contact with the first vertebra 810 to improve the traction of the device 830 and/or improve the expected outcome for a medical treatment using the device 830.

The contoured first surface 842 of the device 830 can also reduce or limit motion between the first vertebra 810 and the device 830. The reduced motion can help reduce spinal fusion time. In some embodiments, the contoured first surface 842 can have a thickened or protruding region that is substantially geometrically concurrent to the patient-specific feature 814 along the inferior surface 812. This further helps the first endplate 840 to seat against the first vertebra 810. When an axial load is applied to device 830, the customized mating at the interface can limit, reduce, or substantially prevent relative movement between device 830 and the first vertebra 810. In some procedures, the device 830 can be configured to provide a generally gapless interface when the device 830 is in a fully expanded, implanted configuration.

Similarly, the second endplate 850 includes a first surface 852 (e.g., an inferior or lower surface) that mates with a superior surface 822 of the second vertebra 820 and a second surface 854 (e.g., a superior surface) that mates with the lockable joint 838b and the lower component 835. As illustrated in FIGS. 8A and 8B, the first surface 852 is customized to the patient-specific topology of the superior surface 822 of the second vertebra 120. For example, the superior surface 822 can include multiple patient-specific features 824, such as the illustrated valleys or divots. An endplate that was not customized to the patient-specific topology of the superior surface 822 include one or more gaps corresponding to the patient-specific features 824 where the second endplate 850 does not contact the second vertebra 820. As a result of the patient-specific customization of the second endplate 850, the device 830 can maintain contact with the second vertebra 820. As a result of the more complete contact made by the second endplate 850, the device 830 is expected to have more optimal surface area contact with the second vertebra 820 to improve the traction of the device 830 and/or improve the expected outcome for a medical treatment using the device 830.

As described above with respect to FIG. 7, implants such as the device 830 can be manufactured after receiving patient data and generating a virtual model of the patient's spine. In some embodiments, the patient data and virtual model allow a manufacturing method to identify the topology of the inferior surface 812 of the first vertebra 810 and/or the superior surface 822 of the second vertebra 820 ("surfaces 812, 822 of the vertebrae 810, 820"). The topology indicates patient-specific features such as a general shape of the surfaces (e.g., concave, convex, etc.) as well as imperfections on the surfaces (e.g., valleys, divots, protrusions, etc.). Once the topology of the inferior surface 812 of the first vertebra 810 and/or the superior surface 822 of the second vertebra 820 is known, the manufacturing method generates a plan to customize the device 830 to mate with the topology. In some embodiments, for example, the plan can include customizing the first and second endplates 840, 850 with features that match the imperfections on the surfaces 812, 822 of the vertebrae 810, 820. For example, as discussed above, the first endplate 840 can include a feature (e.g., a protrusion) on the first surface 842 generally corresponding to the patient-specific feature 814 on the inferior surface 812 of the first vertebra 810, while the second endplate 850 can include features on the first surface 852 generally corresponding to the patient-specific features 824 on the superior surface 822 of the second vertebra 820.

In some embodiments, the patient data and virtual model allow the manufacturing method to identify a desired anatomical correction between the first and second vertebrae 810, 820. For example, for a patient experiencing scoliosis, the desired anatomical correction can include a coronal correction between the first and second vertebrae 810, 820. Once the desired anatomical correction is known, the manufacturing method generates a plan to customize the device 830 to help achieve the desired anatomical correction. For example, the plan can include customizing the first and second endplates 840, 850 to facilitate the anatomical correction. In some embodiments, the first and second endplates 840, 850 can be customized with a varying thickness in the x-y plane to facilitate mating with the scoliotic vertebrae. In some embodiments, the angular position of the first and second endplates 840, 850 are affixed to the main body 831 at can be adjusted via the lockable joints 838. An example of the result of the plan is discussed further below with respect to FIG. 9.

In some embodiments, the patient data and virtual model allow the manufacturing method to identify relatively strong and/or weak regions of the surfaces 812, 822 of the vertebrae 810, 820. The relatively strong regions can withstand more force than the relatively weak regions and are therefore more desirable to be contacted by the device 830. In some embodiments, accordingly, the manufacturing method generates a plan to customize the device 830 to apply force to the identified relatively strong regions of the surfaces 812, 822 of the vertebrae 810, 820. For example, the plan can include customizing the first and second endplates 840, 850 with gaps generally corresponding to the relatively weak regions on the surfaces 812, 822 of the vertebrae 810, 820, thereby applying force to the relatively strong regions. An example of the result of the plan is discussed further below with respect to FIGS. 11A and 11B.

In some embodiments, the patient data and virtual model allow the manufacturing method to identify a more suitable IBF device from a group of IBF devices. For example, in some embodiments, the manufacturing method can select from an expandable screw jack, an expandable scissor jack, and/or any other expandable cage; a fixed cage; devices sized to contact only a portion of the first and second vertebrae 810, 820; devices sized to contact the entirety of the first and second vertebrae 810, 820; devices made from titanium, polymers, carbon fiber, bone grafts, and/or any other suitable material; etc. The suitability of each device can be dependent on the underlying medical condition being treated, patient-specific factors (e.g., age, overall health, etc.), and/or the desired medical outcome. Once the type of IBF device is selected, the manufacturing method generates a plan to customize first and second endplates 840, 850 to the device. For example, in some embodiments, the plan includes customizing the second surface 844, 854 of the first and second endplates 840, 850 to facilitate connection to the selected device. In some embodiments, the plan includes customizing the first surface 842, 852 of the first and second endplates 840, 850 based on the treatment supplied by the selected device. A few examples of the results are discussed further below with respect to FIGS. 12-16.

In some embodiments, once a plan is generated, the manufacturing method can then generate the first and second endplates 840, 850 with the customized topologies. For example, as described above with respect to FIG. 7, the first and second endplates 840, 850 can be manufactured using various additive manufacturing processes (e.g., 3D printing, stereolithography, digital light processing, fused deposition modeling, selective laser sintering, selective laser melting, selective heat sintering, electronic beam melting, laminated object manufacturing, powder bed printing, thermoplastic printing, direct material deposition, inkjet photo resin printing, and/or like technologies), and/or subtractive manufacturing processes (e.g., CNC machining, electrical discharge machining, grinding, laser cutting, water jet machining, manual machining (e.g., milling, lathe/turning), and/or like technologies). In some embodiments, the manufacturing method can additionally, or alternatively, generate the selected IBF device with patient-specific dimensions. For example, in some embodiments, the height of the fully expanded device 830 generated by the manufacturing method is generally equal to a desired height restoration from the medical procedure. In some embodiments, the x-y dimensions of the device 830 generated by the manufacturing method corresponds to planned dimensions for the device 830 to contact targeted regions of the first and second vertebrae 810, 820.

Figure 9:
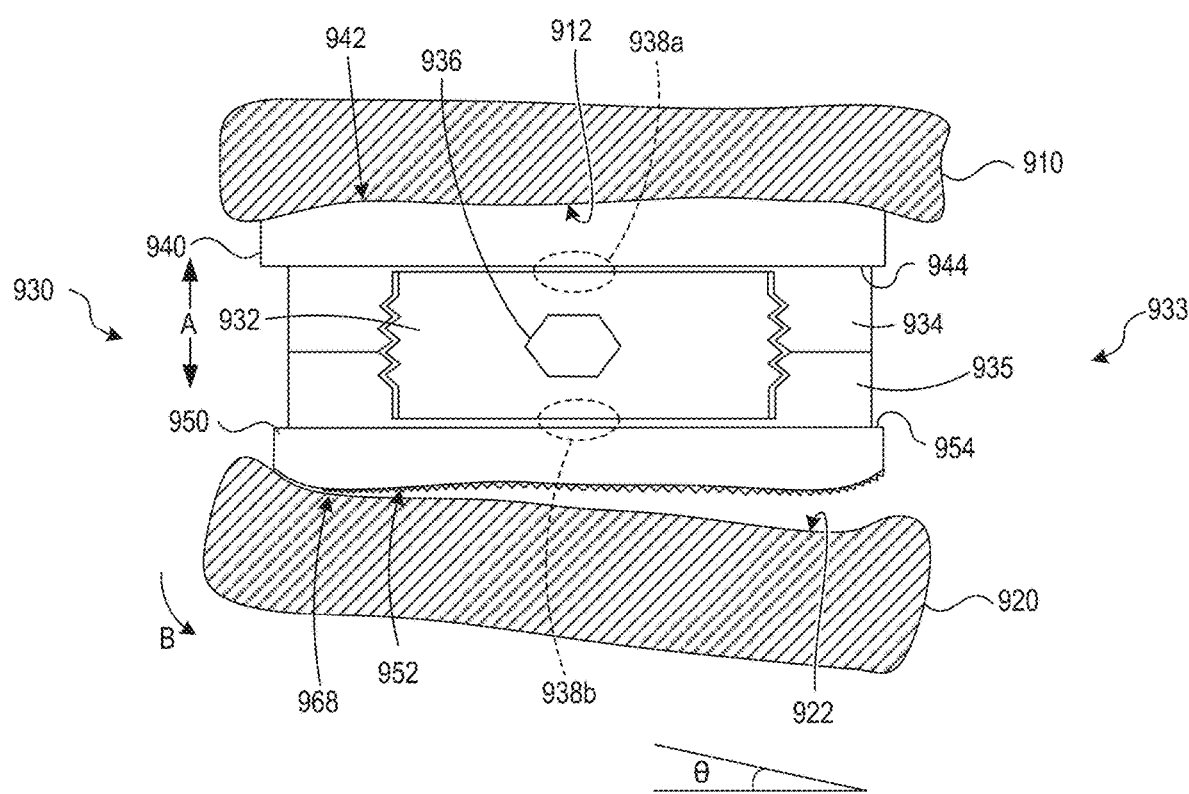
FIG. 9 is a schematic illustration of a patient-specific device positioned between vertebral endplates according to various methods of the present technology.

FIG. 9 is a schematic anterior illustration of a patient-specific device 930 manufactured according to the method 700 in accordance with some embodiments of the present technology. As illustrated, the device 930 is generally similar in structure and function to the device 830 described in more detail above with respect to FIGS. 8A and 8B. For example, the device 930 includes lateral end portions 932, an upper component 934 that mates with the lateral end portions 932, a lower component 935 that mates with the lateral end portions 932, and an adjustment mechanism 936 (e.g., a screw, bolt, twisting adjuster, or other suitable mechanism) operably connected to the lateral end portions 932. A first endplate 940 is connected to the upper component 934 to contact the first vertebra 910 and a second endplate 950 is connected to the lower component 935 to contact the second vertebra 920.

In the illustrated embodiment, the device 930 is configured to provide a coronal correction between a first vertebra 910 and a second vertebra 920. As illustrated, the second vertebra 920 is rotated to an angle θ, thereby causing scoliosis in the patient's spine. As the device 930 expands along axis A, the first surface 952 of the second endplate 950 contacts a portion 968 of the superior surface 922 of the second vertebra 920. As the device 930 continues to expand along the axis A, the second endplate 950 pushes the contacted portion of second vertebra 920, causing the second vertebra 920 to rotate along as shown by arrow B, thereby reducing the angle θ. In some embodiments, the angle θ is reduced to about zero when the device 930 is fully expanded, thereby eliminating the scoliosis in the patient's spine between the first and second vertebrae 910, 920. In some such embodiments, the first surface 952 of the second endplate 950 can have a topology configured to mate with the superior surface 922 of the second vertebra 920 when the angle θ is reduced to about zero. In some embodiments, the angle θ is reduced by a predetermined amount when the device 930 is fully expanded, thereby achieving a desired, safest, and/or best possible medical outcome for the patient. In some such embodiments, the first surface 952 of the second endplate 950 can have a topology configured to mate with the superior surface 922 of the second vertebra 920 when the angle θ is reduced the predetermined amount.

FIGS. 10A-10E are partially schematic side views of spinal segments illustrating various vertebra topologies and the customization of implants to match the topologies. The implants discussed in connection with FIGS. 10A-10E can have features and components discussed in connection with other implants disclosed herein. The features, collapsed configuration, expanded configuration, and dimensions of the implant can be selected based on the treatment plan.

FIG. 10A illustrates a spinal segment 1010 with generally flat vertebral endplates (e.g., that have generally level surfaces devoid of any curvature). An implant 1011 is positioned between the vertebral bodies and includes generally flat device endplates matching the generally flat surfaces on the vertebral endplates. The implant 1011 can include an expansion mechanism that moves the device endplates apart to a desired distance and/or angular position to provide a desired anatomical positioning.

FIG. 10B illustrates a spinal segment 1012 with hooked superior and inferior vertebral endplates. The superior vertebral endplate has a posterior concavity while the inferior endplate has a posterior endplate extension adjacent to the posterior concavity, each departing from a neutral level for the vertebral endplates. An implant 1013 is positioned between the vertebral bodies and includes an upper endplate matching the hooked superior vertebral endplate and a lower endplate matching the hooked inferior vertebral endplate. This allows the implant 1013 to be implanted at the site without substantial amounts of bone being removed and without reducing the area of contact between the implant 1013 and the vertebral endplates. In some embodiments, the contouring of the endplates on the implant 1013 increase the area of contact with the vertebral bodies.

FIG. 10C illustrates a spinal segment 1014 with a concave superior vertebral endplate that departs from a neutral level of the superior endplate. An implant 1015 is positioned between the vertebral bodies and includes an upper endplate configured match the concavity of the superior endplate. This allows the implant 1015 to be implanted at the site without substantial amounts of bone being removed and without reducing the area of contact between implant 1015 and the vertebral endplates. In some embodiments, the contouring of the endplates on the implant 1015 increase the area of contact with the vertebral bodies.

FIG. 10D illustrates a spinal segment 1016 with a convex inferior vertebral endplate that departs from a neutral level of the inferior endplate. An implant 1017 is positioned between the vertebral bodies and includes a lower endplate that is configured to match the convex inferior endplate. This allows the implant 1017 to be implanted at the site without substantial amounts of bone being removed and without reducing the area of contact between implant 1017 and the vertebral endplates. In some embodiments, the contouring of the endplates on the implant 1017 increase the area of contact with the vertebral bodies.

FIG. 10E shows a spinal segment 1018 with a concave superior vertebral endplate and a convex inferior vertebral endplate, each departing from a neutral level of the endplates. An implant 1019 is positioned between the vertebral bodies and includes endplates that are configured to match the concave and convex vertebral endplates, with a convex upper endplate and a concave lower endplate. This allows the implant 1019 to be implanted at the site without substantial amounts of bone being removed and without reducing the area of contact between implant 1019 and the vertebral endplates. In some embodiments, the contouring of the endplates on the implant 1019 increase the area of contact with the vertebral bodies.

As discussed above, the overall topology of vertebral endplates differs between patients, and often even differs between the vertebrae in a single patient. For example, a single patient may have a few vertebrae with flat endplates and at least one vertebrae pair with hooked endplates. Accordingly, it is expected to be advantageous to customize the endplates of an IBF device to the topology of the specific vertebrae pair within a patient to improve the match between the IBF device and the treated vertebrae pair. For example, an IBF device fitting between the vertebrae in spinal segment 1018 can be customized to the patient by including a convex superior endplate mating with the concave superior vertebra and a concave inferior endplate mating with the inferior vertebra.

Figure 10F:
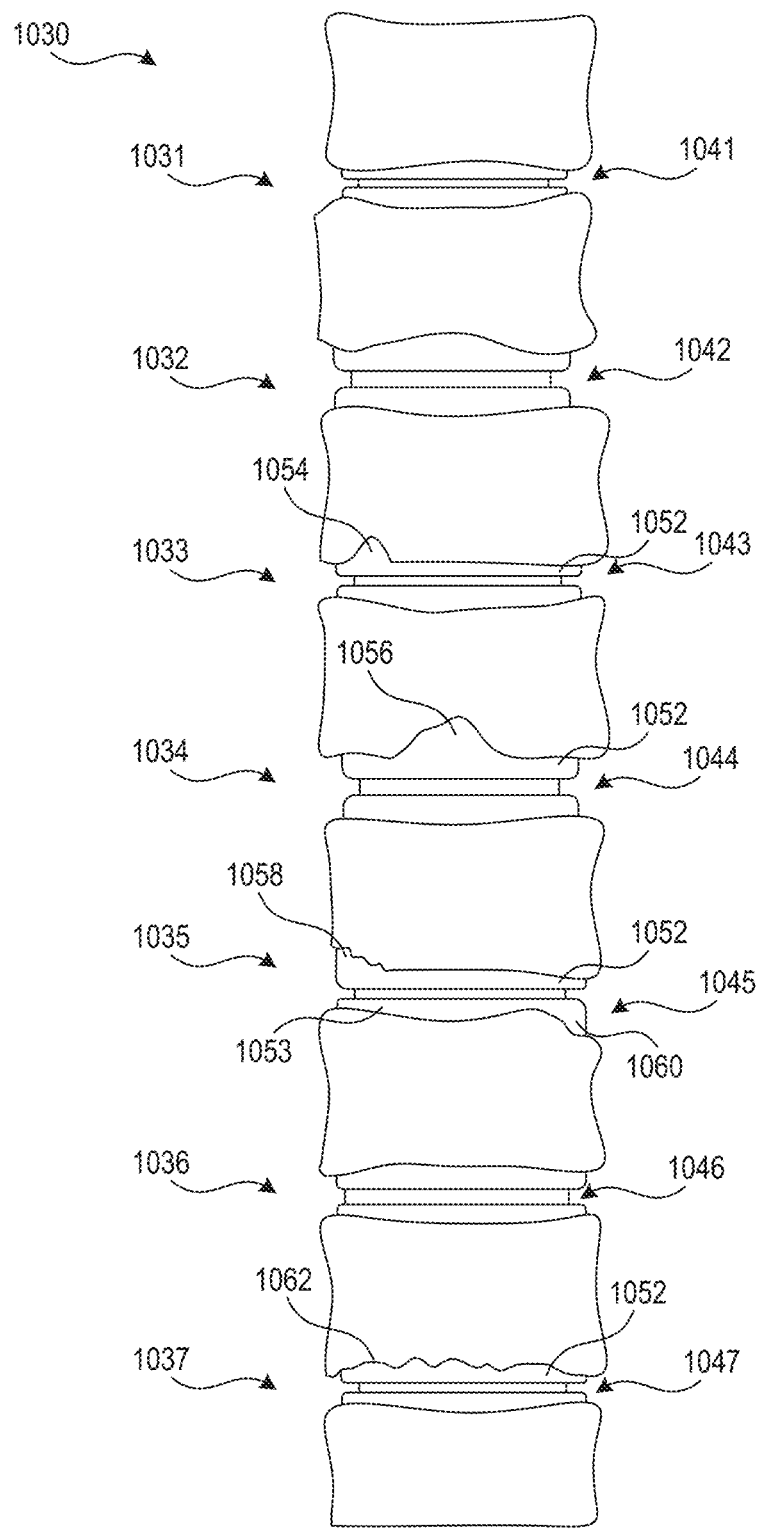
FIG. 10F is a posterior view of a spinal segment illustrating various vertebra topologies.

FIG. 10F shows a spinal segment 1030 with implants located at each individual level. In various embodiments, a spinal procedure may include implantation of implants at one or multiple levels. In the illustrated embodiment, the spinal segment 1030 has implants at each individual level. Further, the configuration of the implants at each individual level can be tailored to a treatment plan specific to the individual level. Each of the levels of the spinal segment 1030 are discussed below.

An implant 1041 is implanted at a level 1031 with normal endplates free from any defect in the surface topology. The implant 1041 can have endplates with a convex shape that match the illustrated concave endplates of the adjacent vertebrae at the level 1031. An implant 1042 is implanted at a level 1032 with a severe concave shape in the superior and inferior vertebra. The implant 1042 has large convex contours that match the corresponding concave shape of the superior vertebra.

An implant 1043 is implanted at a level 1033 with a superior endplate having a focal defect adjacent, but not on, a longitudinal side of the superior vertebra. The implant 1043 has an upper endplate 1052 with a contouring feature 1054 generally corresponding to the focal defect to better fit the superior endplate. Similarly, an implant 1044 is implanted at a level 1034 with a superior endplate having a focal defect adjacent between longitudinal sides of the superior vertebra. The implant 1044 has an upper endplate 1052 with a contouring feature 1056 generally corresponding to the focal defect to better fit the superior endplate. Focal defects in a patient's spine can range from relatively small cavities (e.g., as shown at the level 1033) to relatively large valleys (e.g., as shown at the level 1034). Further, focal defects can include protrusions (not shown) where excess bone and/or cartilage is collected, requiring concave contouring features in the endplates of the implants to match them.

An implant 1045 is implanted a level 1035 with corner defects in the superior and inferior vertebrae. Corner defects are located at least partially on longitudinal sides of the vertebrae. Corner defects can include missing corners that are cut off at varying angles, protrusions (not shown) at the corners, and/or rough topology at the corners (e.g., on the missing corner, on the protrusion, and/or on the otherwise normal surface of the corner). The implant 1045 has an upper endplate 1052 with a periphery contour 1058 configured to fit the corner defect in the superior endplate and a lower endplate 1053 with a periphery contour 1060 configured to fit the corner defect in the inferior endplate. Of course, other adjacent levels, such as level 1036, can be formed by endplates with relatively smooth and straight topologies. In such embodiments, an implant 1036 with relatively smooth contouring can be implanted at level 1036.

An implant 1047 is implanted at level 1037 with a superior vertebra having erosive defects on the inferior surface of the superior vertebra. As illustrated, erosive defects can span the entire surface of a vertebra and include multiple valleys and peaks therein. In some patients, erosive defects can be contained to a focal region and/or a corner region of a surface. In some patients, erosive defects can include one or more deep valleys and/or one or more tall peaks. As illustrated, the implant 1047 can have an upper endplate 1052 with an undulating or wavy superior surface 1062 configured to mate with the erosive defects in the superior vertebra.

Similar to the discussion above with respect to FIGS. 10A-10E, the local topology of vertebral endplates differs between patients, and often even differs between the vertebrae in a single patient. For example, a single patient may have a few vertebrae with normal endplates (e.g., level 1031) as well as one or more vertebrae with focal defects (e.g., level 1033). Thus, it can be advantageous to customize the upper and/or lower endplates of an IBF device to the local topology of the specific vertebrae pair at each individual level within a patient's spine to improve the match between the IBF device and the treated vertebrae pair.

Although overall topologies were discussed herein with respect to side views of the vertebra (e.g., along the sagittal axis) in FIGS. 10A-10E, one of skill in the art will understand that patients also have overall topologies along the frontal axis. Further, the benefits of matching the overall topology are expected to extend to customizing endplates to match the overall topology along the frontal axis in addition to the overall topology along the sagittal axis. Similarly, although defects were discussed herein with respect to anterior views of the vertebra (e.g., along the frontal axis) in FIGS. 10F, one of skill in the art will understand that patients also have defects along the sagittal axis. Further, the benefits of matching the defects are expected to extend to customizing endplates to match the defects along the sagittal axis in addition to matching defects along the sagittal axis.

Figure 11A:
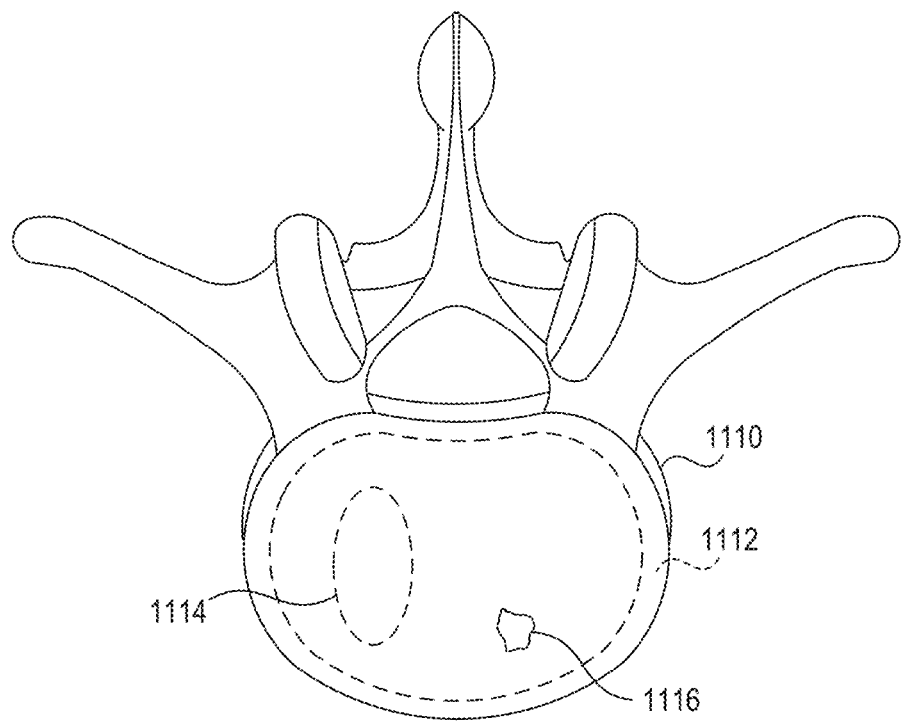
FIG. 11A is a schematic depiction of a vertebra illustrating various patient-specific vertebra conditions and topological features.
Figure 11B:
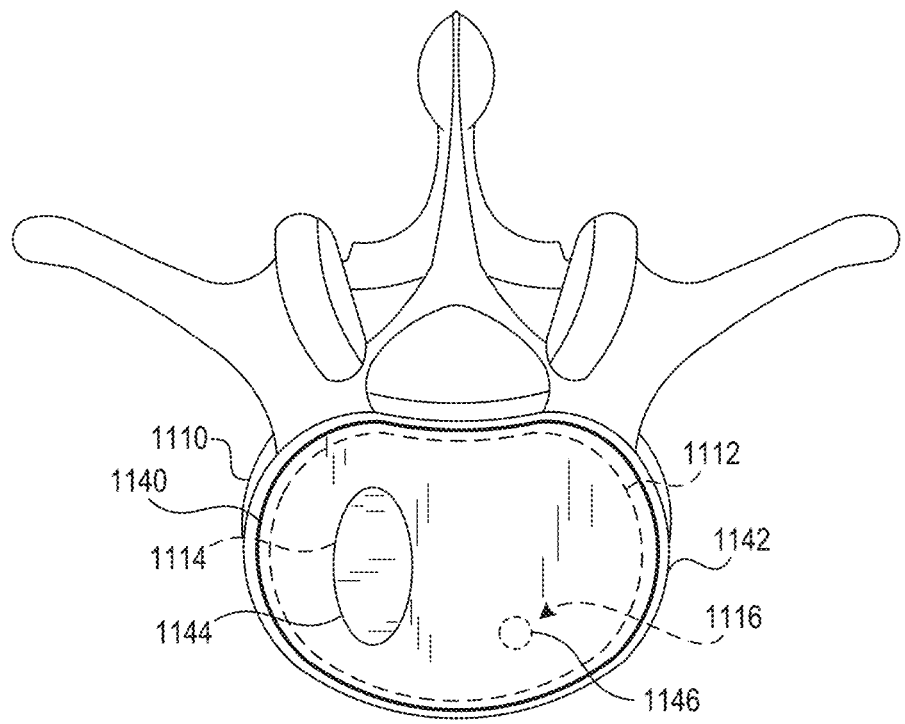
FIG. 11B is a schematic depiction of a patient-specific endplate customized to the vertebra of FIG. 11A in accordance with some embodiments of the present technology.

FIG. 11A is a schematic superior illustration of a vertebra 1110 illustrating various patient-specific vertebra conditions and topological features and FIG. 11B is a schematic superior illustration of a patient-specific endplate 1140 customized to the vertebra 1110. With reference to FIG. 11A, the vertebra 1110 includes a first region 1112 that is identified to be relatively strong compared to the remaining interior region of the vertebra 1110. In some embodiments, the first region 1112 is identified using the patient data received in block 702 of the method 700 discussed above with respect to FIG. 7. For example, the patient data can include a 3D CT scan that identifies both the bone structure and density in the vertebra 1110; and the method 700 can determine that the regions that are denser near the surface of the vertebra 1110 are stronger than other regions. For example, the first region 1112 can correspond to the cortical rim comprising bone with a strength (e.g., yield strength, ultimate strength, etc.) greater than the interior cancellous region. The system can analyze composition of tissue, vertebral endplate thicknesses, endplate geometry/contours, cortical shell thicknesses, vertebral body cortex thicknesses, or the like to determine loading capabilities at different locations along the vertebrae. In some embodiments, the first region 1112 is identified based on a comparison of the patient data to a plurality of reference patient data sets in a process analogous to the data phase 410 discussed above with respect to FIG. 4. For example, the patient data can indicate an age, gender, and medical condition for the patient, which is associated with a subset of reference patients with a similar age, gender, and medical condition. In some embodiments, the plurality of reference patient data sets can indicate that a specific region tends to be stronger than other regions in a predictable manner for patients analogous to the plurality of reference patients. Accordingly, the reoccurring area can be identified as the first region 1112.

As further illustrated in FIG. 11A, the vertebra 1110 includes a second region 1114 that is identified to be relatively weak compared to the surrounding region or remaining vertebral body. Like the first region 1112 discussed above, in various embodiments, the second region 1114 can be identified from the patient data, from a comparison of the patient data to reference patient data, and/or some combination therein. Further, the vertebra 1110 also includes a protrusion 1116. Like the first and second regions 1112, 1114, in various embodiments, the protrusion 1116 can be identified from the patient data, from a comparison of the patient data to reference patient data, and/or some combination therein.

With reference to FIG. 11B, once the first and second regions 1112, 1114 and the protrusion 1116 are identified, the design and manufacturing methods can produce the endplate 1140 customized to account for the identified features. As illustrated, for example, the endplate 1140 includes a first feature 1142 configured to transfer forces from an IBF device (e.g., device 830 of FIG. 8) into the first region 1112 of the vertebra 1110. Since the forces from the IBF device are transferred into a relatively strong portion of the vertebra 1110, the risk of damage to the vertebra can be reduced, thereby improving the expected outcome of a medical procedure using the endplate 1140.

Similarly, the endplate 1140 includes a second feature 1144 configured to limit, reduce, or avoid transferring forces from the IBF device into the second region 1114 of the vertebra 1110. In the illustrated embodiment, the second feature 1144 is a receiving-feature (e.g., a gap, a through-hole, etc.) that does not contact the vertebra 1110, thereby transferring no forces into the second region 1114. In various other embodiments, the second feature 1144 can include a webbed surface, a compressible and/or soft material, and/or various other suitable features. Since the forces from the IBF device are not overly transferred into a relatively weak portion of the vertebra 1110, the risk of damage to the vertebra can be reduced, thereby improving the expected outcome of a medical procedure using the endplate 1140.

Similarly, the endplate 1140 includes a third feature 1146 configured mate with the protrusion 1116 of the vertebra 1110. In the illustrated embodiment, the third feature 1146 is a valley generally corresponding to and sized to fit the protrusion 1116 therein. As a result, the endplate 1140 can maintain better contact with the vertebra 1110. For example, the endplate 1140 does not contact the focal point of the protrusion 1116 and form a bridge to another contact point, and instead mates with the entire surface of the vertebra 1110 outside of the second region 1114. The improved contact of the endplate 1140 is expected to improve the traction of the endplate on the vertebra as well as the expected outcome of a medical procedure using the endplate 1140.

FIGS. 12-16 are schematic illustrations of various IBF devices in accordance with various embodiments of the present technology. As discussed above, in some embodiments, the design of a patient-specific implant includes selecting a device from a group of possible devices based on the patient data and/or the desired anatomical configuration. Further, once a device is selected, the endplates can be custom manufactured to mate with both the patient's vertebra and the selected device.

Figure 12:
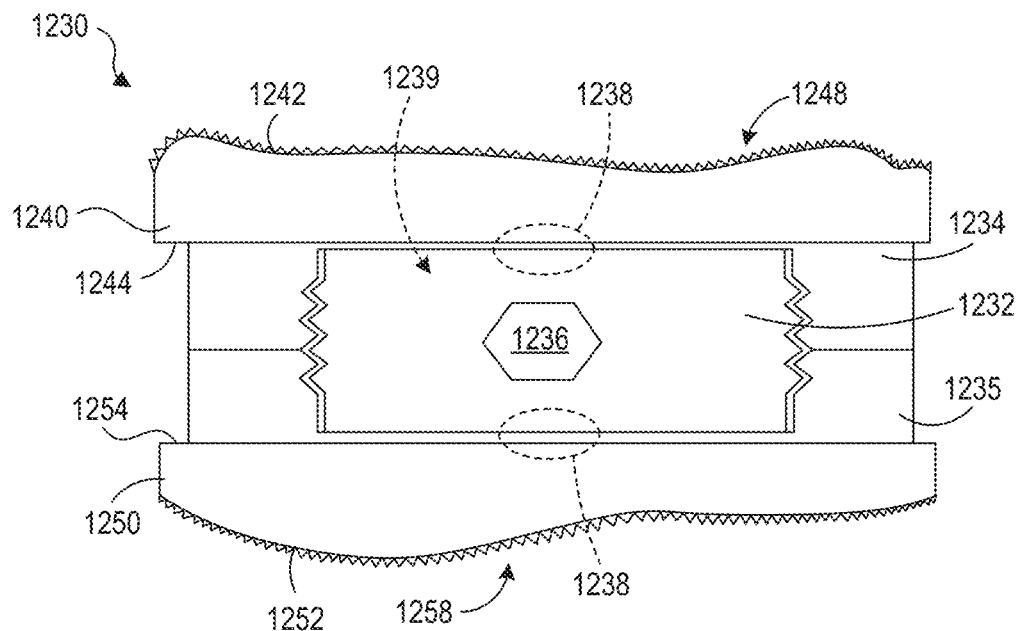
FIG. 12 is a schematic anterior illustration of a device in accordance with various embodiments of the present technology.
Figure 13:
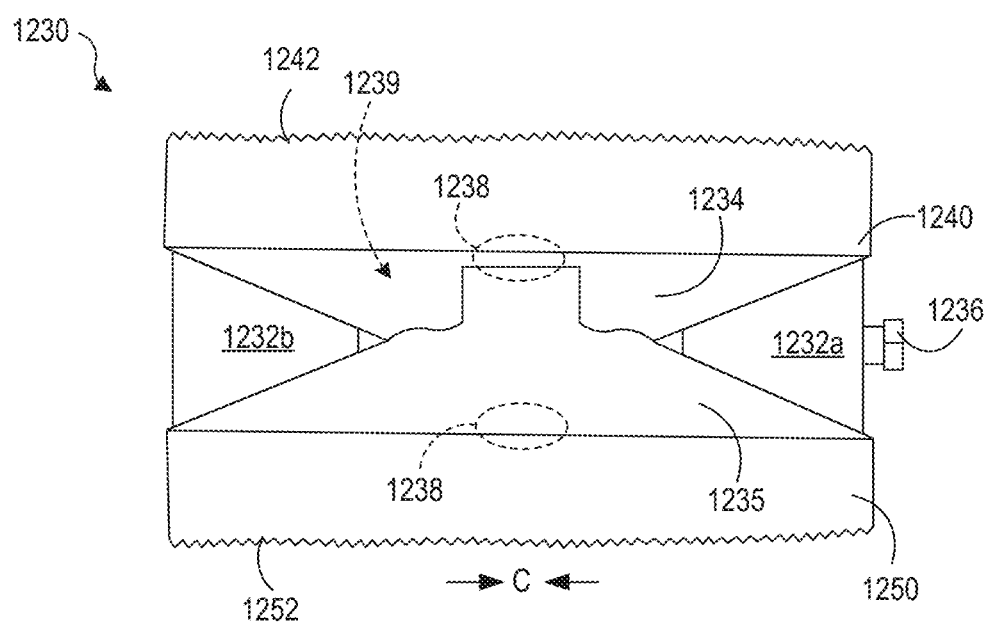
FIG. 13 is a schematic side illustration of a device in accordance with various embodiments of the present technology.

FIGS. 12 and 13 are schematic anterior and side views, respectively, illustrating additional details on a device 1230 of the type discussed above with respect to FIGS. 8A and 8B. As illustrated, for example, the device 1230 includes lateral end portions 1232 (shown in FIG. 13 as a first lateral end portion 1232a and a second lateral end portion 1232b), an upper component 1234 that mates with the lateral end portions 1232, a lower component 1235 that mates with the lateral end portions 1232, and an adjustment mechanism 1236 operably connected to the lateral end portions 1232. The adjustment mechanism 1236 can be turned in a first direction (e.g., clockwise) to draw the lateral end portions 1232 towards each other along axis C, thereby forcing the upper and lower components 1234, 1235 to move vertically upward and downward, respectively, to expand the device 1230. As described above, in some embodiments, the device 1230 includes a lockable stopping mechanism 1239 that can prevent the device 1230 from being expanded beyond a desired point. For example, in some embodiments, the stopping mechanism 1239 can be pre-operatively locked in position to prevent the expansion of the device 1230 past a predetermined point to provide a desired height restoration to a patient's spine. During operation, the device 1230 can be inserted then expanded until the stopping mechanism 1239 prevents further expansion.

The upper component 1234 is connected to a first endplate 1240, while the lower component 1235 is connected to a second endplate 1250. In the illustrated embodiment, the connections are achieved through lockable joints 1238 (referred to individually as a first lockable joint 1238a, and a second lockable joint 1238b). As also described above, the lockable joints 1238 allow the first and second endplates 1240, 1250 to be adjusted and locked to provide a desired lordotic and/or coronal correction to a patient's spine. In various embodiments, the configuration of the first and second endplates 1240, 1250 on the lockable joints 1238 can be pre-operatively and/or intraoperatively adjusted and locked.

As further illustrated, the first endplate 1240 includes a first surface 1242 that is configured to mate with an inferior surface of a superior vertebra 1210 and a second surface 1244 configured to mate with the upper component 1234 through the first lockable joint 1238a. As discussed above, the first surface 1242 is custom-manufactured with patient-specific features to mate with the topology of the inferior surface of the superior vertebra. Further, the first surface 1242 includes retaining features 1248 that frictionally engage the inferior surface of the superior vertebra to help maintain the position of the device 1230 once inserted between vertebral bodies. In the illustrated embodiment, the retaining features 1248 are oriented along a frontal axis. In some embodiments, the retaining features 1248 are oriented along a sagittal axis. In some embodiments, the first surface 1242 can include one or more retaining features 1248 oriented along the frontal axis and one or more retaining features 1248 oriented along the sagittal axis.

Similarly, the second endplate 1250 includes a first surface 1252 configured to mate with a superior surface of the inferior vertebra and a second surface 1254 configured to mate with the lower component 1235 through the second lockable joint 1238b. As discussed above, the first surface 1252 is custom-manufactured to with patient-specific features to mate with the topology of the superior surface of the inferior vertebra. Further, the first surface 1252 also includes retaining features 1258 that frictionally engage the superior surface of the inferior vertebra to help maintain the position of the device 1230 once inserted between two vertebra. In various embodiments, the first surface 1252 can include one or more retaining features 1258 oriented along the frontal axis (as shown) and one or more retaining features 1248 oriented along the sagittal axis (not shown).

Figure 14:
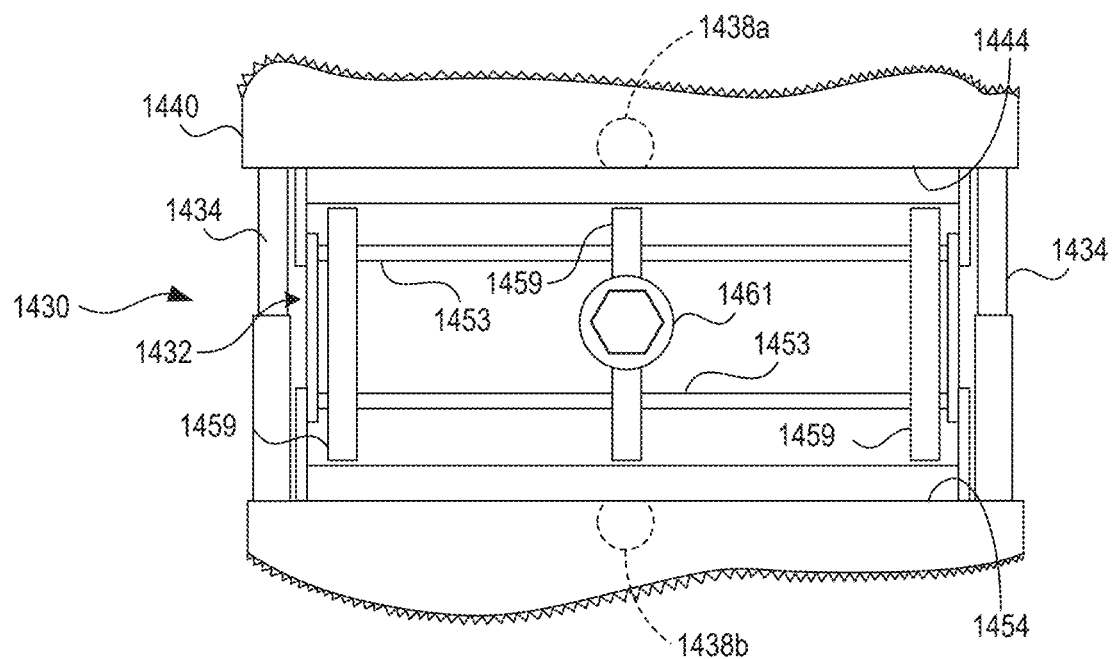
FIG. 14 is a schematic anterior illustration of another intervertebral body fusion device in accordance with various embodiments of the present technology.
Figure 15:
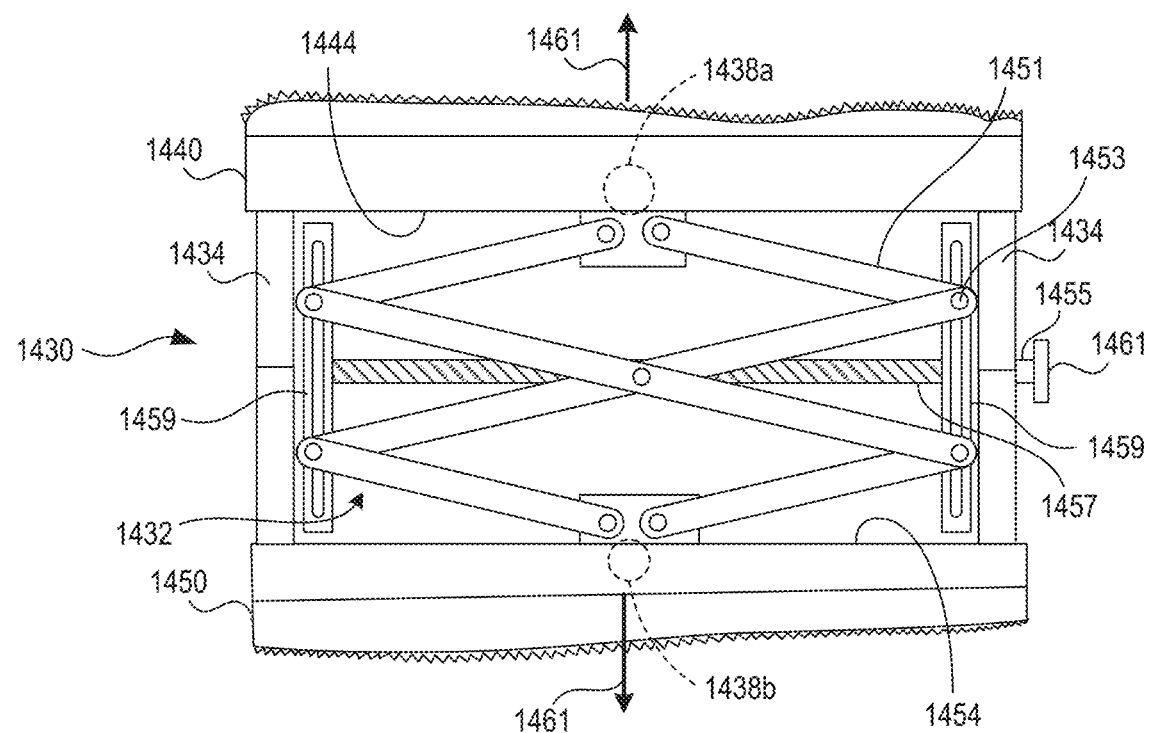
FIG. 15 is a schematic side illustration of another intervertebral body fusion device in accordance with various embodiments of the present technology.

FIGS. 14 and 15 are schematic anterior and side views, respectively, illustrating a patient-specific device 1430 in accordance with embodiments of the present technology. In the illustrated embodiment, the device 1430 includes an expandable scissor assembly 1432 operably connected to first and second lockable joints 1438a, 1438b (referred to collectively as "lockable joints 1438"). The first lockable joint 1438a is connected to a first endplate 1440 and the second lockable joint 1438b is connected to a second endplate 1450. In the illustrated embodiment, the device 1430 also includes telescoping supports 1434 connected to the first and second endplates 1440, 1450. The telescoping supports 1434 help support edge portions of the first and second endplates 1440, 1450 when the device 1430 is deployed in a patient's spine, thereby increasing the compressive strength of the device 1430. In the illustrated embodiment, the device 1430 includes four telescoping supports 1434. In various other embodiments, the device 1430 includes various other numbers of telescoping supports 1434, depending on the size of the device 1430, the expected compressive forces, the rigidity of the scissor assembly 1432 and/or ball joints, and/or any other suitable factor. Accordingly, in various embodiments, the device 1430 includes no telescoping supports 1434, one telescoping support 1434, two telescoping supports 1434, six telescoping supports 1434, or any other suitable number of telescoping supports 1434.

Further, in some embodiments, the telescoping supports 1434 are operatively coupled to the scissor assembly 1432 and/or the lockable joints 1438 to facilitate adjustment of the device 1430. For example, when the scissor assembly 1432 is expanded, the telescoping supports 1434 can automatically unlock and expand/extend to match the scissor assembly 1432; then when the scissor assembly 1432 is locked, the telescoping supports 1434 can automatically lock as well. Similarly, when the lockable joints 1438 are unlocked to be adjusted, the telescoping supports 1434 can automatically unlock to allow for quick adjustment; then when the lockable joints 1438 are locked, the telescoping supports 1434 can automatically lock as well. In some embodiments, the telescoping supports 1434 are locked and unlocked independent from the lockable joints 1438. In some such embodiments, the telescoping supports 1434 are interconnected to be locked and unlocked together. In other such embodiments, each individual telescoping support 1434 is locked and unlocked independent from the other components of the device 1430.

The scissor assembly 1432 can include a plurality of linkages 1451 (one identified), pins 1453 (one identified), and a screw drive assembly 1455 (FIG. 15). As illustrated with respect to FIG. 15, the screw drive assembly 1455 can include a threaded rod 1457 and connectors 1459. The connectors 1459 can include slots along which pins 1453 are capable of sliding. In operation, an instrument can be detachably coupled to a drive head 1461 to rotate the threaded rod 1457. The connectors 1459 can be moved towards one another to drive the lockable joints 1438a, 1438b away from each other, as indicated by arrows 1461. The number of linkages, connectors, pins, and configuration of the scissor assembly 1432 can be selected based on the desired amount of expansion, load bearing capabilities, or other design criteria. In some embodiments, the scissor assembly 1432 is fixedly coupled to the endplates 1440, 1450. For example, the scissor assembly 1432 can be fused, welded, or integrally formed with the endplates 1440, 1450.

Similar to the devices discussed above, the device 1430 can be pre-operatively and/or intraoperatively configured in various ways to customize the device to the patient and/or the intended medical treatment. For example, the size of the device 1430 can be selected based on patient-specific data and/or the intended medical treatment; the scissor assembly 1432 can be pre- or intraoperatively expanded then locked to provide a predetermined height restoration between vertebrae in the patient's spine; the angle of the first and second endplates 1440, 1450 on the lockable joints 1438 can be pre- or intraoperatively adjusted and locked; the first endplate 1440 can include a first surface with a topology customized to a superior vertebrae; and the second endplate 1450 can include a first surface with a topology customized to an inferior vertebrae.

As further illustrated in FIGS. 14 and 15, the first and second endplates 1440, 1450 can be customized to mate with the type of IBF device that is selected to treat the patient. For example, the first endplate 1440 includes a second surface 1444 that is customized to mate with the first lockable joint 1438a as well as the number of telescoping supports 1434 that are selected for the device 1430. Similarly, the second endplate 1450 includes a second surface 1454 that is customized to mate with the second lockable joint 1438b and the number of telescoping supports 1434 that are selected for the device 1430.

Figure 16:
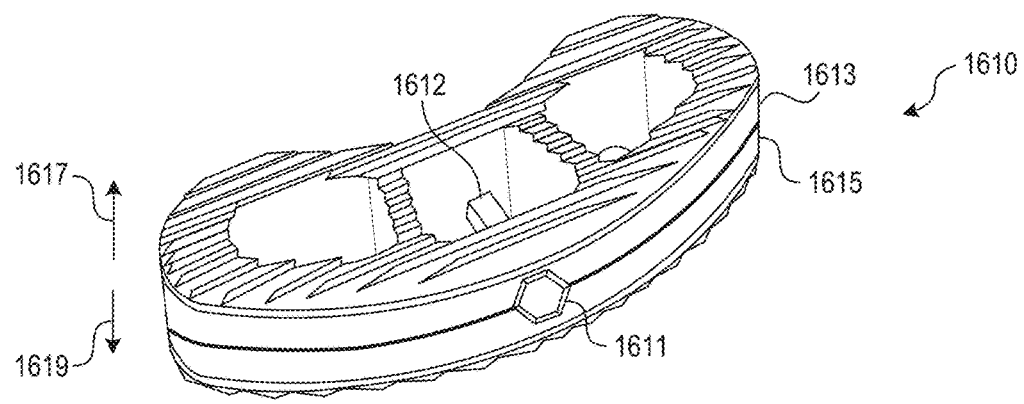
FIGS. 16-18 illustrate examples of further intervertebral body fusion devices in patient-specific sizes in accordance with various embodiments of the present technology.
Figure 17:
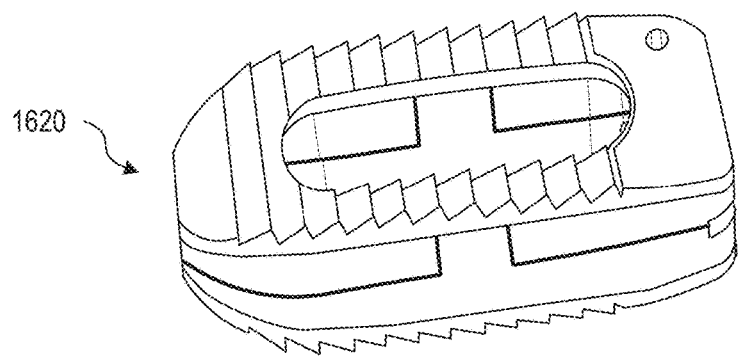
Figure 18:
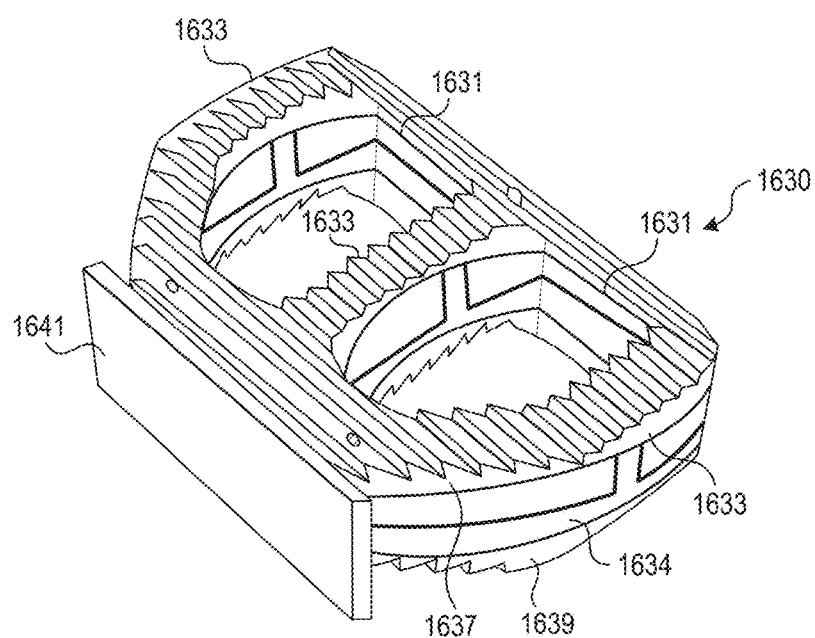

FIGS. 16-18 schematically illustrate examples of IBF devices with customized sizes in accordance with various embodiments of the present technology. The IBF devices can include features discussed in connection with, for example, FIGS. 1A-1B and 8A-15 and can be expanded as discussed in connection with FIGS. 1B-2, 8A-9, and 19-22.

FIG. 16 illustrates a medium sized arcuate IBF device 1610. Two IBF devices 1610 can be implanted at opposite sides of the intervertebral space. In some procedures, multiple IBF devices 1610 can have the same expanded height to provide uniform height restoration across the disc space. In other procedures, IBF devices 1610 configured for placement within the same intervertebral/disc space (e.g., at the same spinal level) can have different heights to maintain an angled disc space. For example, IBF devices 1610 at different heights can be deployed to provide curvature corrections for scoliotic or curved spines. A drive element 1611 can be rotated to drive an expansion shaft 1612. The expansion shaft can be connected to one or more scissors mechanisms, wedge assemblies, slide assemblies, or other components for driving apart upper and lower endplates 1613, 1615, as previously described herein. For example, drive element 1611 can be rotated clockwise to move apart the upper and lower endplates 1613, 1615, as indicated by arrows 1617, 1619. In this manner, the IBF device 1610 can be expanded from the illustrated collapsed configuration to an expanded configuration. IBF devices 1610, 1620, and 1630 of FIGS. 16-18 are illustrated in collapsed configurations.

FIG. 17 illustrates a relatively small IBF device 1620 with an elongated window to receive material to facilitate fusion. In some embodiments, the upper and lower portions of the IBF device 1620 can be rotatable relative to one another via one or more joints, such as the joints discussed in connection with FIGS. 21-24.

FIG. 18 shows a relatively large sized IBF device 1630. The IBF device 1630 has a shape generally matching the endplates to be contacted. In some embodiments, the IBF device 1630 has a pair of windows 1631 configured to receive material. Expansion mechanisms can be located within three connecting portions 1633. The description of the connecting portions 1633 apply equally to each other unless indicated otherwise.

Each connecting portion 1633 can include an expansion mechanism 1634 (one identified) that includes an expansion mechanism and upper and lower endplates 1637, 1639. The endplates 1637, 1639 can include ridges or grooves to facilitate frictional interaction with bone. In some embodiments, the endplates 1637, 1639 can have anchors, a smooth surface, or other features.

The IBF device 1630 has a plate 1641 configured to contact the side wall of vertebral bodies. When the IBF device 1630 is inserted into the intervertebral space, the plate 1641 can contact the side wall of the vertebral body, thereby positioning the IBF device 1630 at the desired location. The systems disclosed herein (e.g., system 200 of FIG. 2) can determine the appropriate dimensions for the plate 1641 to ensure that the vertebral bodies will be contacted, thereby locating the implant. The other devices disclosed herein can have positioning features to facilitate positioning at the intervertebral space.

The systems and methods disclosed herein can select the number of devices, dimensions (e.g., length, width, curvature, expansion height, angular position of contact surfaces, surface texturing) of the devices, interface features (e.g., grooves, texturing, etc.), and expansion mechanisms based on, for example, the condition to be treated and/or the desired anatomical outcome. For example, the system 200 of FIG. 2 can also design multiple IBF devices 1610 for a procedure. The surgeon can select devices based on visualization of the disc space during the surgical procedure. This allows for increased flexibility during the surgical procedure. A surgical procedure can involve implantation of devices having different configurations. For example, two IBF devices 1610 of FIG. 16 can be implanted at one level and the IBF device 1630 of FIG. 18 can be implanted at another level. This allows for flexibility when designing treatment plans.

As described above, the endplates used in conjunction with the IBF device, expansion components, or other parts of the device that can be manufactured after the other portions or components of the device are selected. Accordingly, in addition to features configured to mate with the patient-specific topology of a vertebra, the endplates can include features configured to facilitate joinder to the size of the IBF device or components chosen. For example, the size of the endplates used can also vary with the size of the IBF device (e.g., an endplate used with the IBF device 1620 can be smaller than an endplate used with the IBF device 1630). In some embodiments, the size of the endplate can remain constant, while features configured to mate with the IBF device are varied according to size.

Figure 19:
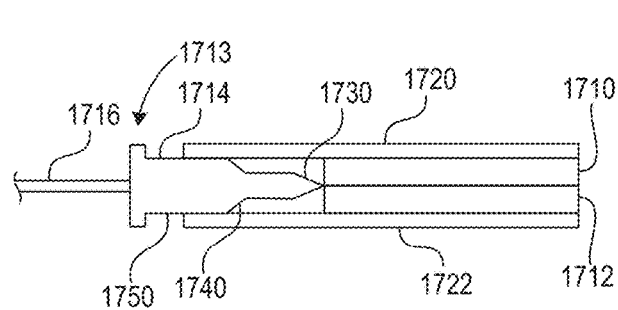
FIG. 19 is a side view of an expansion mechanism in an intervertebral body fusion device in accordance with various embodiments of the present technology.

FIG. 19 is a side view of an expansion mechanism 1700 in accordance with an embodiment of the technology. The expansion mechanism 1700 can include an upper engagement member 1710 and a lower engagement member 1712 and a wedge 1714. The wedge 1714 can be pushed distally by a drive rod 1716 to move apart endplates 1720, 1722. When the wedge 1714 is advanced distally, a pointed tip region 1730 can drive apart the engagement members 1710, 1712. As the wedge 1714 advances distally, the endplates 1720, 1722 are gradually moved apart. The wedge 1714 can include a sloped region 1740 that further drives apart the engagement members 1710, 1712 until a main body 1750 is positioned directly between the engagement members 1710, 1712. The wedge 1714 can be designed for patient-specific expansion and manufactured using the techniques disclosed herein. The expansion mechanism 1700 can be adapted for use with any of the IBF devices described herein.

Figure 20:
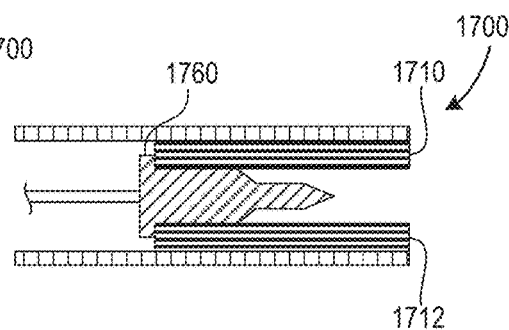
FIG. 20 is a cross-sectional view of the expansion mechanism in the expanded intervertebral body fusion device of FIG. 19 in accordance with various embodiments of the present technology.

FIG. 20 is a cross-sectional view of the expansion mechanism 1700. The wedge 1714 is positioned between the engagement members 1710, 1712. The wedge 1714 can include stops 1760 that engage the sides of the engagement members 1710, 1712, thereby locking the implant in a fully deployed (e.g., expanded) configuration. The features, configuration, composition, and other features of the driver can be selected based on the desired expansion. For example, the height of the body 1750 can correspond to the desired expansion distance. In the illustrated embodiment, the driver 1713 expands the device in incremental steps by using sloped surfaces. The number of sloped regions can be selected based on the number of desired incremental expansion steps. In the illustrated embodiment, there are two sloped surfaces: a first sloped surface at the distal tip portion 1730 and a second sloped surface 1740 proximal to the first sloped surface. As a result, the device can be incrementally expanded between (1) a collapsed configuration (shown in FIG. 19) before the pointed tip region 1730 is advanced distally such that the engagement members 1710, 1712 remain proximate to one another, (2) an intermediate configuration (not shown) during which the portion of the wedge 1714 between the first sloped surface 1730 and the second sloped surface 1740 is positioned between the engagement members 1710, 1712, and (3) a fully expanded configuration (shown in FIG. 20) in which the main body 1750 is positioned between the engagement members 1710, 1712. Additionally, the slopes of the surfaces can be selected based on the rate of expansion.

Figure 21:
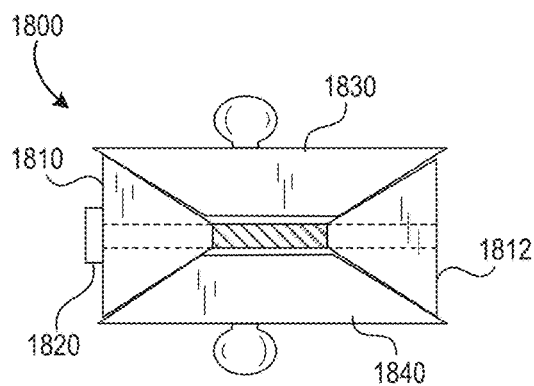
FIG. 21 illustrates another expansion mechanism in accordance with various embodiments of the present technology.
Figure 22:
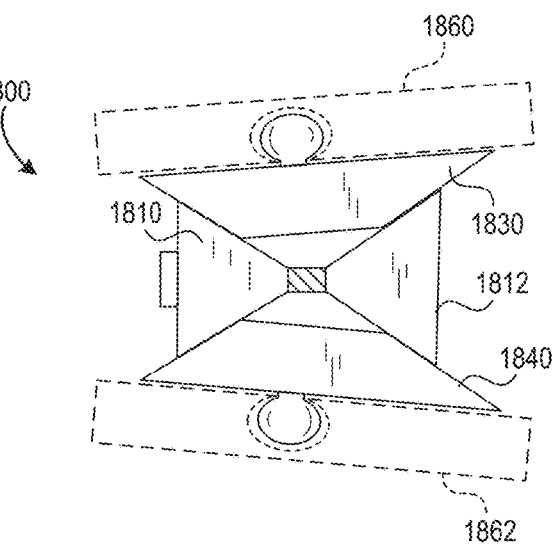
FIG. 22 illustrates a fusion device with the expansion mechanism of FIG. 21 in an expanded configuration in accordance with various embodiments of the present technology.

FIGS. 21 and 22 show an expansion mechanism configured to move the implant to an expanded angled configuration to, for example, provide a lordosis correction. Referring to FIG. 21, the driver device 1800 includes wedges 1810, 1812, and a drive mechanism 1820. The drive mechanism 1820 further includes a threaded shaft extending between the wedges 1810, 1812. As the threaded shaft is rotated, the wedges 1810, 1812 are forced inwardly toward one another. The inward movement of the wedges 1810, 1812 causes upper and lower members 1830, 1840 (e.g., endplates, elongate contact members, etc.) to be driven apart, increasing the height of the driver device 1800.

The wedges 1810, 1812 can be designed with surfaces that cause an at least slightly angular expansion of the drive mechanism 1820. For example, FIG. 22 shows the wedge 1812 with a sloped surfaces configured to drive the upper and lower members 1830, 1840 further apart than the wedge 1810. More specifically, the wedge 1812 may be slightly larger than, or have surfaces with a greater slope than, the wedge 1810. This causes endplates 1860, 1862 (illustrated in phantom line) to be moved to an angular position relative to one another upon expansion of the driver device 1800. In some embodiments, the members 1830, 1840 include joints, such as ball joints illustrated in FIG. 22. The size, configuration, and surface finish of the wedges 1810, 1812 can be selected based on a collapsed configuration (e.g., maximum width), rate of expansion, expanded configuration, or the like.

Figure 23:
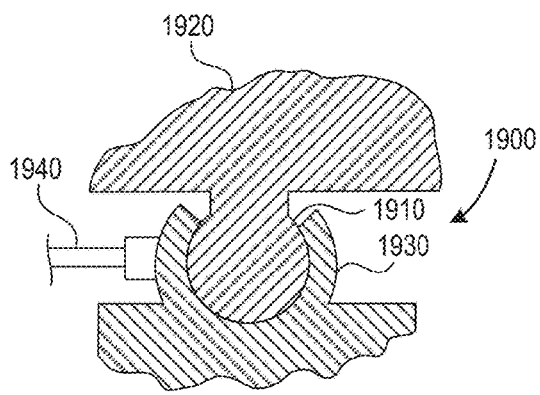
FIG. 23 illustrates a joint in accordance with various embodiments of the present technology.

FIG. 23 is a cross-sectional view of a joint 1900 that can be used with the devices and implants as disclosed herein. The joint 1900 can include a ball 1910 connected to a component 1920. The component 1920 can be a connector, scissors mechanism, endplate, or other component discussed herein. The joint further includes a socket 1930 configured to hold the ball 1910. The socket 1930 can be connected to or part of an endplate, expansion mechanism, or other component disclosed herein. In some locking embodiments, the joint 1900 includes a lock element 1940 that can be operated to lock and unlock the joint 1900 (e.g., by increasing or decreasing the width of the socket 1930, advancing or retracting a locking element into the socket 1930, or other suitable mechanisms). The configuration, features, and connections of the joints can be selected based on the desired range of motion and mechanical characteristics of the implant. In some embodiments, the joint 1900 permits relative movement between an endplate and a main body of an IBF device (e.g., as described above with respect to FIGS. 1A and 1B).

Figure 24:
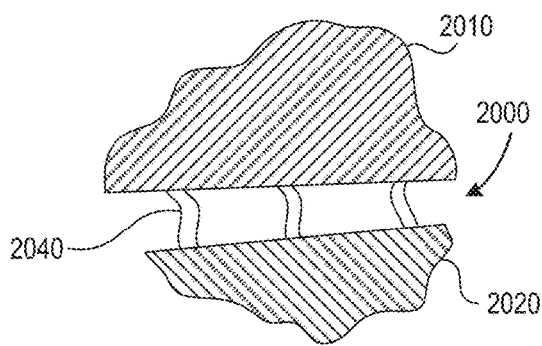
FIG. 24 illustrates a connection between components of an implantable device in accordance with various embodiments of the present technology.

FIG. 24 shows a joint 2000 for connecting two components 2010, 2020. The joint 2000 includes tethers 2040 (one identified) permanently coupled to the components 2010, 2020. In some embodiments, the tethers 2040 are at least semi-rigid such that they permit relative movement of the two components 2010, 2020, but maintain structural integrity to prevent collapsing on themselves. In some embodiments, the component 2010 can be part of an endplate and the component 2020 can be part of an expansion mechanism. The joint 2000 can allow relative movement between the endplate and the expansion mechanism during implantation to allow the patient-specific endplate to naturally seat against the anatomical features of a vertebral body. The amount of movement between the two components 2010, 2020 can be increased or decreased by increasing or decreasing the length of the tethers 2040.

The embodiments, features, systems, devices, materials, methods and techniques described herein may, in some embodiments, be similar to any one or more of the embodiments, features, systems, devices, materials, methods and techniques described in the following:

U.S. application Ser. No. 16/048,167, filed on Jul. 27, 2017, titled "SYSTEMS AND METHODS FOR ASSISTING AND AUGMENTING SURGICAL PROCEDURES";

U.S. application Ser. No. 16/242,877, filed on Jan. 8, 2019, titled "SYSTEMS AND METHODS OF ASSISTING A SURGEON WITH SCREW PLACEMENT DURING SPINAL SURGERY";

U.S. application Ser. No. 16/207,116, filed on Dec. 1, 2018, titled "SYSTEMS AND METHODS FOR MULTI-PLANAR ORTHOPEDIC ALIGNMENT";

U.S. application Ser. No. 16/352,699, filed on Mar. 13, 2019, titled "SYSTEMS AND METHODS FOR ORTHOPEDIC IMPLANT FIXATION";

U.S. application Ser. No. 16/383,215, filed on Apr. 12, 2019, titled "SYSTEMS AND METHODS FOR ORTHOPEDIC IMPLANT FIXATION";

U.S. application Ser. No. 16/569,494, filed on Sep. 12, 2019, titled "SYSTEMS AND METHODS FOR ORTHOPEDIC IMPLANTS";

U.S. Application No. 62/773,127, filed on Nov. 29, 2018, titled "SYSTEMS AND METHODS FOR ORTHOPEDIC IMPLANTS";

U.S. Application No. 62/928,909, filed on Oct. 31, 2019, titled "SYSTEMS AND METHODS FOR DESIGNING ORTHOPEDIC IMPLANTS BASED ON TISSUE CHARACTERISTICS";

U.S. application Ser. No. 16/735,222, filed Jan. 6, 2020, titled "PATIENT-SPECIFIC MEDICAL PROCEDURES AND DEVICES, AND ASSOCIATED SYSTEMS AND METHODS";

U.S. application Ser. No. 16/987,113, filed Aug. 6, 2020, titled "PATIENT-SPECIFIC ARTIFICIAL DISCS, IMPLANTS AND ASSOCIATED SYSTEMS AND METHODS";

U.S. application Ser. No. 16/990,810, filed Aug. 11, 2020, titled "LINKING PATIENT-SPECIFIC MEDICAL DEVICES WITH PATIENT-SPECIFIC DATA, AND ASSOCIATED SYSTEMS, DEVICES, AND METHODS";

U.S. application Ser. No. 17/463,054, filed Aug. 31, 2021, titled "BLOCKCHAIN MANAGED MEDICAL IMPLANTS;"

U.S. application Ser. No. 17/085,564, filed Oct. 30, 2020, titled "SYSTEMS AND METHODS FOR DESIGNING ORTHOPEDIC IMPLANTS BASED ON TISSUE CHARACTERISTICS"; and U.S. application Ser. No. 17/100,396, filed Nov. 20, 2020, titled "PATIENT-SPECIFIC VERTEBRAL IMPLANTS WITH POSITIONING FEATURES."

All of the above-identified patents and applications are incorporated by reference in their entireties. In addition, the embodiments, features, systems, devices, materials, methods, and techniques described herein may, in certain embodiments, be applied to or used in connection with any one or more of the embodiments, features, systems, devices, or other matter.

Conclusion

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any material incorporated herein by reference conflicts with the present disclosure, the present disclosure controls. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Furthermore, as used herein, the phrase "and/or" as in "A and/or B" refers to A alone, B alone, and both A and B. Additionally, the terms "comprising," "including," "having," and "with" are used throughout to mean including at least the recited feature(s) such that any greater number of the same features and/or additional types of other features are not precluded.

From the foregoing, it will also be appreciated that various modifications may be made without deviating from the disclosure or the technology. For example, one of ordinary skill in the art will understand that various components of the technology can be further divided into subcomponents, or that various components and functions of the technology may be combined and integrated. In addition, certain aspects of the technology described in the context of particular embodiments may also be combined or eliminated in other embodiments. Furthermore, although advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A system comprising:
an expandable interbody device comprising:
a first endplate having a first patient-specific configuration configured to mate with a first vertebral body of a patient;
a second endplate having a second patient-specific configuration configured to mate with a second vertebral body of the patient, the second patient-specific configuration being different than the first patient-specific configuration;
a body positioned between the first endplate and the second endplate, the body including an expansion mechanism configured to adjust a distance between the first endplate and the second endplate;
a first joint coupling the first endplate to the body and permitting the first endplate to at least partially rotate relative to the body for a first range of motion having multiple degrees of freedom specific to the patient;
a second joint coupling the second endplate to the body and permitting the second endplate to at least partially rotate relative to the body for a second range of motion having multiple degrees of freedom specific to the patient; and
a surgical plan, viewable on a user device, with information for a collapsed version of the expandable interbody device and an expanded version of the expandable interbody device, wherein the surgical plan includes at least one image of the expandable interbody device expanded to achieve a corrected disc height, wherein the surgical plan shows the first joint and the second joint articulated to achieve corrected anatomical configuration at the corrected disc height for a spinal segment of the patient after the expandable interbody device is implanted and expanded in the patient.

2. The system of claim 1 wherein the expansion mechanism is configured to provide incremental adjustments to the distance between the first endplate and the second endplate.

3. The system of claim 1 wherein the expansion mechanism is configured to adjust the distance between the first endplate and the second endplate by a predetermined amount based at least in part on a patient-specific treatment plan.

4. The system of claim 1 wherein the expansion mechanism includes at least one of a drive screw, a scissors mechanism, or a wedge.

5. The system of claim 1, further comprising a stopper mechanism configured to prevent the expansion mechanism from increasing the distance between the first endplate and the second endplate past a predetermined distance.

6. A system comprising:
an expandable interbody device comprising:

a first endplate having a first patient-specific configuration configured to mate with a first vertebral body of a patient;

a second endplate having a second patient-specific configuration configured to mate with a second vertebral body of the patient, the second patient-specific configuration being different than the first patient-specific configuration;

a body positioned between the first endplate and the second endplate, the body including an expansion mechanism configured to adjust a distance between the first endplate and the second endplate;

a first joint coupling the first endplate to the body and permitting the first endplate to at least partially rotate relative to the body for a first range of motion having multiple degrees of freedom specific to the patient; wherein the first joint is a lockable joint having (i) an unlocked configuration in which the first endplate is moveable relative to the body, and (ii) a locked configuration in which the first endplate is not moveable relative to the body; a second joint coupling the second endplate to the body and permitting the second endplate to at least partially rotate relative to the body for a second range of motion having multiple degrees of freedom specific to the patient, wherein the second joint is a lockable joint having (i) an unlocked configuration in which the second endplate is moveable relative to the body, and (ii) a locked configuration in which the second endplate is not moveable relative to the body; and a surgical plan, viewable on a user device, with information for a collapsed version of the expandable interbody device with at least one of the first and second joints in the locked configuration and an expanded version of the expandable interbody device with the at least one of the first and second joints in the locked configuration.

7. The system of claim 6 wherein the expandable interbody device is adjustable into a predetermined, patient-specific geometrical orientation configured to induce a predetermined, patient-specific adjustment to spinal anatomy of the patient.

8. The system of claim 7 wherein the expandable interbody device is configured to be adjusted into the predetermined, patient-specific geometrical orientation intraoperatively.

9. The system of claim 6 wherein, when the expandable interbody device is implanted between the first and second vertebral bodies, the first endplate is configured to contact a majority of a corresponding endplate of the first vertebral body and the second endplate is configured to contact a majority of a corresponding endplate of the second vertebral body.

10. A system comprising:
a surgical plan viewable on a user device, the surgical plan including virtual model information for an expansion of a device to achieve a corrected disc height of a patient and for a corrected anatomical configuration of a spine of the patient at the corrected disc height for the patient, wherein the surgical plan includes at least one image of a collapsed version of the device and an expanded version of the device;
wherein the device is for performing intervertebral body fusion between a superior vertebra and an inferior vertebra of a vertebral joint of the patient, the device comprising:

an expandable main body configured to be locked in an expansion configuration, wherein the expandable main body includes a first lockable ball joint on an upper surface of the main body and a second lockable ball joint on a lower surface of the main body;

a first endplate connected to the main body at the first lockable ball joint, the first endplate having a superior surface positioned to engage a surface of the superior vertebra,
wherein the first lockable ball joint is configured to permit the first endplate to rotate relative to the main body for a first range of motion having multiple degrees of freedom specific to the patient,
wherein the superior surface of the first endplate includes one or more patient-specific features; and a second endplate connected to the main body at the second lockable ball joint, the second endplate having an inferior surface positioned to engage a surface of the inferior vertebra,
wherein the second lockable ball joint is configured to permit the second endplate to rotate relative to the main body for a second range of motion having multiple degrees of freedom specific to the patient such that the first lockable ball joint and the second lockable ball joint cooperate to achieve the corrected anatomical configuration at the corrected disc height,
wherein the inferior surface of the second endplate includes one or more patient-specific features.

11. The system of claim 10 wherein the expandable main body includes a screw jack expansion mechanism.

12. The system of claim 10 wherein the expandable main body includes a scissor jack mechanical expansion mechanism.

13. The system of claim 10 wherein at least one of the one or more patient-specific features of the superior surface corresponds to a topographical feature on the surface of the superior vertebra to customize a fit of the first endplate to the superior vertebra.

14. The system of claim 10 wherein at least one of the one or more patient-specific features of the inferior surface corresponds to a topographical feature on the surface of the inferior vertebra to customize a fit of the second endplate to the inferior vertebra.

15. The system of claim 10 wherein at least one of the first endplate and the second endplate includes a sloped contact surface configured to provide a correction to a misalignment at the vertebral joint, the misalignment associated with one or more of scoliosis, lordosis, or kyphosis.

16. The system of claim 10 wherein at least one of the one or more patient-specific features of the superior surface is configured to transfer forces from the device to the superior vertebra in accordance with identified strong or weak regions in the surface of the superior vertebra.

17. The system of claim 10 wherein at least one of the one or more patient-specific features of the inferior surface is configured to transfer forces from the device to the inferior vertebra in accordance with identified strong or weak regions in the surface of the inferior vertebra.

18. A system comprising:
a virtual model of an expandable interbody device in an expanded configuration to achieve a corrected disc height and a predicted anatomical configuration of at least a portion of a spine of a subject;
a surgical plan, viewable on a user device, including an image of the virtual model and information for the predicted anatomical configuration;

the expandable interbody device, comprising:
- a first endplate having a patient-specific configuration for seating against a first vertebral body of the subject;
- a second endplate having a configuration different from the patient- specific configuration;
- an expansion mechanism operable to drive apart the first and second endplates such that the first endplate contacts the first vertebral body and the second endplate contacts a second vertebral body of the subject; and
- at least one joint coupling configured with a patient specific range of motion based on the first endplate and the second endplate such that the at least one joint coupling achieves the predicted anatomical configuration when the at least one joint is locked to achieve the corrected disc height in the subject.

19. The system of claim 18 wherein the first endplate has a first contact surface with a first topology that is different from a second topology of a second contact surface of the second endplate.

20. The system of claim 18 wherein the first and second endplates define a varying height interverbal space between the first and second vertebral bodies.

21. The system of claim 18 wherein the first endplate has at least one anatomic-receiving feature positioned to receive an anatomic feature of the first vertebral body when the first endplate is seated against an endplate of the first vertebral body.

22. The system of claim 18 wherein the first endplate is asymmetrical with respect to a sagittal plane and/or a frontal plane of the expandable interbody device.

23. The system of claim 18 wherein the expandable interbody device is asymmetrical with respect to a sagittal plane, a frontal plane, and/or a transverse plane of the expandable interbody device.

24. The system of claim 18, further comprising a drive element detachably coupleable to an instrument and connected to the expansion mechanism, wherein the drive element rotates in a first direction to cause expansion of the expandable interbody device and in a second direction to cause collapsing of the expandable interbody device.

25. The system of claim 18 wherein the expansion mechanism includes at least one of drive screw, a scissors mechanism, or a wedge.

26. The system of claim 18, further comprising at least one joint connecting the expansion mechanism to the first endplate.

27. The system of claim 18, further comprising at least one ball joint operable to allow adjustment of an angle relationship between the first and second endplates.

28. The system of claim 18 wherein the first endplate is configured to contact a majority of the first vertebral body and the second endplate is configured to contact a majority of the second vertebral body when the subject stands vertically.

29. The system of claim 18 wherein the expandable interbody device is configured for a substantially gapless interface directly between the first endplate and the first vertebral body.

30. A system comprising:
- a surgical plan, viewable on a user device, including pre-expansion anatomical information of a patient for delivery of an expandable interbody device and post-expansion anatomical information of the patient based on the expandable interbody device being in a locked expanded state to achieve a corrected disc height for fusion of adjacent vertebrae of the patient;
- the expandable interbody device, comprising:
  - a first endplate having a first patient-specific configuration configured to mate with a first vertebral body of the patient;
  - a second endplate having a second patient-specific configuration configured to mate with a second vertebral body of the patient, the second patient-specific configuration being different than the first patient-specific configuration;
  - a body positioned between the first endplate and the second endplate, the body including an expansion mechanism configured to adjust a distance between the first endplate and the second endplate; and
  - at least one joint coupling configured with a patient specific range of motion based on the first endplate and the second endplate such that the at least one joint coupling achieves corrected fixation between the adjacent vertebrae at the corrected disc height when the expandable interbody device is implanted and expanded in the patient.

* * * * *